United States Patent
Peyman

(10) Patent No.: US 11,309,081 B2
(45) Date of Patent: *Apr. 19, 2022

(54) TELEMEDICINE SYSTEM WITH DYNAMIC IMAGING

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 67 days.

This patent is subject to a terminal disclaimer.

(21) Appl. No.: 16/666,230

(22) Filed: Oct. 28, 2019

(65) Prior Publication Data

US 2020/0066405 A1 Feb. 27, 2020

Related U.S. Application Data

(63) Continuation-in-part of application No. 15/897,085, filed on Feb. 14, 2018, now Pat. No. 10,456,209, and
(Continued)

(51) Int. Cl.
*G16H 40/67* (2018.01)
*A61B 5/1171* (2016.01)
(Continued)

(52) U.S. Cl.
CPC ........... *G16H 40/67* (2018.01); *A61B 5/1172* (2013.01); *A61B 5/1176* (2013.01);
(Continued)

(58) Field of Classification Search
CPC ........ G16H 40/67; G16H 30/20; G16H 10/60; G16H 20/40; A61B 5/1176; A61B 5/1172;
(Continued)

(56) References Cited

U.S. PATENT DOCUMENTS

| 4,213,678 A | 7/1980 | Pomerantzeff et al. |
| 4,247,176 A | 1/1981 | Ito |

(Continued)

FOREIGN PATENT DOCUMENTS

WO 2010/129074 A1 11/2010

OTHER PUBLICATIONS

Ertel et al., "Retinal Evaluation Efficacy of a Scanning Laser Opthalmoscope (Optos P200) Compared to a Digital Retinal Camera," White Rock Optometry Clinic, Nov. 4, 2009, pp. 1-15 (and p. 16 providing the earliest recorded date).
(Continued)

*Primary Examiner* — John B Strege
(74) *Attorney, Agent, or Firm* — The Law Office of Patrick F. O'Reilly III, LLC

(57) ABSTRACT

A telemedicine system with dynamic imaging is disclosed herein. In some embodiments, the telemedicine system comprises a laser imaging and treatment apparatus, and associated systems and methods that allow a physician (e.g., a surgeon) to perform laser surgical procedures on an eye structure or a body surface with a laser imaging and treatment apparatus disposed at a first (i.e. local) location from a control system disposed at a second (i.e. remote) location, e.g., a physician's office. Also, in some embodiments, communication between the laser imaging and treatment apparatus and control system is achieved via the Internet®. Further, in some embodiments, the telemedicine system includes a dynamic imaging system and/or a facial recognition system that verifies the identity of a patient, and is capable of being used for other important applications, such as tracking and analyzing trends in a disease process.

16 Claims, 24 Drawing Sheets

Related U.S. Application Data a continuation-in-part of application No. 15/368,759, filed on Dec. 5, 2016, now Pat. No. 9,931,171, which is a continuation-in-part of application No. 14/715,325, filed on May 18, 2015, now Pat. No. 9,510,974, which is a continuation-in-part of application No. 13/865,901, filed on Apr. 18, 2013, now Pat. No. 9,037,217, which is a continuation-in-part of application No. 13/573,100, filed on Aug. 20, 2012, now Pat. No. 8,903,468, which is a continuation-in-part of application No. 12/925,518, filed on Oct. 22, 2010, now Pat. No. 8,452,372, application No. 16/666,230, filed on Oct. 28, 2019, which is a continuation-in-part of application No. PCT/US2018/041958, filed on Jul. 13, 2018.

(60) Provisional application No. 62/459,009, filed on Feb. 14, 2017, provisional application No. 62/549,941, filed on Aug. 24, 2017, provisional application No. 62/563,582, filed on Sep. 26, 2017, provisional application No. 61/455,111, filed on Oct. 13, 2010, provisional application No. 62/532,098, filed on Jul. 13, 2017, provisional application No. 62/671,525, filed on May 15, 2018.

(51) Int. Cl.
*A61B 5/1172* (2016.01)
*A61B 5/00* (2006.01)
*G06K 9/00* (2022.01)
*G16H 30/20* (2018.01)
*G06N 20/00* (2019.01)

(52) U.S. Cl.
CPC ........ *A61B 5/7264* (2013.01); *G06K 9/00087* (2013.01); *G06K 9/00288* (2013.01); *G06N 20/00* (2019.01); *G16H 30/20* (2018.01); *G06K 2209/05* (2013.01)

(58) Field of Classification Search
CPC ..... A61B 5/7264; A61B 5/441; A61B 5/7275; A61B 5/1112; A61B 5/0095; A61B 5/01; A61B 5/0066; A61B 5/165; A61B 5/0077; A61B 5/4836; A61B 2562/0204; G06K 9/00087; G06K 9/00288; G06K 9/00422; G06K 9/00093; G06K 9/00281; G06K 9/00013; G06K 2209/05; G06K 2009/00932; G06N 20/00; G06N 3/0454; G06N 3/0445; G06N 3/08
See application file for complete search history.

(56) References Cited

U.S. PATENT DOCUMENTS

| | | |
|---|---|---|
| 4,736,744 A | 4/1988 | Koike et al. |
| 4,757,541 A | 7/1988 | Beadles |
| 4,759,360 A | 7/1988 | Nakanishi et al. |
| 4,838,680 A | 6/1989 | Nunokawa |
| 5,049,147 A | 9/1991 | Danon |
| 5,572,266 A | 11/1996 | Ohtsuka |
| 5,713,047 A | 1/1998 | Kohayakawa |
| 5,742,374 A | 4/1998 | Nanjo et al. |
| 5,815,242 A | 9/1998 | Anderson et al. |
| 5,855,553 A | 1/1999 | Tajima et al. |
| 5,923,399 A | 7/1999 | Van de Velde |
| 5,943,116 A | 8/1999 | Zeimer |
| 5,993,001 A | 11/1999 | Bursell et al. |
| 6,173,068 B1 | 1/2001 | Prokoski |
| 6,296,358 B1 | 10/2001 | Cornsweet et al. |
| 6,496,594 B1 | 12/2002 | Prokoski |
| 6,529,617 B1 | 3/2003 | Prokoski |
| 6,544,254 B1 | 4/2003 | Bath |
| 6,546,198 B2 | 4/2003 | Ohtsuka |
| 6,636,696 B2 | 10/2003 | Saito |
| 7,079,688 B1 | 7/2006 | Deco et al. |
| 7,206,435 B2 | 4/2007 | Fujimura et al. |
| 7,206,626 B2 | 4/2007 | Quaid, III |
| 7,890,211 B2 | 2/2011 | Green |
| 8,070,289 B2 | 12/2011 | Peyman |
| 8,121,663 B2 | 2/2012 | Peyman et al. |
| 8,452,372 B2 | 5/2013 | Peyman |
| 10,796,476 B1 * | 10/2020 | Xing ....................... G06T 15/08 |
| 2002/0031230 A1 | 3/2002 | Sweet et al. |
| 2003/0072479 A1 | 4/2003 | Sofia Totterman et al. |
| 2003/0208189 A1 | 11/2003 | Payman |
| 2004/0250210 A1 | 12/2004 | Huang et al. |
| 2006/0004286 A1 | 1/2006 | Chang et al. |
| 2006/0142657 A1 | 6/2006 | Quaid et al. |
| 2006/0274921 A1 | 12/2006 | Rowe |
| 2007/0100226 A1 | 5/2007 | Yankelevitz et al. |
| 2007/0238957 A1 | 10/2007 | Yared |
| 2007/0258626 A1 | 11/2007 | Reiner |
| 2008/0205703 A1 | 8/2008 | Brown et al. |
| 2008/0294013 A1 | 11/2008 | Gobeyn et al. |
| 2009/0069677 A1 | 3/2009 | Chen et al. |
| 2009/0093798 A1 | 4/2009 | Charles |
| 2009/0177094 A1 | 7/2009 | Brown et al. |
| 2009/0187288 A1 | 7/2009 | Shimada et al. |
| 2009/0240149 A1 | 9/2009 | Peyman |
| 2010/0054550 A1 * | 3/2010 | Okada ................ G06K 9/00308 382/118 |
| 2010/0060728 A1 | 3/2010 | Bublitz et al. |
| 2010/0082019 A1 | 4/2010 | Neev |
| 2010/0106475 A1 | 4/2010 | Smith et al. |
| 2010/0164950 A1 | 7/2010 | Zhao et al. |
| 2010/0245766 A1 | 9/2010 | Zhang et al. |
| 2010/0265498 A1 | 10/2010 | Zhang |
| 2011/0015521 A1 | 1/2011 | Faul |
| 2011/0118748 A1 | 5/2011 | Itkowitz |
| 2011/0282333 A1 | 11/2011 | Herekar et al. |
| 2012/0114195 A1 | 5/2012 | Matsuda et al. |
| 2012/0150159 A1 | 6/2012 | Kunath-Fandrei et al. |
| 2012/0165620 A1 | 6/2012 | Tanis et al. |
| 2013/0142399 A1 * | 6/2013 | Razzak ................ G06K 9/6234 382/118 |
| 2013/0222684 A1 | 8/2013 | Mueller et al. |
| 2014/0254939 A1 | 9/2014 | Kimura et al. |
| 2014/0343416 A1 | 11/2014 | Panescu et al. |
| 2014/0376785 A1 * | 12/2014 | Bathiche ................ G06T 5/001 382/118 |
| 2016/0071111 A1 * | 3/2016 | Wang ................ G06Q 30/0643 705/44 |
| 2016/0101358 A1 | 4/2016 | Ibrahim et al. |
| 2019/0259476 A1 * | 8/2019 | Armijos ................ G16H 10/60 |
| 2020/0145410 A1 * | 5/2020 | Allburn ................ H04L 63/108 |
| 2020/0257891 A1 * | 8/2020 | Cole ..................... G06K 9/6257 |
| 2020/0311871 A1 * | 10/2020 | Yu ......................... G06T 3/4053 |

OTHER PUBLICATIONS

First office action on the merits (Non-Final Rejection) in U.S. Appl. No. 12/925,518, dated Mar. 7, 2012.
Second office action on the merits (Final Rejection) in U.S. Appl. No. 12/925,518, dated May 1, 2012.
Third office action on the merits (Non-Final Rejection) in U.S. Appl. No. 12/925,518, dated Dec. 5, 2012.
Fourth office action on the merits (Final Rejection) in U.S. Appl. No. 12/925,518, dated Mar. 21, 2013.
Notice of Allowance in U.S. Appl. No. 12/925,518, dated Apr. 12, 2013.
First action interview office action summary in U.S. Appl. No. 13/573,100, dated Apr. 2, 2014.
Second office action on the merits (Final Rejection) in U.S. Appl. No. 13/573,100, dated Jun. 16, 2014.
Notice of Allowance in U.S. Appl. No. 13/573,100, dated Sep. 30, 2014.
First office action on the merits (Non-Final Rejection) in U.S. Appl. No. 13/865,901, dated Mar. 20, 2014.

(56) References Cited

OTHER PUBLICATIONS

Second office action on the merits (Final Rejection) in U.S. Appl. No. 13/865,901, dated Aug. 15, 2014.
Notice of Allowance in U.S. Appl. No. 13/865,901, dated Jan. 21, 2015.
First office action on the merits (Non-Final Rejection) in U.S. Appl. No. 14/715,325, dated Jun. 24, 2015.
Second office action on the merits (Final Rejection) in U.S. Appl. No. 14/715,325, dated Dec. 1, 2015.
Notice of Allowance in U.S. Appl. No. 14/715,325, dated Oct. 14, 2016.
Konig et al. "Nanodissection of Human Chromosomes and Ultraprecise Eye Surgery With Nanojoule Near Infrared Femtosecond Laser Pulses." Proceedings of SPIE, vol. 4633, 2002, pp. 11-22.
Csutak et al. "Agreement Between Image Grading of Conventional (45-degrees) and Ultra Wide-Angle (200-degrees) Digital Images of the Macula in the Reykjavik Eye Study." Eye, vol. 24. Published Jun. 4, 2010. pp. 1568-1575.
Boyce et al. "Multispectral Iris Analysis: A Preliminary Study." Proceedings of Computer Vision and Pattern Recognition Workshop on Biometrics (CVPRW), Jun. 2006. pp. 1-9.
Makanjuola et al. "3D-Holoscopic Imaging: A New Dimension to Enhance Imaging in Minimally Invasive Therapy in Urologic Oncology." Journal of Endourology, vol. 27, No. 5, May 2013, pp. 535-539.
CBS News. "3D Holograms Help Israeli Heart Surgeons." Reuters. Jan. 7, 2014. Published online at http://www.cbsnews.com/news/3d-holograms-help-israeli-heart-surgeons/, includes a video. Printout of article includes two (2) pages.
First office action on the merits (Non-Final Rejection) in U.S. Appl. No. 15/368,759, dated Feb. 16, 2017.
Second office action on the merits (Final Rejection) in U.S. Appl. No. 15/368,759, dated Jul. 3, 2017.
Third office action on the merits (Non-Final Rejection) in U.S. Appl. No. 15/368,759, dated Oct. 12, 2017.
Notice of Allowance in U.S. Appl. No. 15/368,759, dated Jan. 31, 2018.
First office action on the merits (Non-Final Rejection) in U.S. Appl. No. 15/897,085, dated Oct. 30, 2018.
Second office action on the merits (Final Rejection) in U.S. Appl. No. 15/897,085, dated Apr. 25, 2019.
Notice of Allowance in U.S. Appl. No. 15/897,085, dated Aug. 30, 2019.
PCT Form 210, International Search Report for PCT/US2018/041958, dated Oct. 15, 2018.
PCT Form 237, Written Opinion of the International Searching Authority for PCT/US2018/041958, dated Oct. 15, 2018.
Rodriguez-Ramos et al., "The CAFADIS camera: a new tomographic wavefront sensor for Adaptive Optics"; Feb. 24, 2010; published by EDP Sciences. Abstract p. 1-2. Article pp. 1-6 (8 pages total).
M.J. Aitkenhead. "A neural network face recognition system". Engineering Applications of Artificial Intelligence 16 (2003). pp. 167-176. (Year: 2003).

* cited by examiner

TELEMEDICINE SYSTEM WITH DYNAMIC IMAGING

CROSS-REFERENCE TO RELATED APPLICATIONS

This patent application is a continuation-in-part of U.S. patent application Ser. No. 15/897,085, filed Feb. 14, 2018; which claims the benefit of U.S. Provisional Application No. 62/459,009, filed on Feb. 14, 2017, U.S. Provisional Application No. 62/549,941, filed on Aug. 24, 2017, and to U.S. Provisional Application No. 62/563,582, filed on Sep. 26, 2017; and U.S. patent application Ser. No. 15/897,085 is a continuation-in-part of U.S. patent application Ser. No. 15/368,759, filed Dec. 5, 2016, now U.S. Pat. No. 9,931,171; which is a continuation-in-part of U.S. patent application Ser. No. 14/715,325, filed May 18, 2015, now U.S. Pat. No. 9,510,974; which is a continuation-in-part of U.S. patent application Ser. No. 13/865,901, filed Apr. 18, 2013, now U.S. Pat. No. 9,037,217; which is a continuation-in-part of U.S. patent application Ser. No. 13/573,100, filed Aug. 20, 2012, now U.S. Pat. No. 8,903,468; which is a continuation-in-part of U.S. patent application Ser. No. 12/925,518, filed Oct. 22, 2010, now U.S. Pat. No. 8,452,372; which claims the benefit of U.S. Provisional Application No. 61/455,111, filed Oct. 13, 2010; the disclosure of each of which is hereby incorporated by reference as if set forth in their entirety herein.

This patent application is also a continuation-in-part of Patent Cooperation Treaty Patent Application No. PCT/US2018/041958, filed Jul. 13, 2018; which claims the benefit of U.S. Provisional Application No. 62/532,098, filed on Jul. 13, 2017, U.S. Provisional Application No. 62/671,525, filed on May 15, 2018, U.S. Provisional Application No. 62/549,941, filed on Aug. 24, 2017, and to U.S. Provisional Application No. 62/563,582, filed on Sep. 26, 2017; the disclosure of each of which is hereby incorporated by reference as if set forth in their entirety herein.

FIELD OF THE INVENTION

The present invention relates to methods and systems for telemedicine and for laser treatment of the eye or a body surface. More particularly, the present invention relates to a telemedicine system with dynamic imaging and/or facial recognition capabilities.

BACKGROUND OF THE INVENTION

As is well known in the art, various eye disorders, such as diabetic retinopathy, vascular occlusion, neovascularization and age macular degeneration, can, and in most instances will, have an adverse effect on the retina. Indeed, if not treated at the appropriate stage, noted diseases, particularly, diabetic retinopathy, can lead to severe losses in vision.

Various methods and systems have thus been developed to aid in the diagnosis of the noted eye diseases. The method often employed by an eye care specialist, such as an ophthalmologist, is to examine the ocular fundus (the inside back surface of the eye containing the retina, blood vessels, nerve fibers, and other structures) with an ophthalmoscope.

The ophthalmoscope is a small, hand-held device, which, when appropriately positioned, shines light through a subject's pupil to illuminate the fundus. By properly focusing the light reflected from the subject's fundus, an examiner can observe the fundus structures.

As is well known in the art, examination of the ocular fundus can also be achieved using a fundus or slit lamp camera. Illustrative are the apparatus and systems disclosed in U.S. Pat. Nos. 5,713,047, 5,943,116, 5,572,266, 4,838,680, 6,546,198, 6,636,696, 4,247,176, 5,742,374 and 6,296,358.

Various method and systems have also been developed to treat eye disorders, such as diabetic retinopathy, glaucoma and age macular degeneration. One known method of treating the noted eye disorders, as well as retinal detachment, is laser coagulation of predetermined biological structures of the eye, such as the retina.

As is well known in the art, during laser coagulation of an eye structure, laser energy is transmitted to the structure to effect coagulation thereof. A typical laser coagulation system thus includes a laser energy or beam source, such as a beam projector, a slit image projector or lamp for forming a slit image on the eye, and observation equipment for observing the slit image and laser spot(s) in the eye. Illustrative are the laser coagulation systems disclosed in U.S. Pat. Nos. 4,759,360 and 4,736,744.

A major drawback associated with each of the noted conventional systems, as well as most known laser coagulation systems (and associated methods), is that the conventional slit lamp systems require a contact lens to neutralize the refractive power of the cornea. A contact lens is also necessary to provide a variable field of view of the retina up to 130°.

As is well known in the art, the contact lens must be appropriately positioned on the surface of the cornea and held at the desired position by the specialist, e.g., surgeon, while looking through the slit lamp microscope.

During this conventional laser coagulation procedure, the contact lens is positioned on the cornea, and held in position by the surgeon so as to permit the surgeon to view the retina through the slit lamp microscope during the laser application to the retina. In all conventional contact systems, the field of view is limited (e.g., maximum 50-60 degrees) and the surgeon is required to move the contact lens from one side of the eye to the other side of the eye during the procedure, and the patient is also required to move his or her eye, in order to permit the surgeon to see the peripheral retina.

There are several drawbacks associated with the use of a contact lens during laser coagulation. A major drawback is that the use of a contact lens requires topical anesthesia and a dilated pupil for laser application. As is well known in the art, a contact lens can, and in many instances will, cause corneal abrasion on an anesthetized cornea.

A further drawback associated with conventional laser coagulation procedures is that the laser procedures are dependent on the steadiness of the physician's hands and the subject's head.

Another apparatus that is often used for laser energy delivery to the peripheral retina is the indirect ophthalmoscope. Use of the indirect ophthalmoscope requires a physician to hold an appropriate convex lens in front of the eye (pupil) with one hand to focus the laser beam on the retina, while the eye is indented with another hand to bring the peripheral retina into the field of view for laser application.

In the indirect ophthalmoscopy technique, which is an alternative conventional method, the physician (i.e., surgeon) does not place a contact lens on the cornea, but rather he or she has to indent the peripheral part of the eye with an indenter (or scleral depressor) to bring the peripheral retinal areas into view, and additionally, the patient has to move the eye side to side.

Although laser delivery with an indirect ophthalmoscope eliminates the need for a contact lens, there are still drawbacks and disadvantages associated with use of an indirect ophthalmoscope. A major drawback is that during laser delivery (and, hence, coagulation of a desired eye structure), the ophthalmoscope is often carried on the physician's head for 30-60 mins. This extended period causes extreme fatigue for the physician.

The indentation of the eye for the extended period is also very unpleasant for the subject or patient.

A further drawback associated with the use of an indirect ophthalmoscope for laser coagulation is that the indirect ophthalmoscope does not provide a retained record or documentation for future evaluation. Further, in most instances, the subject typically requires subsequent fundus photography.

None of the abovedescribed conventional methods are suitable for remote laser application because they are limited in their field of view (typically 50-60 degrees). Also, the eye movement that is needed with these systems to view the entire retina renders them unsuitable for remote applications.

It would thus be desirable to provide non-contact systems and methods for laser coagulation of eye structures to treat eye disorders, and are capable of being effectively utilized to treat patients located at a remote site.

It is therefore an object of the present invention to provide non-contact systems and methods for laser coagulation of eye structures that substantially reduce or overcome the noted drawbacks and disadvantages associated with conventional contact-based laser coagulation systems and methods.

It is another object of the present invention to provide non-contact apparatus, systems and methods for laser imaging and coagulation of an eye structure.

It is yet another object of the present invention to provide non-contact apparatus, systems and methods for laser imaging and coagulation of the retina and its periphery to treat retina and choroideal disorders and/or diseases.

It is still another object of the present invention to provide a system for remote laser treatment of an eye structure or a body surface that is further capable of performing photodynamic therapy on a patient.

It is yet another object of the present invention to provide a telemedicine system or a remote laser treatment system with dynamic imaging that more accurately verifies the identity of a patient, and is capable of being used for other important applications, such as tracking and analyzing trends in a disease process.

It is still another object of the present invention to provide a remote laser treatment system that determines the geographical location of the local laser generation unit of the system so as to ensure that the local laser generation unit has not been improperly intercepted or stolen by unauthorized individuals.

SUMMARY OF THE INVENTION

The present invention is directed to laser imaging and coagulation apparatus, systems and methods that allow an eye specialist, e.g., an ophthalmologist or surgeon, to perform laser surgery on an eye structure, e.g. retina, with an integral laser imaging and coagulation apparatus disposed at a first (i.e. local) location from a control system disposed at a second (i.e. remote) location, e.g., a physician's office. The laser imaging and coagulation apparatus, systems and methods of the invention thus make it possible for an ophthalmologist to screen and perform laser surgery to treat various eye disorders, including, without limitation, diabetic retinopathy, vascular occlusion, neovascularization and age macular degeneration from a geographically remote location. The laser imaging and treatment system described herein may also be used to perform photodynamic therapy on a patient.

In one embodiment of the invention, the laser coagulation system includes (i) at least a first laser-imaging system disposed at a first location, the first laser-imaging system including a first laser-imaging apparatus, a photoacoustic system, a first processor and a local control module, the first laser-imaging apparatus including a wide angle digital image acquisition system for acquiring digital images of a subject's eye structure and a laser generation system for transmitting an aiming laser beam and at least a first coagulation laser beam to the eye structure, the first coagulation laser beam having a first laser energy, the photoacoustic system being configured to measure temperature of eye structure tissue subjected to the first laser energy, the local control module including local operation, local operation and performance simulation and local safety and verification sub-modules; and (ii) a central control system disposed at a remote site, the central control system including a second processor and a remote control module, the remote control module including remote operation, remote operation and performance simulation, and remote safety and verification sub-modules, the remote operations sub-module being configured to facilitate communications between a remote physician and the remote processor, and perform a laser coagulation procedure on the eye structure in an actual control mode.

In some embodiments of the invention, the local operation sub-module is configured to acquire at least a first eye structure image from the digital image acquisition system and transmit the first eye structure image to the remote site, receive a target laser transmission area and laser transmission parameters from a remote physician, apply an active contour algorithm to partition the first eye structure image into a grid map, perform a scatter laser (focal or grid) coagulation of the eye structure under the remote physician's command, acquire a plurality of post-procedure eye structure images, and transmit the post-procedure eye structure images to the remote site for evaluation and verification of treatment.

In some embodiments, the remote operations sub-module is further configured to execute a virtual treatment of the eye structure and perform a test surgical procedure in association with the local operation and performance simulation sub-module.

In some embodiments, the remote operation and performance simulation sub-module is configured to test performance parameters of the local operation module and perform virtual treatment of the eye structure by the remote physician.

In some embodiments of the invention, the photoacoustic system is configured to control the laser generation system.

In one embodiment of the invention, the eye structure comprises the retina.

In some embodiments of the invention, the laser coagulation system also includes eye tracking means for tracking movement of the eye.

In some embodiments of the invention, the laser coagulation system also includes facial recognition means for identifying and/or verifying the identity of the subject.

In one embodiment, communication by and between the central control system and the laser-imaging apparatus is achieved via the Internet®.

In another embodiment, the laser coagulation system includes:

a local control system disposed at a first location and a central control system disposed at a remote site, the remote site being at a second location;

at least a first laser-imaging system disposed at the first location, the laser-imaging system including a laser-imaging apparatus, a first processor and a local control module;

the laser-imaging apparatus including a digital image acquisition system configured to acquire digital images of the eye structure or the body surface, the local control module including local operation, local operation and performance simulation, and local safety and verification sub-modules;

a laser generation system configured to generate and transmit at least a first aiming laser beam and at least a first coagulation laser beam, and means for controlling the digital image acquisition system and the laser generation system;

a central control system disposed at the remote site, the central control system including a second processor and a remote control module, the remote control module including remote operation, remote operation and performance simulation, and remote safety and verification sub-modules; and the remote operation sub-module being configured to facilitate communications between a remote physician and the second processor, and perform a laser coagulation procedure on the eye structure or the body surface in an actual control mode, the remote operation sub-module including a touchscreen interface configured to enable the remote physician to draw a target laser treatment area or areas on a digitized image of the eye structure or the body surface.

In yet another embodiment, the laser coagulation system includes:

a local control system disposed at a first location and a central control system disposed at a remote site, the remote site being at a second location, the local control system being operatively coupled to the central control system by means of a computer network;

at least a first laser-imaging system disposed at the first location, the laser-imaging system including a laser-imaging apparatus, a laser generation system, a first computing device with a first processor, and a local control module;

the laser-imaging apparatus including a digital image acquisition system configured to acquire a digitized image of the eye structure or the body surface, the local control module including local operation, local operation and performance simulation, and local safety and verification sub-modules, the local operation sub-module configured to acquire the digitized image of the eye structure or the body surface from the digital image acquisition system and transmit the digitized image to the remote site;

the laser generation system including an aiming laser configured to generate and transmit an aiming laser beam to the eye structure or the body surface, and a treatment laser configured to generate and transmit at least a first coagulation laser beam to the eye structure or the body surface;

the central control system including a second computing device with a second processor, and a remote control module, the remote control module including remote operation, remote operation and performance simulation, and remote safety and verification sub-modules; and the remote operation sub-module being configured to facilitate communications between a remote physician and the second processor of the second computing device, and perform a laser coagulation procedure on the eye structure or the body surface in an actual control mode in which the treatment laser is configured to transmit the first coagulation laser beam to the eye structure or the body surface.

In some embodiments of the invention, the first laser-imaging system further includes an image recognition sensor configured to capture images of a patient at the first location so that an identity of the patient or an identity of a body portion of the patient is capable of being identified and verified prior to the laser coagulation procedure being performed on the eye structure or the body surface in the actual control mode.

In some embodiments, the image recognition sensor is operatively coupled to the first computing device, the first computing device being specially programmed to compare a first reference digital image of the patient captured by the image recognition sensor at a first time to a second digital image of the patient captured by the image recognition sensor at a second subsequent time, and to determine if the second digital image of the patient matches or substantially matches the first reference digital image of the patient (i.e., the second digital image of the patient substantially matches the first reference digital image of the patient when there are only minor differences between the two images, e.g., a blemish on the face of patient that appears in the second digital image, but not in the first reference digital image).

In some embodiments, when the first computing device determines that the second digital image of the patient substantially matches the first reference digital image of the patient, the first computing device is specially programmed to generate a matched image confirmation notification that is sent to the second computing device at the remote site in order to inform the remote physician that the patient has been identified and verified; and, when the first computing device determines that the second digital image of the patient does not substantially match the first reference digital image of the patient, the first computing device is specially programmed to generate a non-matching image notification that is sent to the second computing device at the remote site in order to inform the remote physician that the patient has not been properly identified and verified.

In some embodiments, when the first computing device determines that the second digital image of the patient does not substantially match the first reference digital image of the patient, the first computing device is further specially programmed to automatically lock out the treatment laser so that the treatment laser is not capable of being fired.

In some embodiments, the image recognition sensor is in the form of a multispectral camera configured to capture the images of the patient using both visible light and infrared light.

In some embodiments, the first laser-imaging system further includes a voice recognition sensor configured to capture speech waveforms generated by the patient at the first location so that an identity of the patient is capable of being identified and verified prior to the laser coagulation procedure being performed on the eye structure or the body surface in the actual control mode.

In some embodiments, the voice recognition sensor is operatively coupled to the first computing device, the first computing device being specially programmed to compare a first reference speech waveform of the patient captured by the voice recognition sensor at a first time to a second speech waveform of the patient captured by the voice recognition sensor at a second subsequent time, and to determine if the second speech waveform of the patient matches or substantially matches the first reference speech waveform of the patient (i.e., the second speech waveform of the patient substantially matches the first reference speech waveform of the patient when there are only minor differences between the two speech waveforms, e.g., a minor difference in the tone of the speech).

In some embodiments, when the first computing device determines that the second speech waveform of the patient matches or substantially matches the first reference speech waveform of the patient, the first computing device is specially programmed to generate a matched speech confirmation notification that is sent to the second computing device at the remote site in order to inform the remote physician that the patient has been identified and verified; and, when the first computing device determines that the second speech waveform of the patient does not match or substantially match the first reference speech waveform of the patient, the first computing device is specially programmed to generate a non-matching speech notification that is sent to the second computing device at the remote site in order to inform the remote physician that the patient has not been properly identified and verified.

In some embodiments, when the first computing device determines that the second speech waveform of the patient does not substantially match the first reference speech waveform of the patient, the first computing device is further specially programmed to automatically lock out the treatment laser so that the treatment laser is not capable of being fired.

In some embodiments, the voice recognition sensor is in the form of a microphone configured to capture the speech waveforms generated by the patient over a speech frequency range between 50 Hertz and 5,000 Hertz.

In still another embodiment, the laser treatment system includes:

a local control system disposed at a first location and a central control system disposed at a remote site, the remote site being at a second location, the local control system being operatively coupled to the central control system by means of a computer network;

at least a first laser-imaging system disposed at the first location, the laser-imaging system including a laser-imaging apparatus, a laser generation system, a first computing device with a first processor, and a local control module;

the laser-imaging apparatus including a digital image acquisition system configured to acquire a digitized image of the eye structure or the body surface, the local control module including local operation, local operation and performance simulation, and local safety and verification sub-modules, the local operation sub-module configured to acquire the digitized image of the eye structure or the body surface from the digital image acquisition system and transmit the digitized image to the remote site;

the laser generation system including an aiming laser configured to generate and transmit an aiming laser beam to the eye structure or the body surface, and a treatment laser configured to generate and transmit at least a first treatment laser beam to the eye structure or the body surface;

the central control system including a second computing device with a second processor, and a remote control module, the remote control module including remote operation, remote operation and performance simulation, and remote safety and verification sub-modules; and the remote operation sub-module being configured to facilitate communications between a remote physician and the second processor of the second computing device, and perform a laser treatment procedure on the eye structure or the body surface in an actual control mode in which the treatment laser is configured to transmit the first treatment laser beam to the eye structure or the body surface so as to surgically alter the eye structure or the body surface.

In some embodiments of the invention, the first laser-imaging system further includes an image recognition sensor configured to capture images of a patient at the first location so that an identity of the patient or an identity of a body portion of the patient is capable of being identified and verified prior to the laser treatment procedure being performed on the eye structure or the body surface in the actual control mode.

In some embodiments, the image recognition sensor is operatively coupled to the first computing device, the first computing device being specially programmed to compare a first reference digital image of the patient captured by the image recognition sensor at a first time to a second digital image of the patient captured by the image recognition sensor at a second subsequent time, and to determine if the second digital image of the patient substantially matches the first reference digital image of the patient.

In some embodiments, the image recognition sensor is in the form of a holoscopic three-dimensional camera configured to capture the images of the patient in three-dimensional form, and wherein the second computing device comprises a graphical user interface in the form of a multiview, three-dimensional visual display device configured to enable the remote physician or another observer at the remote site to perform a three-dimensional analysis of the three-dimensional images of the patient that are produced as a result of the patient being instructed to perform a task that alters one or more detectable physical attributes of the patient.

In some embodiments, the first computing device is specially programmed to utilize the three-dimensional images so as to collectively take into account a plurality of physiological characteristics of a body area of the patient that reflect the one or more altered physical attributes when the identity of the patient or the identity of the body portion of the patient is identified and verified.

In some embodiments, the multiview, three-dimensional visual display device of the second computing device is in the form of a three-dimensional digital holographic display device.

In some embodiments, the three-dimensional digital holographic display device comprises one or more thin or ultrathin holographic optical elements for producing high-resolution three-dimensional images, and wherein the three-dimensional digital holographic display device comprises an autostereoscopic three-dimensional display to eliminate the need for the physician or the another observer to wear special eyewear while performing the three-dimensional analysis of the three-dimensional images of the patient.

In some embodiments, the multiview, three-dimensional visual display device of the second computing device is in the form of a volumetric three-dimensional display so as to generate the three-dimensional images of the patient formed by voxels with spatial depth and volume.

In some embodiments, the second computing device comprises a graphical user interface in the form of virtual reality glasses worn by the remote physician or another observer at the remote site, the virtual reality glasses configured to enable the remote physician or the another observer at the remote site to perform an analysis of the images of the patient that are produced as a result of the patient being instructed to perform a task that alters one or more detectable physical attributes of the patient.

In some embodiments, the laser treatment system further comprises an optical coherence tomography imaging system, near-infrared optical tomography imaging system, or a frequency modulated continuous wave imaging system operatively coupled to the first computing device, the optical coherence tomography imaging system, near-infrared optical tomography imaging system, or frequency modulated continuous wave system configured to capture additional images of the patient to supplement the images of the patient captured by the image recognition sensor.

In some embodiments, the image recognition sensor is in the form of two-spaced apart cameras configured to capture the images of the patient, and wherein the second computing device comprises a graphical user interface in the form of a head-mounted display device configured to generate two display images, each of the two display images being in front of a respective one of the right and left eyes of the remote physician or another observer at the remote site and corresponding to the images of the patient captured by the two-spaced apart cameras.

In some embodiments, the image recognition sensor is in the form of a three-dimensional multi-color meta-holography device configured to capture the images of the patient.

In some embodiments, the laser treatment system further comprises a photoacoustic system being operatively coupled to the first computing device, the photoacoustic system including an ultrasound transducer configured to detect acoustic waves that are generated as a result of the absorption of energy by the eye structure or the body surface such that the photoacoustic system is able to capture ultrasonic three-dimensional images of body structures beneath the skin of the patient, the body structures beneath the skin of the patient including bone structures of the patient.

In some embodiments, the treatment laser of the laser generation system is configured to provide photodynamic therapy to the patient by emitting light of a predetermined wavelength that is absorbed by tissue of a body portion of the patient to which a photosensitizer has been applied, the body portion of the patient comprising a cancerous tumor, and the photodynamic therapy configured to treat the cancerous tumor by killing the cells forming the cancerous tumor.

In some embodiments, the photosensitizer is applied to the tissue of a body portion of the patient comprising the cancerous tumor by using a plurality of nanoparticles, and wherein the light emitted by the treatment laser of the laser generation system is further absorbed by the nanoparticles.

In some embodiments, the predetermined wavelength of the light emitted by the treatment laser of the laser generation system is between approximately 380 nanometers and approximately 1550 nanometers.

In some embodiments, the laser treatment system further comprises a displaceable prism or mirror disposed in the path of the first treatment laser beam emitted by the treatment laser, the displaceable prism or mirror being operatively coupled to the first computing device so that the displaceable prism or mirror is capable of being selectively controlled by the first computing device based upon instructions received from the second computing device at the remote site from the remote physician, the displaceable prism or mirror configured to enable the first treatment laser beam to be applied to the tissue of the cancerous tumor of the patient in an oscillatory manner during the photodynamic therapy.

In some embodiments, the light emitted by the treatment laser of the laser generation system comprises ultraviolet light, and wherein the power of the treatment laser is between approximately 2 milliwatts and approximately 20 milliwatts.

In some embodiments, the digital image acquisition system of the laser-imaging apparatus is configured to acquire a two-dimensional image of the tissue of the cancerous tumor of the patient before, during, and after the photodynamic therapy; and the laser treatment system further comprises a photoacoustic system being operatively coupled to the first computing device, the photoacoustic system including an ultrasound transducer configured to detect acoustic waves that are generated as a result of the absorption of energy by the tissue of the cancerous tumor of the patient such that the photoacoustic system is able to capture ultrasonic three-dimensional images of the tissue of the cancerous tumor of the patient before, during, and after the photodynamic therapy.

In some embodiments, the photoacoustic system is further configured to determine a temperature of the tissue of the cancerous tumor of the patient subjected to laser energy from the first coagulation laser beam, the photoacoustic system further being configured to control the laser generation system by maintaining the laser energy of the first treatment laser beam at a predetermined energy level so as to prevent exceeding a predetermined threshold temperature during the photodynamic therapy.

In yet another embodiment, the laser treatment system includes:

a local control system disposed at a first location and a central control system disposed at a remote site, the remote site being at a second location, the local control system being operatively coupled to the central control system by means of a computer network;

the local control system including a laser generation device, a first computing device with a first processor, a local control module, and a dynamic imaging system;

the laser generation device including a treatment laser configured to generate and transmit a treatment laser beam to a treatment location on or in the patient;

the central control system including a second computing device with a second processor and a remote control module;

the remote control module being configured to perform a laser treatment procedure on the treatment location on or in the patient in an actual control mode in which the treatment laser is configured to transmit the treatment laser beam to the treatment location so as to surgically alter the body of the patient in the treatment location; and the dynamic imaging system including an imaging device operatively coupled to the first computing device, the imaging device configured to capture images of a body portion of the patient over a predetermined duration of time so that a displacement of the body portion of the patient is capable of being tracked during the predetermined duration of time, the first computing device being programmed to determine the displacement of the body portion of the patient over the predetermined duration of time using the captured images, and to compare the displacement of the body portion of the patient over the predetermined duration of time to a reference displacement of the body portion of the patient acquired prior to the displacement so that dynamic changes in the body portion of the patient are capable of being assessed for the purpose of identifying the patient or evaluating physiological changes in the body portion.

In still another embodiment, the telemedicine system includes:

a local control system disposed at a first location and a central control system disposed at a remote site, the remote site being at a second location, the local control system being operatively coupled to the central control system by means of a computer network;

the local control system including a first computing device with a first processor, a local control module, and a dynamic imaging system;

the central control system including a second computing device with a second processor and a remote control module;

the dynamic imaging system including an imaging device operatively coupled to the first computing device, the imaging device configured to capture images of a body portion of the patient over a predetermined duration of time so that a displacement of the body portion of the patient is capable of being tracked during the predetermined duration of time, the first computing device being programmed to determine the displacement of the body portion of the patient over the predetermined duration of time using the captured images, and to compare the displacement of the body portion of the patient over the predetermined duration of time to a reference displacement of the body portion of the patient acquired prior to the displacement so that dynamic changes in the body portion of the patient are capable of being assessed for the purpose of identifying the patient or evaluating physiological changes in the body portion.

In yet another embodiment, the telemedicine system includes:

a local control system disposed at a first location and a central control system disposed at a remote site, the remote site being at a second location, the local control system being operatively coupled to the central control system by means of a computer network;

the local control system including a first computing device with a first processor, a local control module, and a facial recognition system;

the central control system including a second computing device with a second processor and a remote control module;

the facial recognition system including an imaging device operatively coupled to the first computing device, the imaging device configured to capture one or more images of a face of the patient, the first computing device being programmed to compare one or more first reference digital images of the face of the patient captured by the imaging device of facial recognition system at a first time to one or more second digital images of the face of the patient captured by the imaging device of the facial recognition system at a second subsequent time, and to determine if the one or more second digital images of the face of the patient substantially matches the one or more first reference digital images of the face of the patient.

In still another embodiment, the laser coagulation system includes:

a local control system disposed at a first location and a central control system disposed at a remote site, the remote site being at a second location, the local control system being operatively coupled to the central control system by means of a computer network;

at least a first laser-imaging system disposed at the first location, the laser-imaging system including a laser-imaging apparatus, a laser generation system, a first computing device with a first processor, and a local control module;

the laser-imaging apparatus including a digital image acquisition and storage system configured to take and store digital images of the eye structure or the body surface, the digital image acquisition and storage system further including means for transmitting digital images;

the laser generation system including an aiming laser configured to generate and transmit an aiming laser beam to the eye structure or the body surface, and a treatment laser configured to generate and transmit at least a first coagulation laser beam to the eye structure or the body surface, and means for controlling the digital image acquisition and storage system and the laser generation system;

the local control module including a local operation sub-module, a local operation and performance simulation sub-module, the local operation sub-module configured to acquire at least a first digitized image of the eye structure or the body surface from the digital image acquisition and storage system and transmit the first digitized image to the remote site, the local operation sub-module further configured to receive a target laser transmission area or areas and laser transmission parameters from a remote physician, and determine a treatment area or pattern of spots on the first digitized image for application of the first coagulation laser beam, the local operation sub-module additionally configured to perform a laser coagulation of the eye structure or the body surface under the remote physician's command in which the first coagulation laser beam is applied to the treatment area or each of the spots in the pattern, the local operation and performance simulation sub-module configured to facilitate the testing of the system prior to its operation in an actual control mode by replacing an actual eye structure or body surface of the subject with the first digitized image of the subject's eye structure or body surface;

the central control system being in communication with the laser-imaging apparatus, the central control system including a remote control module and a second computing device with a second processor configured to receive and process command signals from the remote physician and transmit the command signals to the local control module; and the remote control module including a remote operation sub-module configured to facilitate communications between the remote physician and the second processor of the second computing device, the remote operation sub-module, in association with the local operation and performance simulation sub-module, further configured to execute a virtual treatment of the eye structure or the body surface, perform a test surgical procedure, and perform a fully automated and continuous laser coagulation procedure over the entire area of the eye structure or the body surface in the actual control mode in which the treatment laser is configured to transmit the first coagulation laser beam to the eye structure or the body surface In yet another embodiment, the laser coagulation system includes:

a local control system disposed at a first location and a central control system disposed at a remote site, the remote site being at a second location;

at least a first laser-imaging system, the laser-imaging system including a laser-imaging apparatus, a first processor and a local control module;

the laser-imaging apparatus including a wide angle digital image acquisition and storage system configured to take and store digital images of the retina, the digital image acquisition and storage system including at least one retinal viewing camera that provides a field of view of the retina in a range between 160° and 200°, the digital image acquisition and storage system further including means for transmitting digital images;

a laser generation system configured to generate and transmit at least a first aiming laser beam and at least a first coagulation laser beam, and means for controlling the digital image acquisition and storage system and the laser generation system;

the local control module including a local operation sub-module, a local operation and performance simulation sub-module, and a local safety and verification sub-module, the local operation sub-module configured to acquire at least a first retinal image of the retina from the digital image acquisition and storage system and transmit the first retinal image to the remote site, the local operation sub-module further configured to receive a target laser transmission area and laser transmission parameters from a remote physician, and determine a pattern of spots on the first retinal image for application of the first coagulation laser beam, the local operation sub-module additionally configured to perform a scatter laser coagulation of the retina under the remote physician's command in which the first coagulation laser beam is applied to each of the spots in the pattern, acquire a plurality of post-procedure retinal images, and transmit the post-procedure retinal images to the remote site for evaluation and verification of treatment, the local operation and performance simulation sub-module configured to facilitate the testing of the system prior to its operation in an actual control mode by replacing an actual eye of the subject with a digitized fundus image of the subject's eye;

the central control system being in communication with the laser-imaging apparatus, and including a remote control module and a second processor configured to receive and process command signals from the remote physician and transmit the command signals to the local control module;

the remote control module including a remote operation sub-module configured to facilitate communications between the remote physician and the second processor, execute a virtual treatment of the retina, perform a test surgical procedure, and perform a fully automated and continuous laser coagulation procedure over the entire area of the retina in the actual control mode;

the remote control module further including a remote operation and performance simulation sub-module and a remote safety and verification sub-module, the remote operation and performance simulation sub-module configured to test performance parameters of the local operation module and perform a treatment simulation of the retina by the remote physician while simulating eye movement of the subject by displacing the digitized fundus image of the subject's eye in accordance with a plurality of random variables;

the local and remote safety and verification sub-modules including physical, logical and medical safety constraints for safe operation of the system; and wherein the system for laser coagulation of the retina is in the form of a non-contact system that does not require the use of a contact lens.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
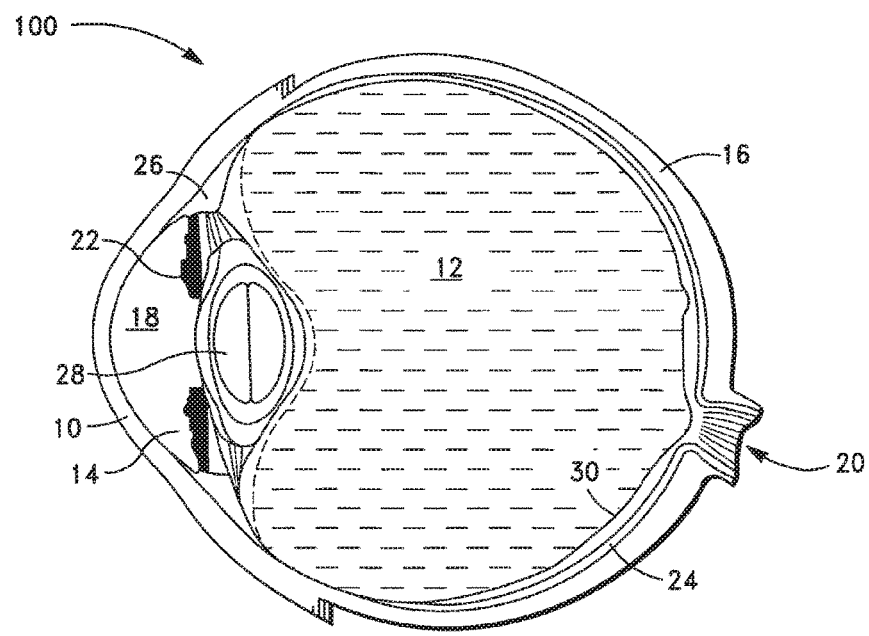
FIG. 1 is an illustration of a human eye showing the major structures thereof.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise. Thus, for example, reference to "a laser image" includes two or more such images and the like.

Definitions

The terms "eye disorder" and "eye disease" are used interchangeably herein and mean and include, without limitation, diabetic retinopathy, vascular occlusion, neovascularization, retinal detachment, neoplastic tissue, ischemic retina, retinopathy of prematurity and age related macular degeneration.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As will readily be appreciated by one having ordinary skill in the art, the present invention substantially reduces or eliminates the disadvantages and drawbacks associated with conventional systems and methods for coagulating eye structures to treat eye disorders.

In overview, the present disclosure is directed to laser imaging and coagulation apparatus, systems and methods that allow an eye specialist, e.g., an ophthalmologist or surgeon, to perform laser retinal surgical procedures, such as laser or tissue coagulation, with an integral laser imaging and coagulation apparatus disposed at a first (i.e. local) location from a control system disposed at a second (i.e. remote) location, e.g., a physician's office.

By the term "laser coagulation", as used herein, it is meant to mean and include, without limitation, selective absorbance of transmitted light energy (having a visible green wavelength) by hemoglobin in biological tissue and, hence, sealing of blood vessels in the tissue. In a preferred embodiment of the invention, the wavelength of the transmitted energy (referred to herein as a "treatment or coagulative laser beam") is in the range of approximately 400-1650 nm, more preferably, in the range of approximately 530-670 nm.

Although the present invention is directed to thermotherapy of biological tissue by laser energy, it is to be understood the invention is not limited to such form of energy. Indeed, as will readily be appreciated by one having ordinary skill in the art, the thermotherapy of biological tissue described herein, i.e. coagulation of selective eye structures, can also be achieved via the application of electromagnetic radiation, and radio frequency and ultrasound energy.

It is further to be understood that, although the biological tissue subject to the thermotherapy (i.e. coagulation), in accordance with the present invention, comprises the retina, the invention is not limited solely to thermotherapy of the retina. According to the invention, the thermotherapy of the present invention can be employed to coagulate any eye structure.

The laser-imaging apparatus, systems and methods of the invention, and laser energy transmitted thereby, can thus be employed to treat various eye disorders, including, without limitation, diabetic retinopathy, vascular occlusion, neovascularization, retinal detachment, neoplastic tissue, ischemic retina, retinopathy of prematurity and age related macular degeneration.

The laser-imaging apparatus, systems and methods of the invention, and laser energy transmitted thereby, can also be readily employed in refractive surgical procedures to, for example, perform corneal surface ablation using an eximer or femtosecond laser, LASIK procedures, and/or lid surface and surrounding tissue tightening using an infrared laser.

The laser-imaging apparatus, systems and methods of the invention, and laser energy transmitted thereby, can also be readily employed in cosmetic surgical procedures to, for example, remove skin lesions and perform skin resurfacing.

Before describing the invention in detail, the following brief description of the various anatomical features of the eye is provided, which will help in the understanding of the various features of the invention:

Referring to FIG. 1, the cornea 10, which is the transparent window that covers the front of the eye 100, is a lens-like structure that provides two-thirds of the focusing power of the eye.

The cornea 10 is slightly oval, having an average diameter of about 12 mm horizontally and 11 mm vertically. The central thickness of the cornea 10 is approximately 550 μm.

The sclera 16 is the white region of the eye, i.e. posterior five sixths of the globe. It is the tough, avascular, outer fibrous layer of the eye that forms a protective envelope. The sclera is mostly composed of dense collagen fibrils that are irregular in size and arrangement (as opposed to the cornea). The extraocular muscles insert into the sclera behind the limbus.

The sclera 16 can be subdivided into 3 layers: the episclera, sclera proper and lamina fusca. The episclera is the most external layer. It is a loose connective tissue adjacent to the periorbital fat and is well vascularized.

The sclera proper, also called tenon's capsule, is the layer that gives the eye 100 its toughness. The sclera proper is avascular and composed of dense type I and III collagen.

The lamina fusca is the inner aspect of the sclera 16. It is located adjacent to the choroid and contains thin collagen fibers and pigment cells.

The pars plana is a discrete area of the sclera 16. This area is a virtually concentric ring that is located between 2 mm and 4 mm away from the cornea 10.

The vitreous humor or vitreous 12 is the largest chamber of the eye 100 (i.e. ~4.5 ml). The vitreous 12 is a viscous transparent gel composed mostly of water. Unlike the fluid contained in the frontal parts of the eye (e.g., aqueous humor, discussed below), which are continuously replenished, the transparent gel in the vitreous chamber is stagnant.

As is well known in the art, the vitreous humor 12 also contains a random network of thin collagen fibers, mucopolysaccharides and hyaluronic acid.

The aqueous humor 14 occupies the anterior chamber 18 of the eye 100. The aqueous humor 14 has a volume of about 0.6 mL and provides nutrients to the cornea 10 and lens 28.

One of the most important functions of the aqueous humor 14 is to maintain IOP by the rate of its production and drainage.

The additional parts of the eye that are illustrated in FIG. 1 comprise the uvea, and structures thereof, lens 28 and retina 30.

The uvea refers to the pigmented layer of the eye 100 and is made up of three distinct structures: the iris 22, ciliary body, and choroid 24. The iris 22 is the annular skirt of tissue in the anterior chamber 18 that functions as an aperture. The pupil is the central opening in the iris 22.

The ciliary body is the 6 mm portion of uvea between the iris 22 and choroid 24. The ciliary body is attached to the sclera 16 at the scleral spur. It is composed of two zones: the anterior 2 mm pars plicata, which contains the ciliary muscle 26, vessels, and processes, and the posterior 4 mm pars plana.

The ciliary muscle 26 controls accommodation (focusing) of the lens 28, while the ciliary processes suspend the lens 28 (from small fibers, i.e. zonules) and produce the aqueous humor 14 (the fluid that fills the anterior and posterior chambers and maintains intraocular pressure).

The choroid 24 is the tissue disposed between the sclera 16 and retina 30. The choroid 24 is attached to the sclera 16 at the optic nerve 20 and scleral spur. This highly vascular tissue supplies nutrients to the retinal pigment epithelium (RPE) and outer retinal layers.

The layers of the choroid 24 (from inner to outer) include the Bruch's membrane, choriocapillaris and stroma. Bruch's membrane separates the RPE from the choroid 24 and is a permeable layer composed of the basement membrane of each, with collagen and elastic tissues in the middle.

The crystalline lens 28, located between the posterior chamber and the vitreous cavity, separates the anterior and posterior segments of the eye 100. Zonular fibers suspend the lens from the ciliary body and enable the ciliary muscle to focus the lens 28 by changing its shape.

The retina 30 is the delicate transparent light sensing inner layer of the eye 100. The retina 30 faces the vitreous and consists of two basic layers: the neural retina and retinal pigment epithelium. The neural retina is the inner layer. The retinal pigment epithelium is the outer layer that rests on Bruch's membrane and choroid 24.

As indicated above, conventional slit lamp systems, which are often employed to treat various eye disorders, such as diabetic retinopathy, require a contact lens to neutralize the refractive power of the cornea and to provide a variable field of view of the retina.

The length of time to perform a surgical procedure with a conventional slit lamp system is also presently in the range of 30 minutes to an hour. There is thus an increased percentage of probable error due to the laser photo-coagulation being controlled manually, i.e. by the physician's hand, and the potential eye movements from the patient during this extended period of time.

The present invention substantially reduces or eliminates the disadvantages and drawbacks associated with conventional slit lamp systems and associated methods. As discussed in detail herein, the laser-imaging apparatus include means for taking and storing digital images of the target eye structure(s), which can be retrieved on a monitor for diagnosis and defining the area of treatment. In some embodiments, the laser-imaging apparatus (and systems) of the invention thus include a retinal camera (e.g., Topcon, Zeiss, Kowa or preferably a wide angle viewing system having an elliptical mirror), which, in some embodiments, is modified with a wide-angle lens.

A wide field scanning laser-imaging apparatus, such as the laser opthalmoscope disclosed in U.S. Pat. No. 5,815,242, can also be employed to provide images of the fundus, particularly, the retina. The noted laser-imaging apparatus can also be readily modified for laser coagulation procedures in one or multiple health care applications or additional vision care offices.

According to the invention, the viewing light can comprise a white light from a flush light, laser source or one or more scanning lasers with compensatory wavelengths in the range of approximately 190 nm-10,000 nm, more preferably, in the range of approximately 400-1060 nm, to obtain a fundus photograph.

According to the invention, the retinal camera is connected to laser transmission means (or a laser system) that is adapted to generate and transmit laser energy that is sufficient to coagulate any desired portion of the retina using a monitor's touch screen.

In a preferred embodiment of the invention, the laser-imaging apparatus incorporates aiming and treatment laser generating and transmission means into an existing camera (e.g., Topcon, Zeiss, etc.) or a wide angle viewing system/camera, such as the laser opthalmoscope disclosed in U.S. Pat. No. 5,815,242. The laser-imaging apparatus also includes control means for controlling the aiming and treatment laser means, and the camera.

Preferably, the transmitted laser beam passes through the optical path of the viewing apparatus (or system) and is preferably reflected off of an elliptical mirror in the camera (in which the imaging light is focused toward the pupil or slightly behind the pupil), providing a field of view greater than approximately 200°.

Figure 2:
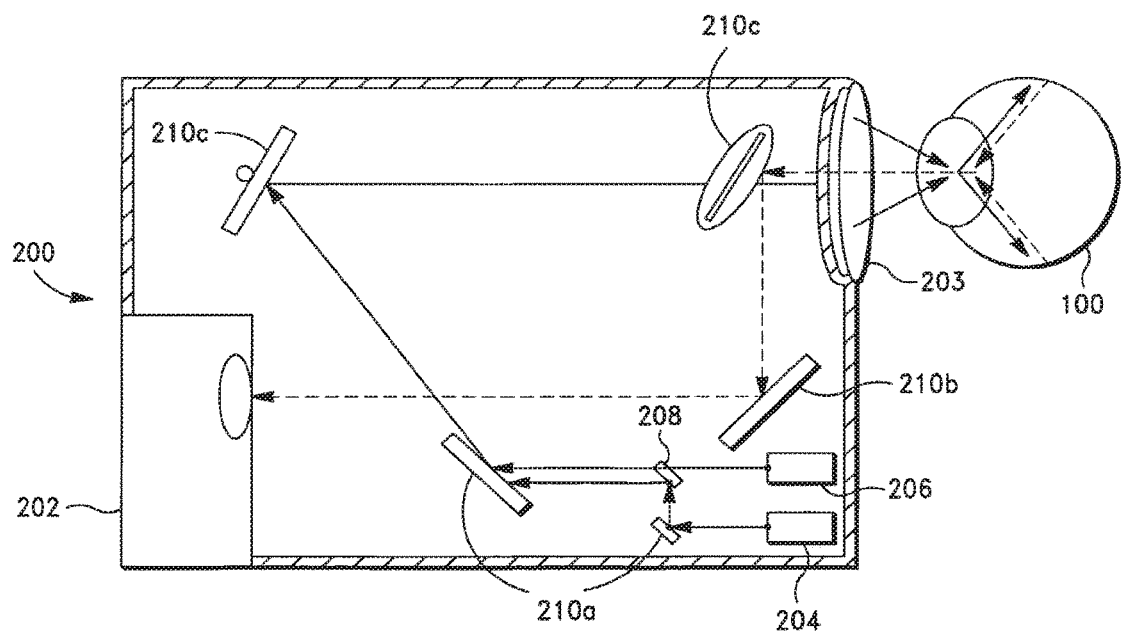
FIG. 2 is a schematic illustration of one embodiment of a laser-imaging apparatus, in accordance with the invention.

Referring now to FIG. 2, there is shown one embodiment of a laser-imaging apparatus of the invention. As illustrated in FIG. 2, the laser-imaging apparatus 200 includes a Topcon digital camera 202, scanning laser visualization means 204 and internal laser generation and transmission means (i.e. coagulation means) 206. The laser-imaging apparatus 200 further includes a refracting lens 203, at least one two-way mirror 208 and a plurality of appropriately positioned reflecting mirrors 201a-201c.

Figure 3:
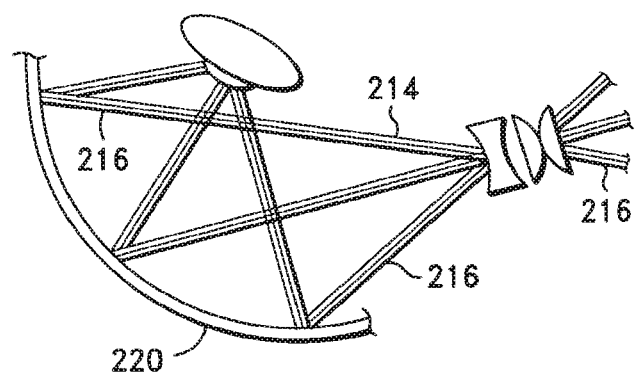
FIG. 3 is a schematic illustration of another embodiment of a laser-imaging apparatus, showing the elliptical mirror thereof, in accordance with the invention.

Referring now to FIG. 3, in an alternative embodiment, a wide angle camera equipped with an elliptical mirror 220 is employed. According to the invention, the illustrated wide angle camera provides an improved range of between approximately 150° and approximately 200°, inclusive, (or an improved range between 150° and 200°, inclusive) of the retina for optimal treatment.

In some embodiments, the concave, elliptical mirror 220 illustrated in FIG. 3 is configured to oscillate (or wobble) slightly in order to shift the focal point of the mirror 220 slightly from one side of the pupil to the other side, thereby permitting the scanning light (e.g., low coherent wavelengths, etc.) inside the eye to cover a larger peripheral field than possible without oscillation. An exemplary imaging system for imaging the central and peripheral retina, which employs such an oscillating concave mirror, is disclosed in Applicant's U.S. Pat. No. 8,070,289; which is incorporated by reference herein in its entirety.

In other embodiments, the concave, elliptical mirror 220 illustrated in FIG. 3 is stationary and is not configured to oscillate or wobble. It is also to be understood that the concave mirror 220 can be provided in the form of circular mirror, as well as an elliptical mirror.

FIG. 3 shows the path of the viewing/imaging scanning laser beams 214 as they are reflected and pass through the focal point of the mirror behind the pupil (Black) toward the retina. As illustrated in FIG. 3, the coagulative laser beam 216 preferably passes through the same path as the viewing/imaging beams 214.

In some embodiments of the invention, the laser-imaging apparatus of the invention also includes an optical coherence tomography (OCT) means.

Preferably, the rays reflected back from the retina pass through the same pathway and form a digital image that can be observed on the monitor.

According to the invention, the coagulative laser beam is also scanned over the retinal area via the same light path as used for the observation and documentation.

The integration of the aiming and treatment laser generating and transmission means with a camera requires the introduction of precision motorized optical fixtures. An opto-mechanical system having an integral control system is thus provided to control and/or position the target spot of the laser beam(s) in x and y directions within the eye. The system is designed and adapted to interface with joystick commands and/or computer/monitor touch screen commands, for local and remote control of the aiming and treatment (or coagulative) laser transmissions, respectively.

In some embodiments of the invention, the control means for positioning the laser transmissions (or beams) within the eye consists of two main components. The first component is adapted to move the beams in the x-direction. The second component is adapted to move the beams in the y-direction.

Preferably, movement in the y-direction is provided by a mirrored surface disposed in the optical path of the camera. This y-direction, motorized fixture provides precise movement of the mirrored surface, while still allowing diagnostic and treatment images to be seen through the retinal camera.

In some embodiments of the invention, producing the x-direction movement involves physically moving the laser unit; the movement of the laser being either translational or rotational. Various conventional means of motorized movement can also be employed to provide movement in the x-direction.

In a preferred embodiment, the laser-imaging apparatus is in communication with another remote system via the Internet®, whereby the laser-imaging apparatus can be controlled by a physician at the remote site (e.g., medical center).

According to the invention, location of laser energy or beam application can be from 5-200° of the retina. In some embodiments, location of laser energy application is preferably 30-200° of the retina.

In some embodiments of the invention, the transmitted coagulative laser energy (or beam(s)) has a wavelength in the range of approximately 400-1650 nm, more preferably, in the range of approximately 530-670 nm. The laser (or laser energy) can also be transmitted in a pulsed manner or continuously.

According to the invention, the laser spot size can be in the range of approximately 10 micron-1500 micron.

According to the invention, exposure time of the laser energy application can be in the range of approximately 1 femto-seconds to 1000 seconds.

In some embodiments of the invention, the laser-imaging apparatus 200 includes a photoacoustic system that can measure the temperature inside the eye tissue during and after laser scanning. A preferred photoacoustic system is disclosed in Applicant's U.S. Pat. No. 8,121,663; which is incorporated by reference herein in its entirety.

As set forth in detail in the '663 patent, the photoacoustic system is adapted to record the sonic waves that are generated by heating eye tissue, e.g. retina tissue. This provides precise information of the temperature generated as a result of the laser transmission, i.e. coagulative laser energy.

Advantageously, the photoacoustic system enables the temperature generated at the treatment site to be measured. As a result, the system is capable of balancing the energy of the laser system so that the coagulation is performed in a uniform fashion at the desired area, without such balancing one could have some lesions stronger than others depending on the degree of the pigmentation of the retina at the particular site (i.e., if the site absorbs more laser light).

Figure 4:
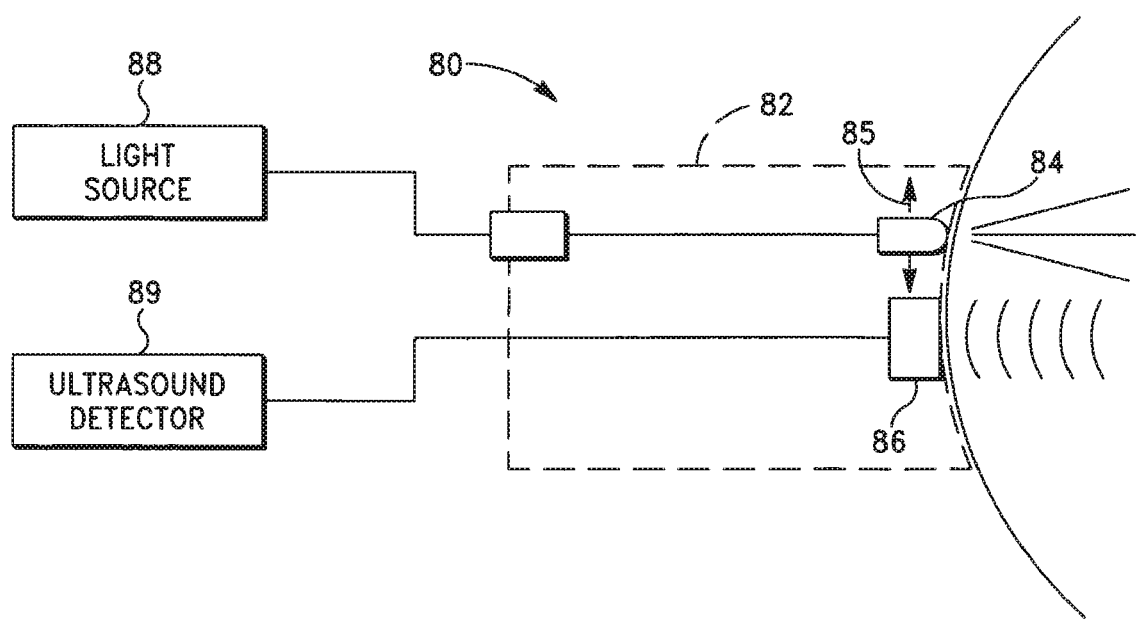
FIG. 4 is a schematic illustration of a photoacoustic system, in accordance with the invention.

Referring now to FIG. 4, there is shown one embodiment of a photoacoustic system 80. As illustrated in FIG. 4, the photoacoustic system 80 includes a laser source 88, an ultrasonic detector 89, and a probe module 82. The probe module 82 includes an objective lens structure 84, which is preferably coupled to the light source 88 via a fiber optic connection or other light transmitter. Alternatively, the light source can be incorporated into the probe module 82.

According to the invention, the light source 88 can comprise a laser, laser diode or superluminescent diode (SLD), as appropriate for generating the desired light wavelength and intensity. The light can also be delivered as pulses or as modulated radiation.

As further illustrated in FIG. 4, the probe module 82 further contains an ultrasound transducer 86 that is adapted to detect the photoacoustic waves that are generated as a result of the absorption of energy from the light emitted by the objective lens structure 84. The ultrasound transducer 86 is in contact with the eye 100 or an eyelid drawn over the eye.

As light is delivered as pulses or as modulated radiation, pulses or modulating acoustic signals are generated and returned to the ultrasound transducer 86 in probe module 82.

According to the invention, localization of the source of photoacoustic signals can be achieved in various manners. First, localization can be accomplished by directing the beam from objective lens structure 84 in specific directions, by moving that structure with micromechanical actuators, as shown diagrammatically at 85 in FIG. 4, thus targeting a particular line of points in the eye.

Furthermore, by suitable optics included in objective lens structure 84, the focal point of the emitted light may be moved within the eye to a desired point, such as a point along the retina vasculature, to selectively generate acoustic signals at that desired point. Because the eye is optically transmissive relative to soft tissue, beam focusing and beam directing are likely to be more accurately performed in the eye, than is the case is soft tissue elsewhere in the body.

To further assist in directionally capturing the photoacoustic signals generated within the eye, a directional transducer array can be used as transducer 86, to control the directionality of reception of ultrasonic energy, thus further localizing upon a desired source of thermoacoustic signals. Thus, by targeting the focal point of the illuminating light, and also directionally targeting the reception of ultrasonic signals by the transducer array, thermoacoustic signals from a particular location, such as along the retina, may be specifically targeted.

Overview of Laser-Imaging System

Figure 5:
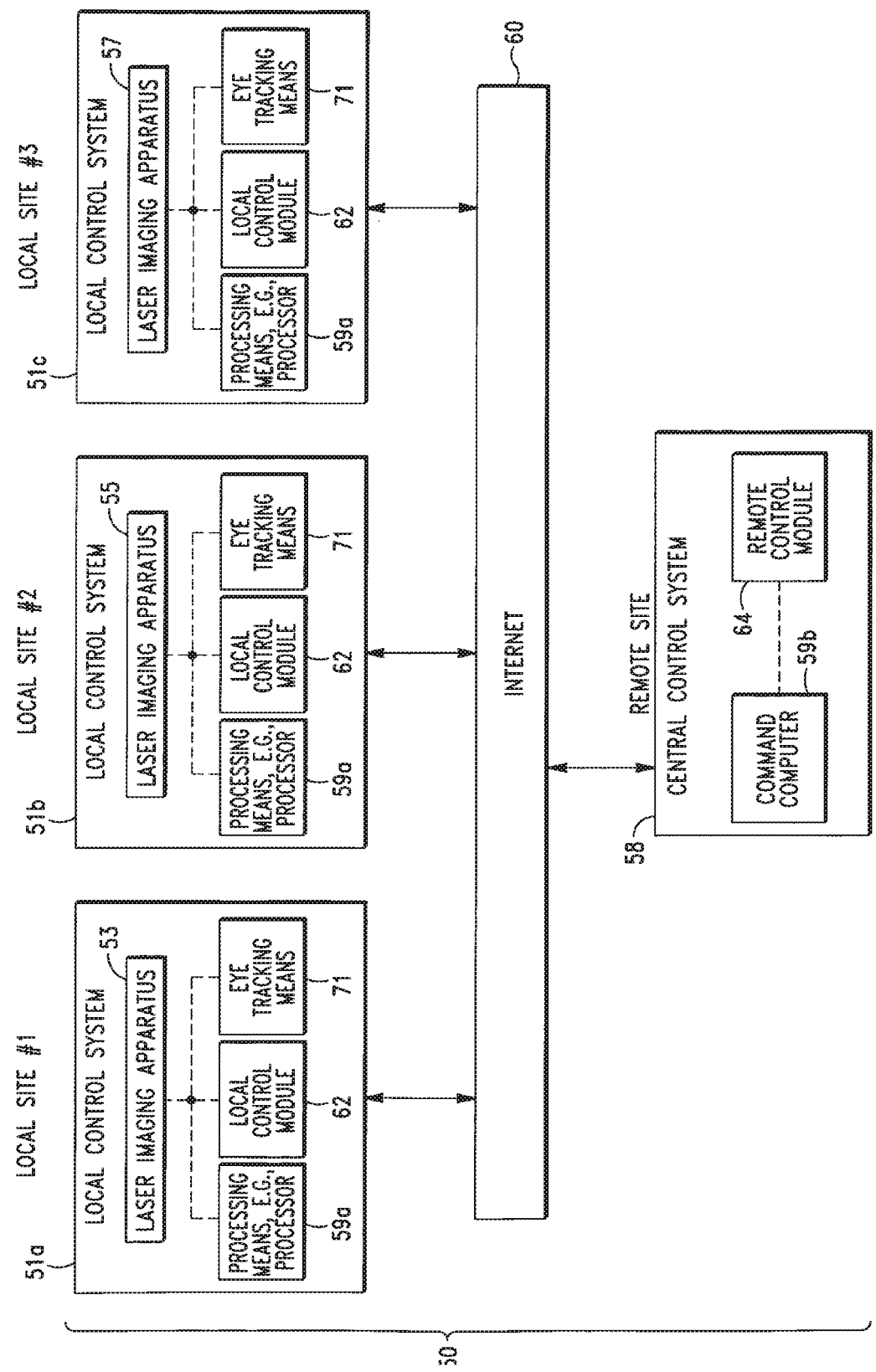
FIG. 5 is a schematic illustration of one embodiment of a laser-imaging system, in accordance with the invention.

Referring now to FIG. 5, there is shown a schematic diagram of a laser-imaging system 50, according to one embodiment of the invention. As illustrated in FIG. 5, the system 50 includes at least one, preferably, multiple local systems 52, 54, 56 disposed at local sites 51a, 51b, 51c; each system 52, 54, 56 including a laser-imaging apparatus (denoted "53", "55" and "57"), such as the apparatus 200 shown in FIG. 2. In a preferred embodiment of the invention, each laser-imaging apparatus 53, 55, 57 includes a photoacoustic system, such as system 80 discussed above.

Preferably, each laser-imaging apparatus 53, 55, 57 is preferably in communication with a local control module 62 and control-processing means 59a, such as a personal computer. Each of the modules described herein in conjunction with the embodiments of the laser-imaging systems 50, 50' may comprise one or more hardware components together with the requisite software to carry out the functionality performed thereby.

In some embodiments of the invention, at least the control-processing means 59a disposed at each local site 51a, 51b, 51c includes facial recognition means for identifying and/or verifying the identity of a subject or patient. Alternatively, in some embodiments, the control-processing means 59b disposed at the remote site 51d (discussed below) includes facial recognition means. In some embodiments both control-processing means 59a, 59b include facial recognition means.

In some embodiments of the invention, each local system 52, 54, 56 also includes eye tracking means 71 for measuring eye position(s) and movement. According to the invention, the eye tracking means 71 can be an integral component or feature of the laser-imaging apparatus 53, 55, 57 or a separate system or device.

Also disposed at each local site 51a, 51b, 51c during a laser procedure is a test subject or patient and a physician or technician.

As also illustrated in FIG. 5, the system 50 also includes a remote site 58 having a command computer 59b that is operatively connected to a remote control module 64. Also disposed at the remote site 58 during a laser procedure is a system operator (e.g., retinal surgeon).

As discussed in detail below, communication by and between the local sites 52, 54, 56 and the remote site 58 is preferably facilitated by the local and remote control modules 62, 64 and the Internet® 60.

In accordance with one embodiment of the invention, the sequence of interactions between the local sites 52, 54, 56 and remote site 58 comprises the following:

Fundus photograph is digitally transmitted to remote site;
Image is acquired by remote site and filed in the computer at remote site;
Eye is repositioned in front of the camera, fundus image is taken for pattern recognition and tracking, and transmitted to remote site, verified as matching previous, pre-existing image on file;
New image is selected and employed as simulator;
Spot size, power level, and time interval between each laser is chosen;
Tracking system (fail-safe) is checked;
Fundus laser treatment is performed in virtual mode to establish the desired laser coagulation; and
After choosing spot size and duration of laser application, power is adjusted to the lowest increment of energy that may or may not be able to create a response on the patient's eye. The power of the laser is incrementally increased until the test spot demonstrates the desired effect.

In a preferred embodiment, the optimum power and, hence, temperature required for a procedure is provided via the photoacoustic system. The photoacoustic system is further adapted to maintain the transmitted laser energy at a fixed, pre-selected level. This particularly results in a uniform coagulation of the retina.

Local and Remote Control Modules

Figure 6:
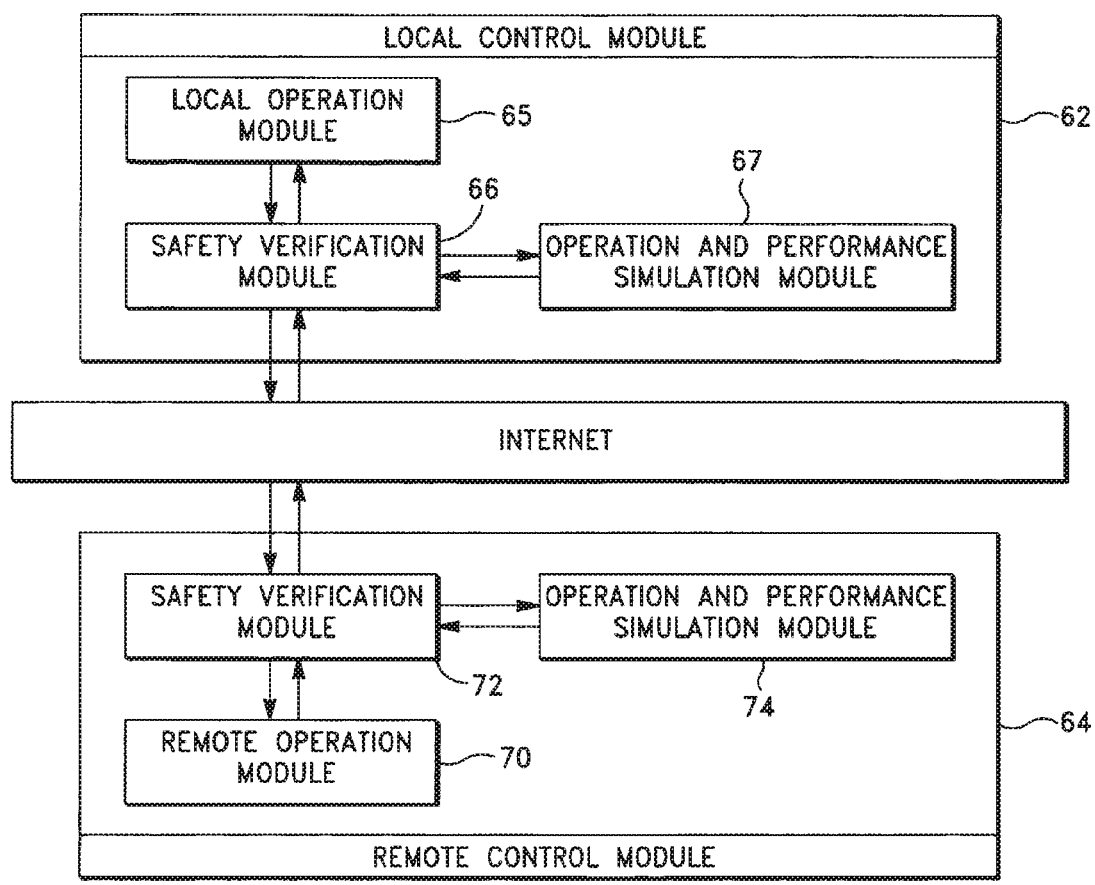
FIG. 6 is another schematic illustration of the laser-imaging system shown in FIG. 5, showing the local and remote modules thereof, in accordance with one embodiment of the invention.

Referring now to FIG. 6, there is shown a schematic diagram of a local control module 62 and a remote control module 64, according to one embodiment of the invention. As illustrated in FIG. 6, the local control module 62 preferably includes three sub-modules: an operation module 65, safety and verification module 66, and an operation and performance simulation module 67.

The remote control module 64 similarly includes three sub-modules: an operation module 70, safety and verification module 72, and an operation and performance simulation module 74.

Each of these sub-modules 65, 66, 67 is described below.

Local Operation Module

According to the invention, the local operation module 65 provides a local technician with an interface to a personal computer for data acquisition and eye treatment.

Figure 10:
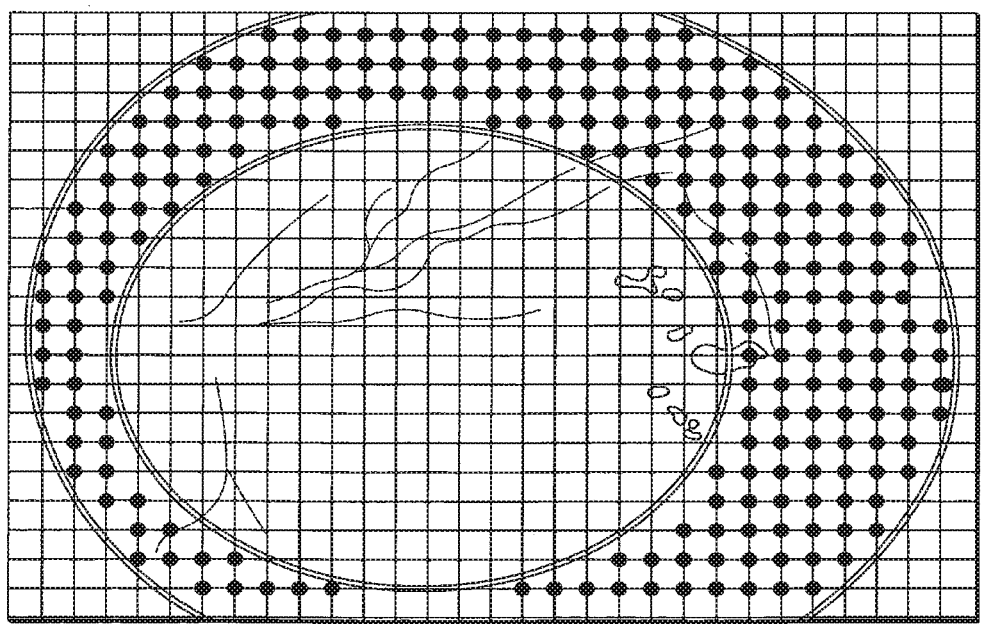
FIG. 10 is an illustration of a human retina, showing a generated grid map on the retina, in accordance with one embodiment of the invention.

According to the invention, the major tasks performed by the local operation module 65 include the following:

(1) acquiring a plurality (preferably, in the range of 5-7) standard fields of the fundus retinal images and transmission of the images to the remote site 58;

(2) receiving the oval area encompassing the focused region of the retina outlined by the remote physician (see FIGS. 5 and 7), as well as parameters for the spot size, power and duration of laser application;

(3) applying a snake algorithm (i.e. active contour algorithm) to extract the contours, calculating the corresponding areas between the contours, and partitioning the image into a grid map (see FIG. 10), as a function of the specified surgical area and corresponding parameters for laser application from the remote center. According to the invention, the resolution of the grid is adjusted according to the area between the contours, whereby the number of nodes between the contours (i.e. the black points between the two white contours) is large enough to generate in the range of approximately 700-1000 laser spots to ensure the surgery precision;

(4) performing the scatter laser coagulation under the remote doctor's command. During the process (which is performed in real-time), the Kalman filter and mean shift algorithm are preferably integrated to detect and estimate the test subject's eye movement: a) if the movement is under the given safety threshold, the laser system will be adjusted using a simple proportional-integral-derivative (PID) control algorithm based on the estimated motion so that it will be focused on the remotely specified spot within allowable surgical accuracy, and then the laser will be applied; b) if the estimated movement is beyond the specified safety threshold, the laser coagulation procedure will be terminated immediately and a warning message will be transmitted to the remote control module 64. Step (1), above, will also be repeated until a stop instruction is received from the remote physician; and (5) acquiring a plurality (preferably, in the range of 4-5) standard fields of fundus retinal images and transmitting the images to the remote site for evaluation and verification of treatment.

Local Operation and Performance Simulation Module

According to the invention, the local operation and performance simulation module 67 allows the physician (or technician) to test the entire system 50 (e.g., tracking and interruption functions in the local operation module 65; communications between local and remote sites; safety and verification modules 66, 72 at both remote and local sites) before the system 50 is run in an actual control mode.

In the simulation mode, the local simulation module 67 replaces the test subject (or patient), but all the other modules (e.g., modules at the remote site 70, 72, 74; safety and verification module 66 and local operation module 65 at the local site) preferably operate in exactly the same manner.

In one or more embodiments of the invention, the local operation and performance simulation module 67 is configured to test the tracking functions of the local operation module 65 by replacing the test subject with a digitized fundus image of him or her. The tracking system is tested using the digitized fundus image in place of the test subject by displacing the digitized fundus image in the X, Y, and O directions (see FIG. 9). The displacement of the digitized fundus image simulates the head and/or eye movement of the test subject that is experienced in the actual control mode. The laser is activated in the simulation mode, but is configured to turn off if the movement of the digitized fundus image exceeds a certain predetermined threshold so as to simulate the actual movement of the test subject exceeding a predetermined threshold.

Any rapid displacement beyond a certain predetermined threshold value or range of values (e.g., an orientation change exceeding 3-5 degrees) cannot be immediately compensated for by the tracking system. As a result, in such a situation, the local operation and performance simulation module 67 is configured to simulate the response of the tracking system to the detection of a displacement exceeding the threshold value or range by shutting down the laser of the laser coagulation system. In the simulation mode, the digitized fundus image can be slightly tilted or laterally displaced (e.g., moving the image on the screen of a visual display device or mechanically, by displacing the screen itself containing the image with a multi-dimensional actuator) to simulate the deactivation of the laser. In some embodiments, the tracking system is configured to follow a particular spot on the fundus image. When the spot being followed by the tracking system is rapidly tilted or displaced, the laser is shut down by the laser coagulation system. This simulated test is used to ensure that the tracking system is fully operational and functioning properly prior to the performance of the laser surgery (i.e., in the actual control mode).

While performing the simulation using a digitized fundus image of the eye is preferred, a physical model of an eye can also be used to perform the simulation carried out by the local operation and performance simulation module 67. For example, an artificial eye can be placed in front of the lens of the laser-imaging apparatus. In such an artificial eye, the retina of the eye is visible through the pupil thereof. In this configuration, the tracking system of the laser coagulation system is tested by slightly displacing the artificial eye in front of the lens of the laser-imaging apparatus (e.g., by using mechanical means, such as a multi-dimensional mechanical actuator) while the laser is activated, but is not firing any actual laser shots. When the detected displacement exceeds the threshold value or range, the tracking system is triggered so as to shut down the laser.

Remote Operations Module

According to the invention, the remote operation module 70 provides the physician with an interface to a personal computer. During a laser procedure, some of the important tasks that the physician will perform and are facilitated by the remote operation module) include: (1) screening via digitized photos, (2) outlining an oval area encompassing the center part of the retina (see FIGS. 5 and 7), (3) choosing the spot size and duration of laser application, (4) adjusting the power via single shots of test spots (preferably, with a duration in the range of approximately 0.001-0.1 seconds in approximately 0.06 intervals), (5) executing virtual treatment with the simulation module (see FIG. 6), (6) performing a test surgery, which involves the local operation and performance simulation module 67, and (7) performing the laser surgery in the actual control mode (and observing the surgery via a real-time video stream).

In one or more embodiments of the invention, the remote operation module 70 further comprises an electronic visual display device with touchscreen capabilities, which is operatively coupled to a personal computer or another digital appliance that has processing capabilities (e.g., a portable digital device, such as a mobile phone or smartphone, a laptop computing device, a palmtop computing device, a tablet computing device, etc.) As such, the laser-imaging apparatus (i.e., the fundus camera) is operatively coupled to the visual display device of the remote operation module 70 so that the digitized fundus (retinal) image of the patient is able to be displayed in detail.

The touchscreen system of the remote operation module 70 comprises a display screen that is sensitive to the touch of a finger or a type of stylus (e.g., a pen stylus). The touchscreen-type visual display device includes: (i) touch sensor in the form of a panel with a responsive surface, (ii) a hardware-based controller, and (iii) touchscreen software executed by the personal computer or other digital appliance. The touch sensor employed by the touchscreen may comprise resistive-type sensor(s), capacitive-type sensor(s), or surface acoustic wave sensor(s). Each of these sensor types has an electrical current passing through them, and touching the surface of the screen results in a consequential voltage change. The voltage change is indicative of the location of the touching. The controller is the hardware component that converts the voltage changes produced by the touch sensor into signals that the personal computer or other digital appliance can receive. The touchscreen software instructs the personal computer or other digital appliance as to what is occurring on the touchscreen and on the information delivered from the controller (i.e., what the user is touching and the location of his or her touch) so that the computer or digital appliance can respond accordingly.

Using the touchscreen visual display device, the physician (i.e., the ophthalmologist) can control the laser system with the touch of his or her finger or by using a stylus pen, etc. The visual display device also includes zoom capabilities in order to allow the physician to examine the details of the digitized fundus image (i.e., retinal image) if needed. The display recognizes and interprets the commands of the physician and communicates those commands to the personal computer that controls the laser generation system. As such, the laser generation system is controlled in accordance with the markings made by the physician on the touchscreen. In other words, the laser generation system is configured to carry out the laser treatment in accordance with the indicated markings on the touchscreen. When a typical procedure is being carried out by the physician, the digitized fundus (retinal) image of the patient is initially recalled on the visual display device. Because the fundus image is digitized, the physician is able to precisely sketch/draw on any area of the digitized fundus image so that he or she can indicate the location(s) where the laser pulses should be applied, and as required, the location(s) where the laser pulses should not be applied. For example, the area or areas where the laser pulses are to be applied are shaded and/or denoted using a first predetermined color (e.g., green, which signifies a laser is to be applied thereto), while the area or areas where laser pulses are not to be applied are shaded and/or denoted using a second predetermined color (e.g., red, which signifies that a laser is not to be applied in this region or regions). When the laser coagulation system is operating in either the simulation mode or the actual control mode, any invasion of the area shaded with the second predetermined color (i.e., the red area) will result in the immediate shutting down of the laser. Also, the area(s) where the laser pulses are to be applied can be separated from the rest of the retina by a continuous line of a predetermined color (e.g., a red line) so that there is a clear demarcation on the retinal image. The area or areas that are shaded and/or denoted using the second predetermined color (i.e., red, indicating that laser pulses are not to be applied thereto) may represent a part of the retina containing large retinal vessels, such as the region with the optic nerve head and the fovea, which are sensitive to laser damage and should not be coagulated (e.g., see FIG. 11). The area of the laser coagulation can be contiguous or separated. In general, the distance between each of the laser pulses can vary (e.g., in the range between 0.1 mm and 4.0 mm or between approximately 0.1 mm and approximately 4.0 mm, inclusive). The laser application can be a single pulse as long as it is indicated by a single colored dot (e.g., a green dot), or the quantity of the laser spots can range up to 2500 spots or more. The laser pulse duration can be in the range from one femtosecond to 4.0 seconds, inclusive (or in the range from approximately one femtosecond to approximately 4.0 seconds, inclusive). In other embodiments, the laser pulse duration can exceed 4.0 seconds. The energy level of each pulse can range from 0.01 femtojoule to one joule, inclusive (or between approximately 0.01 femtojoule to approximately one joule, inclusive), and more preferably, between 1 nanojoule to one joule, inclusive (or between approximately 1 nanojoule to approximately one joule, inclusive). The spot size of the laser varies between 0.0001 nanometers (nm) to 2 millimeters (mm), inclusive (or between approximately 0.0001 nm to approximately 2 mm, inclusive).

In addition, in one or more embodiments, the visual display device with touchscreen capabilities displays the degree of energy (e.g., number of laser pulses, laser spot size, laser power or laser energy level) and the number of laser spots applied for a given area. The visual display device also displays all the parameters that are needed or chosen by the operator in addition to the presentation of the virtual image of the test laser application. All of this information is recorded and stored in the computer. The remote laser apparatus, which is located at each of the local sites 51a, 51b, 51c (see FIG. 5), does not perform the laser coagulation if the prior test is not performed. Similarly, after the correction of any parameter of the laser, or any change in the area of application of the laser, a new test application is run to ensure the safety of the procedure.

Also, as a part of the fail safe mechanism of the system, any invasion of the area which is not be subjected to the laser (e.g., the area colored in red by the physician) results in the immediate shutting down of the laser so that the appropriate inspection can be performed and/or corrective actions can be taken. As such, the system has complete control over the area of laser application.

Figure 7:
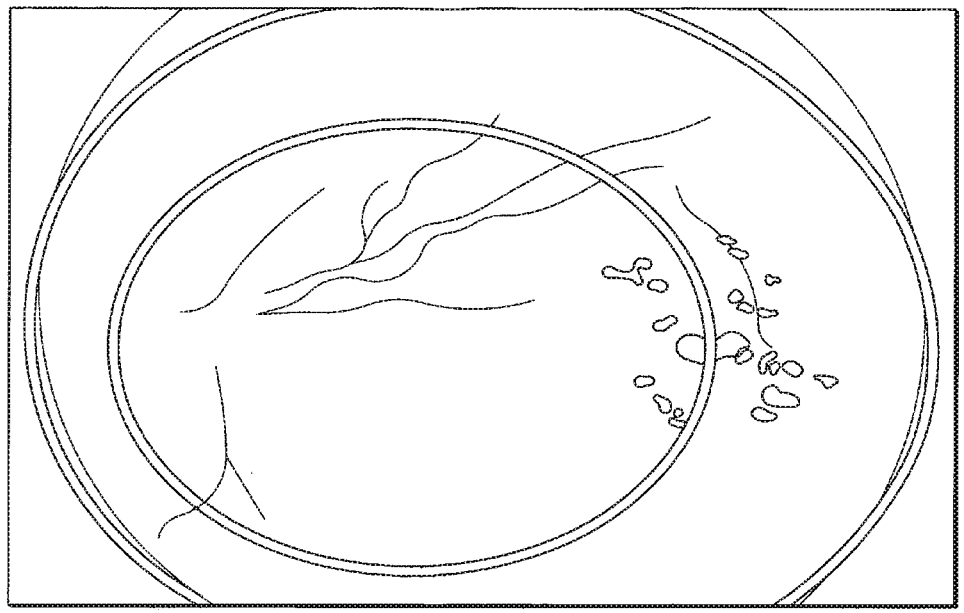
FIG. 7 is an illustration of a human retina, showing an oval area encompassing the target area on the retina for laser transmission, in accordance with one embodiment of the invention.
Figure 8:
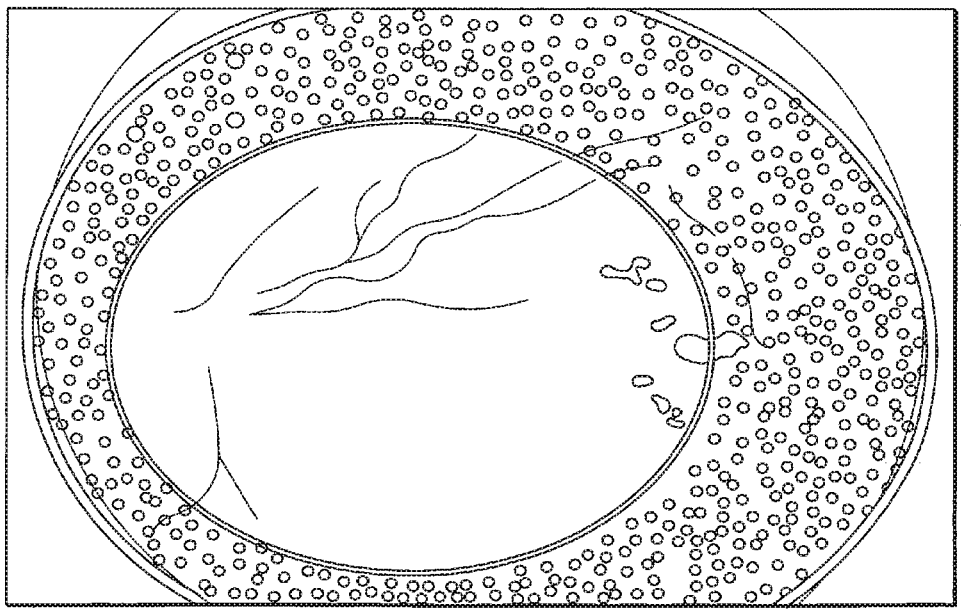
FIG. 8 is an illustration of a human retina, showing the distribution of laser spots resulting from a virtual treatment of the retina, in accordance with one embodiment of the invention.

Referring now to FIGS. 7 and 8, there are shown photographs of the retina, showing the outline of the oval target area (area bound by two oval lines) thereon for application of laser spots (FIG. 7) and the laser spots (in some embodiments, in the range of approximately 50-3000 laser spots) on the retina achieved via virtual treatment (see FIG. 8), as described below. In some embodiments, the physician can draw the oval lines in FIGS. 7 and 8 on the digitized fundus image by utilizing the touchscreen-type visual display device.

Figure 11:
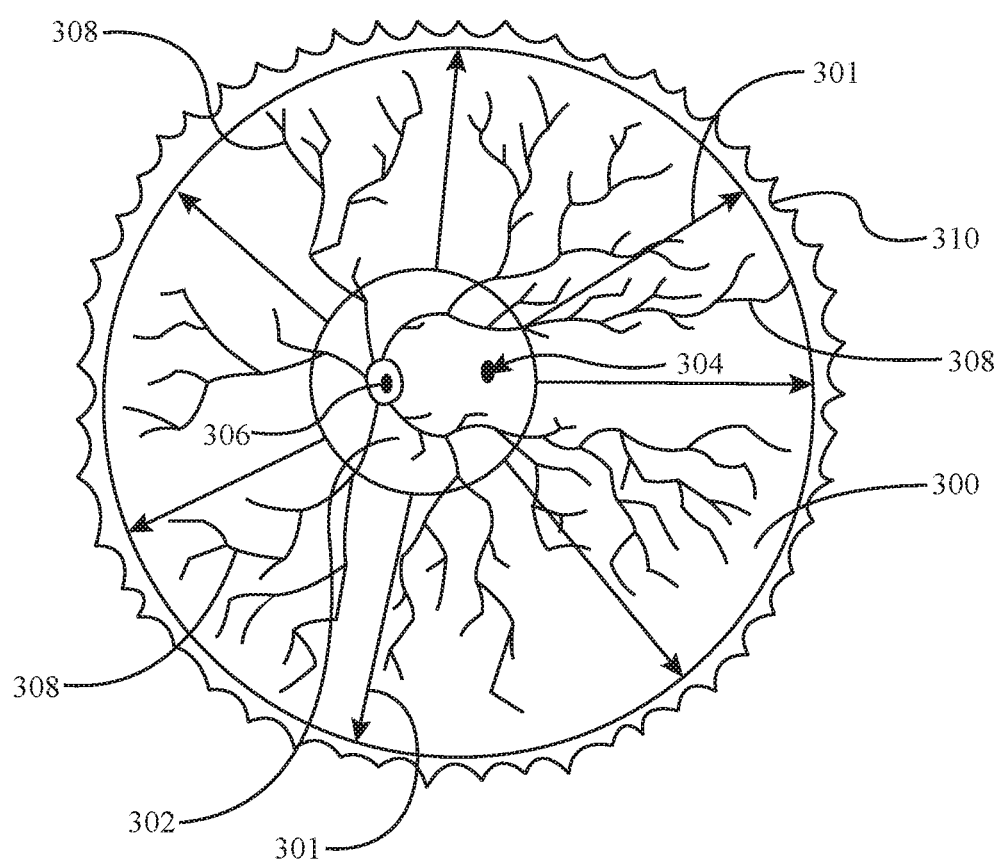
FIG. 11 is an illustration of a human retina, showing a large area of the fundus that is to be coagulated, in accordance with one embodiment of the invention.
Figure 12:
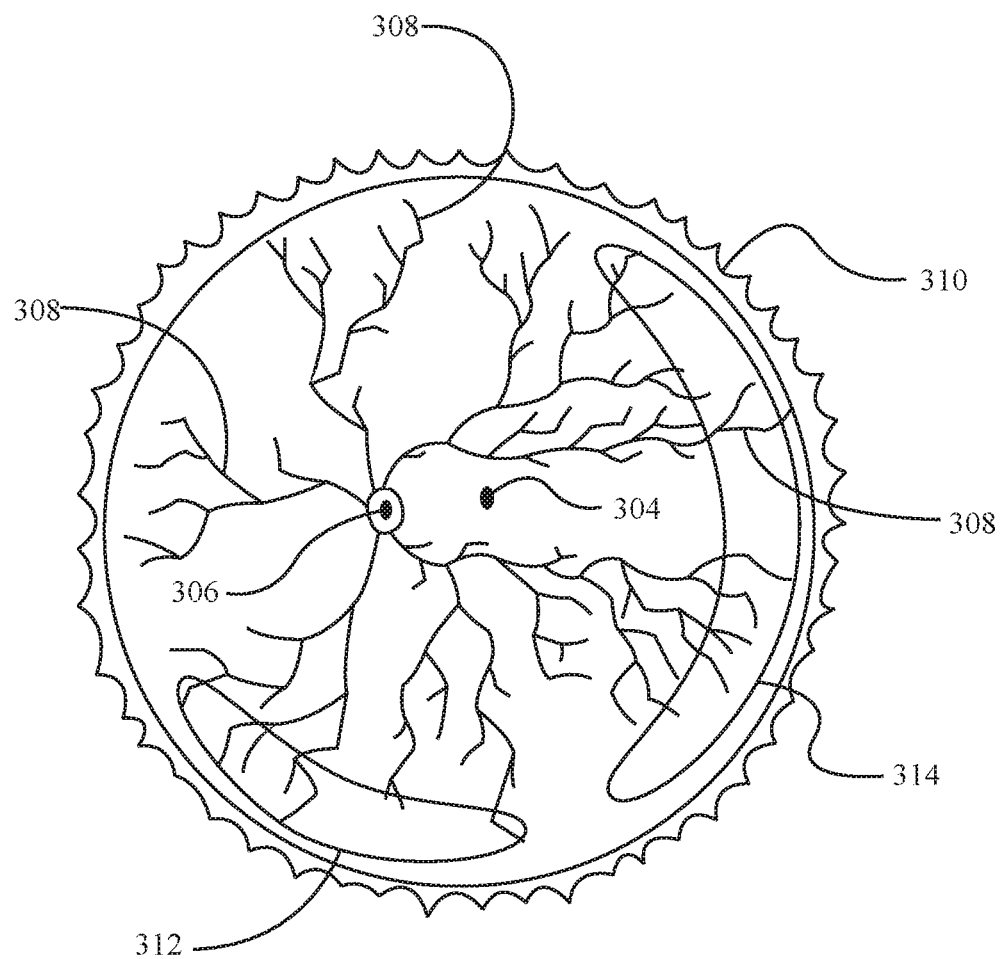
FIG. 12 is an illustration of a human retina, showing localized areas of the fundus that are to be coagulated, in accordance with one embodiment of the invention.
Figure 13:
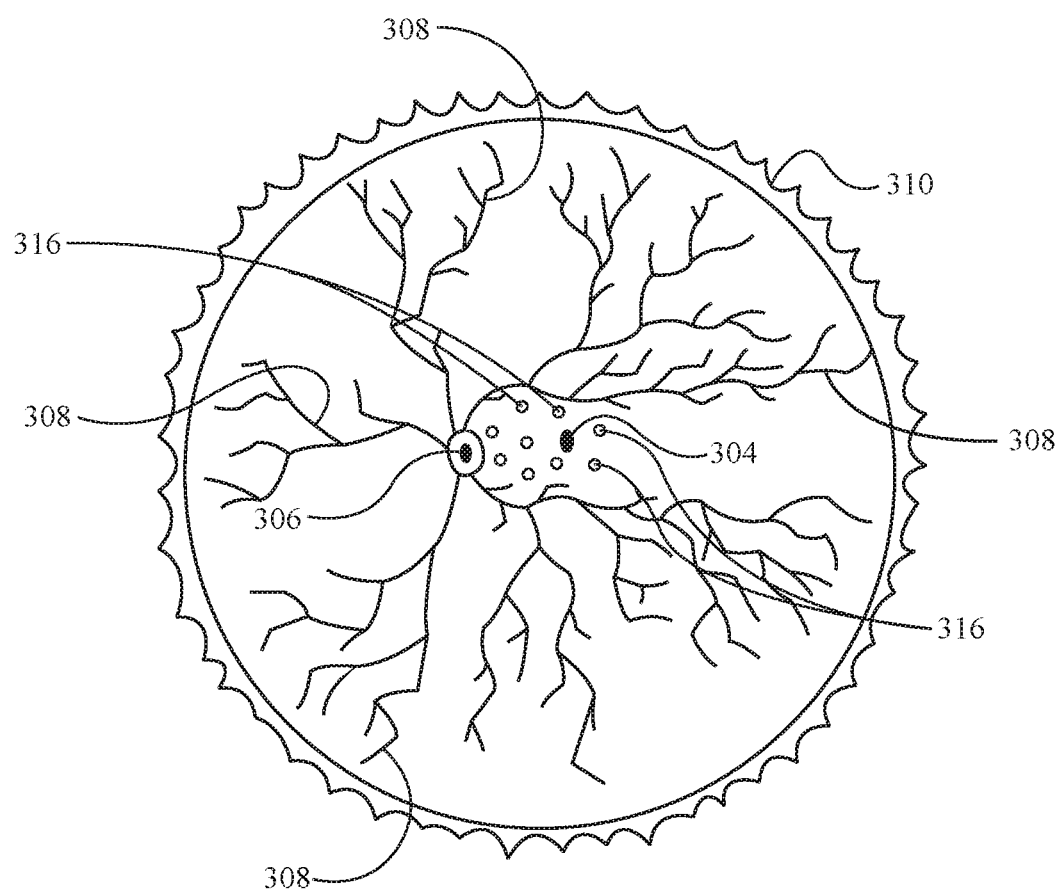
FIG. 13 is an illustration of a human retina, showing single, localized spots of the fundus that are to be coagulated, in accordance with one embodiment of the invention.
Figure 14:
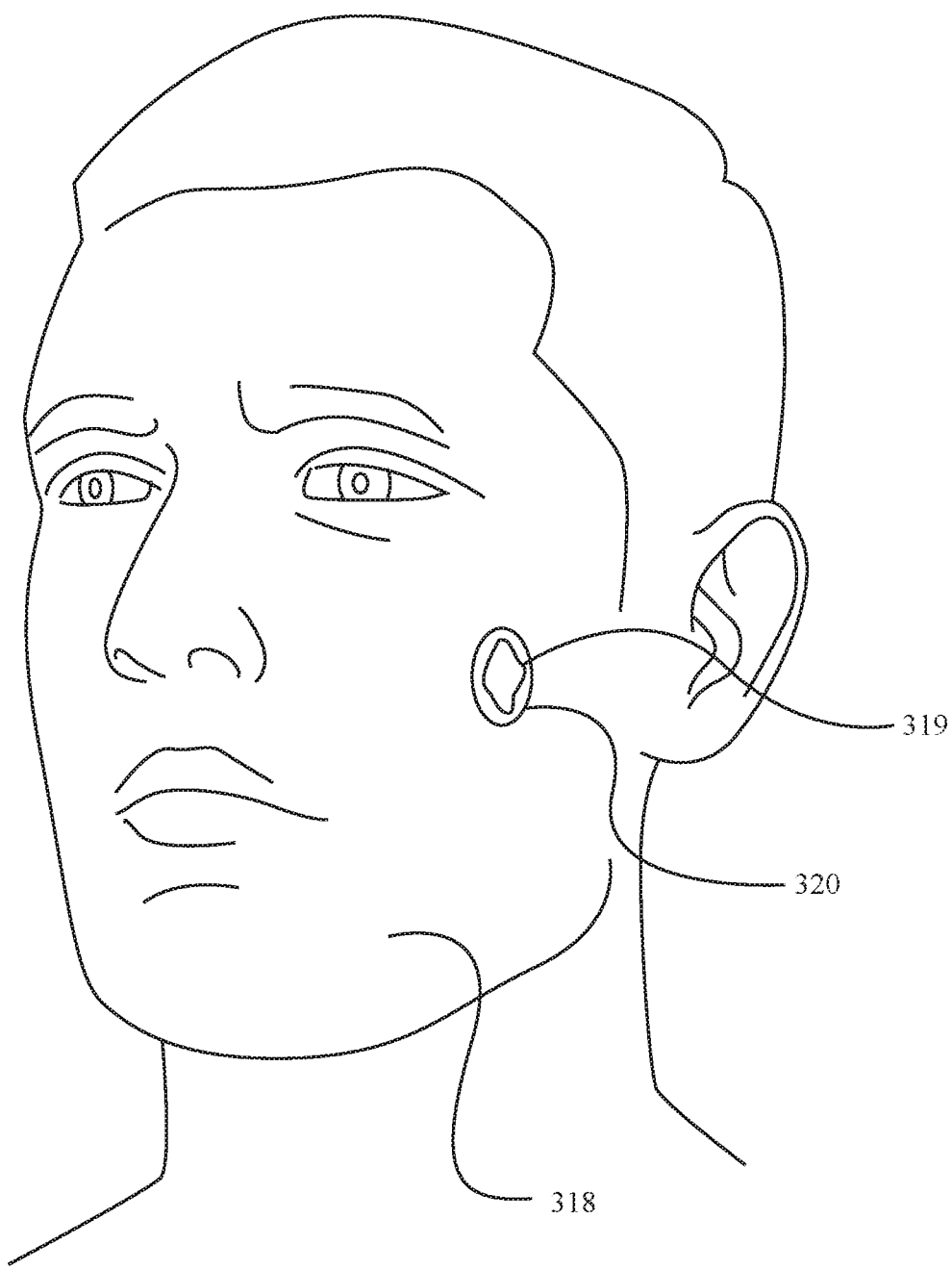
FIG. 14 is an illustration of a human face, showing an area of a skin lesion that is marked for laser application.

Now, turning to FIGS. 11-14, four (4) images showing exemplary areas of laser application on a patient are illustrated (e.g., as marked by a physician using the touchscreen-type visual display device). FIGS. 11-13 depict laser application areas in the retina, which have been indicated on the fundus (retinal) image of a patient, while FIG. 14 depicts a laser application area on the skin surface of a patient. Specifically, in FIG. 11, it can be seen that the annular area 300 (or donut-shaped area 300) with diagrammatic arrows 301 has been marked for laser application (e.g., by using a green color), while the central circular area 302 has been marked for no laser application thereto (e.g., by using a red color). As described above, the fovea 304 and the optic nerve head 306, which are located in the central circular area 302, are highly sensitive to laser damage, and thus, should not be coagulated. As shown in FIG. 11, the retinal area has a plurality of blood vessels 308 disposed throughout; the retinal area is surrounded by the ora serrata 310 (i.e., the serrated junction between the retina and the ciliary body). Next, turning to FIG. 12, two (2) localized areas 312, 314 are marked for laser application (e.g., by using a green color). As shown in FIG. 12, the localized areas 312, 314 are generally elongated, curved regions of the retina. Then, with reference to FIG. 13, it can be seen that a plurality of single localized spots 316 on the retina are marked for laser application (e.g., by using a green color). As illustrated in FIG. 13, the plurality of localized spots 316 are disposed in close proximity to the fovea 304 and the optic nerve head 306.

In addition, it is to be understood that the laser coagulation procedure described herein can also be applied to external surface areas on the body of a patient. For example, in FIG. 14, an area 320 of skin lesion 319 on a patient's face 318 is marked for laser application (e.g., by using a green color). As other examples, the laser coagulation system described herein could be used to treat the eye surface, the cornea, conjunctiva, eyelid, skin areas, or visible mucosa. As such, any part of the eye can be treated with the laser coagulation system described herein using the same laser-imaging apparatus described above, or a modified camera technology that is particularly suited for surface applications (e.g., a standard camera, such as those that are used in photography, or a microscope, etc.). Such a camera would be used to create images of the eye surface, the cornea, conjunctiva, eyelid, skin areas, or visible mucosa, etc.

Remote Operation and Performance Simulation Module

According to the invention, the remote operation and performance simulation module 74 allows a physician or technician to perform virtual treatment, which permits the physician to test the local operation module 65 (at a local site) in terms of its generation capability of the laser spots throughout the surgery area specified by the doctor (see FIG. 8). The algorithm used in this simulation module is similar to the one used by the local operation module 65.

After the physician (i.e., ophthalmologist) outlines the extent of the desired treatment area using the touchscreen visual display device of the remote operation module 70, he or she initiates the simulation process using the remote operation and performance simulation module 74. The treatment area outlined by the physician is filled virtually by the module 74 with dots (e.g., white dots), thereby covering the area and indicating the extent and the density of the laser spots that should occur on the retina and not on any other area.

Figure 9:
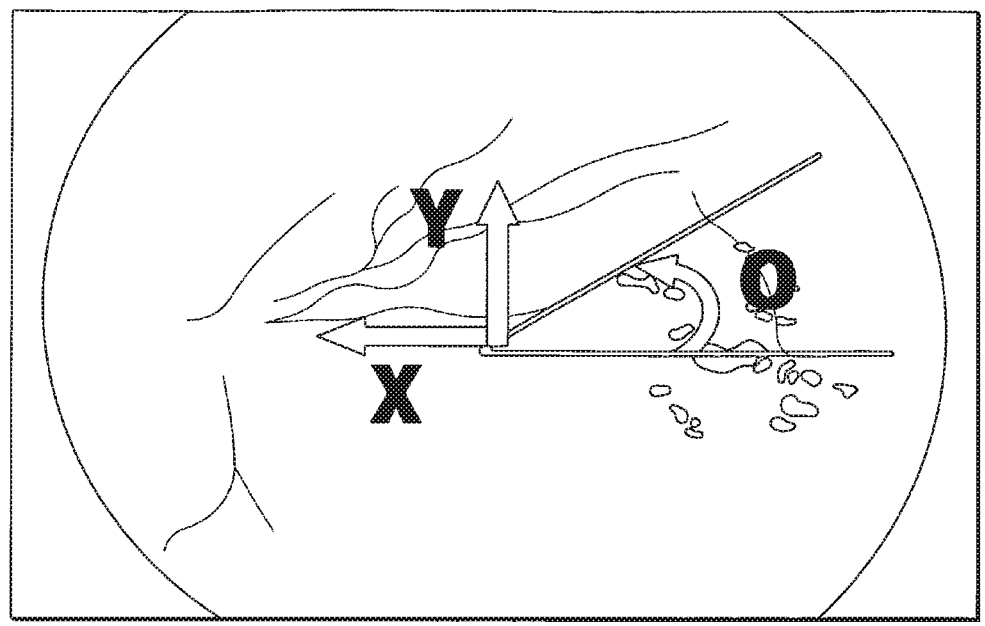
FIG. 9 is an illustration of a human retina, showing simulation variables associated with movement of the eye, in accordance with one embodiment of the invention.

Referring now to FIG. 9, in some embodiments, movement of the object (i.e. digitized fundus photograph) is simulated via three random variables; X, Y and O. The variables X and Y denote the displacement changes in the X and Y axes, respectively. The variable O denotes the orientation changes. In a preferred embodiment, the digitized fundus image is displaced electronically by the remote operation and performance simulation module 74 using the variables X, Y and O. The displacement of the digitized fundus image represents the movement of the retinal image of the patient prior to operating the laser coagulation system in the actual control mode.

In another embodiment, it is also possible to utilize mechanical means to displace a hardcopy of the fundus image (e.g., by using a multi-dimensional mechanical actuator that is operatively coupled to the hardcopy of the fundus photograph).

To this end, movement data from test subjects is first collected, from which best-fit statistical distributions (and variances) for the three random variables (X, Y, and O) are determined. According to the invention, a "goodness-of-fit" test can then be performed to test the validity of the distribution.

If a theoretical distribution (involving larger p-value in statistical sense) exists, it will then be employed. Otherwise, an empirical distribution will be constructed and employed.

According to the invention, the remote operation and performance simulation module 74 also allows the physician to test the local operation module 67 (at a local site) in terms of its generation capability of the laser spots without involving communications with the local control module 62.

Safety and Verification Modules

According to the invention, safety and verification modules 66, 72 exist both at the remote site 58 as well as each local site 52, 54, 56 to ensure safe and effective operation of the system 50. In a preferred embodiment of the invention, several constraints are preferably imposed into the system 50 (both hardware and software). In some embodiments, the constraints include (1) physical constraints, (2) logical constraints, and (3) medical constraints.

According to the invention, physical constraints ensure various parameters or values (e.g., therapy beam power) in the laser system 50 are within a permitted range. If any of the values are outside a permitted range, laser firing will be automatically locked and notification of the unacceptable value(s) is transmitted to the physician at the remote site, as well as the technician at the local site.

Logical constraints are employed to ensure that a correct sequence of operational tasks is performed. For example, if a physician at a remote site mistakenly commands 700-1000 laser spots of laser application to the fundus before simulating the laser application in a simulation mode, the system will not execute the command and transmits a warning message to the physician. In a preferred embodiment, Unified Modeling Language (UML) is incorporated into the system software and employed to specify the logical constraints.

The medical constraints involve monitoring of the fundus of the test subject(s) during the actual laser procedure operation. If it is detected that the laser energy effect on the fundus is different from what the physician expected or the laser energy is applied beyond the specified area, laser energy transmission is immediately terminated. Notification of the issue is also transmitted to the physician at the remote site, as well as the physician or technician at the local site.

As indicated above, in some embodiments of the invention, the system 50 also includes eye tracking and facial recognition means to ensure safe operation.

Laser-Imaging System with Image and Voice Recognition Capabilities

Figure 15:
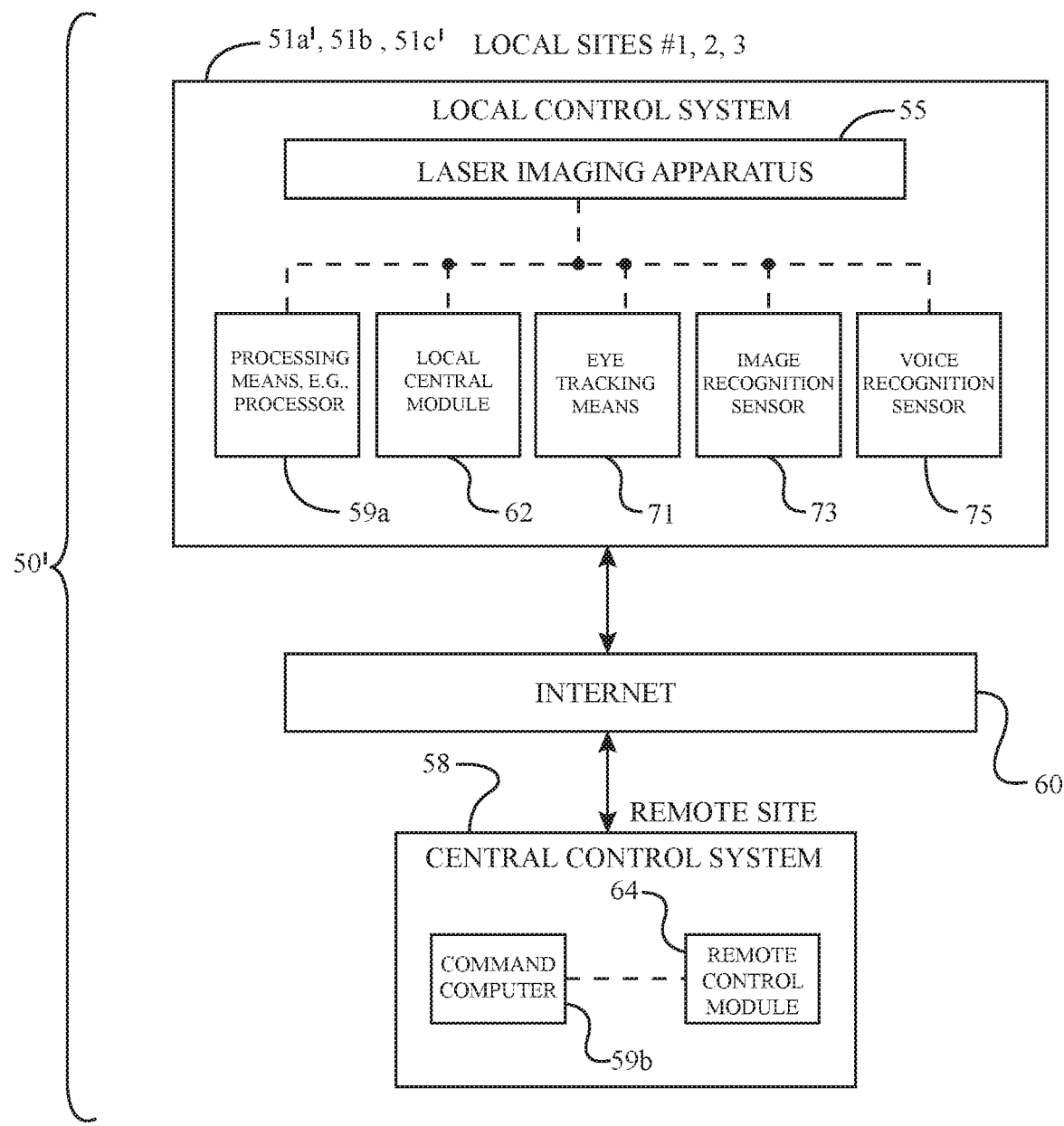
FIG. 15 is a schematic illustration of another embodiment of a laser-imaging system, in accordance with the invention, wherein the local control system of the laser-imaging system comprises image and voice recognition sensors.

Referring now to FIG. 15, there is shown a schematic diagram of a laser-imaging system 50', according to another embodiment of the invention. Referring to this figure, it can be seen that, in many respects, this embodiment of the laser-imaging system 50' is similar to the embodiment of the laser-imaging system 50 described above. Moreover, many elements are common to both such embodiments. For the sake of brevity, the elements that the laser-imaging system 50' has in common with the laser-imaging system 50 will only be briefly mentioned, if at all, because these components have already been explained in detail above. Furthermore, in the interest of clarity, these elements are denoted using the same reference characters that were used in the preceding embodiment.

As illustrated in FIG. 15, like the system 50 described above, the system 50' includes a plurality of local control systems disposed at local sites 51a', 51b', 51c'; each system including a laser-imaging apparatus 55, such as the apparatus 200 shown in FIG. 2. In a preferred embodiment of the invention, each laser-imaging apparatus 55 includes a photoacoustic system, such as system 80 discussed above.

Preferably, each laser-imaging apparatus 55 of the system 50' is preferably in communication with a local control module 62 and control-processing means 59a. In the illustrated embodiment, the control-processing means 59a may be embodied as a local personal computer or local computing device that is specially programmed to carry out all of the functionality that is described herein in conjunction with the local control systems of the laser-imaging system 50'.

In the illustrated embodiment of FIG. 15, each local control system also includes eye tracking means 71 for measuring eye position(s) and movement. According to the invention, the eye tracking means 71 can be an integral component or feature of the laser-imaging apparatus 55 or a separate system or device.

Referring again to FIG. 15, it can be seen that each local control system also includes an image recognition sensor 73 for capturing images of a subject or patient that may be used to identify and/or verify the identity of the subject or patient. Advantageously, the positive identification and verification of the identity of the subject or patient receiving treatment prevents surgical mistakes wherein the wrong subject or patient is treated. In addition, rather than identifying and/or verifying the identity of the subject or patient, the image recognition capabilities of the image recognition sensor 73 may also be used to identify and verify that a particular surgical procedure is being performed on the proper body portion of a subject or patient (e.g., to verify that a laser coagulation procedure is being performed on the proper one of the patient's eye or that a surgical procedure is being performed on the proper one of the patient's limbs). As will be described hereinafter, in a further embodiment, the image recognition sensor 73 or imaging device may be provided as part of a dynamic imaging system that is operatively coupled to the laser-imaging apparatus 55 of the laser treatment system. Also, as will be described hereinafter, the image recognition sensor 73 or imaging device may comprise a light field camera that is able to simultaneously record a two-dimensional image or three-dimensional image and metrically calibrated three-dimensional depth information of a scene in a single shot. In one or more embodiments, the image recognition sensor 73 may also comprise a multispectral camera that captures multispectral digital images over a wide range of frequencies of the electromagnetic spectrum (e.g., from visible light frequencies to infrared radiation frequencies). As such, because the camera is capable of operating using a wide range of different frequencies, the multispectral camera may be used as both a visible light camera (e.g., operating in the 450-750 nanometer range) and a thermographic camera for capturing images using infrared radiation (e.g., operating with wavelengths up to 14,000 nm (14 μm)).

In one or more embodiments, the image recognition sensor 73 of each local control system may be operatively connected to the local computing device, which forms the control-processing means 59a of the local control system. The local computing device may be specially programmed with image/pattern recognition software loaded thereon, and executed thereby for performing all of the functionality necessary to identify and verify a particular subject or patient, or to identify and verify a body portion of the particular subject or patient that is to be treated. Initially, the local computing device may be specially programmed to capture and store a first reference digital image of a body portion of the subject or patient so that the first reference digital image may be compared to a second digital image of the same body portion captured at a later time (i.e., just prior to the performance of the surgical procedure). Then, prior to the performance of the surgical procedure (e.g., a laser coagulation performed on the eye), the second digital image of the same body portion of the subject or patient is captured by the image sensor 73 (i.e., the multispectral camera) and the local computing device compares the second digital image of the body portion to the first reference digital image and determines if the second digital image of the body portion matches or substantially matches the first reference digital image. When the local computing device determines that the second digital image of the body portion of the subject or patient matches or substantially matches the first reference digital image, the local computing device is specially programmed to generate a matched image confirmation notification that is sent to the remote computing device at the remote site in order to inform the attending physician that the proper patient or body portion of the patient has been identified and verified. The matched image confirmation notification may also be delivered to the technician at the local site via the local computing device. Then, after the other safety checks of the system 50' have been performed, the surgical procedure is capable of being performed on the patient. Conversely, when the local computing device determines that the second digital image of the body portion of the subject or patient does not match or substantially match the first reference digital image, the local computing device is specially programmed to generate a non-matching image notification that is sent to the remote computing device at the remote site in order to inform the attending physician that the patient or body portion of the patient has not been properly identified and verified. The non-matching image notification may also be delivered to the technician at the local site via the local computing device. When the non-matching image notification is sent to the attending physician, the local computing device also disables the surgical equipment at the local site in order to prevent the procedure from being performed on the incorrect patient or the incorrect body portion of the patient (e.g., in a laser coagulation procedure, laser firing will be automatically locked out by the local computing device).

When the multispectral camera comprising the image recognition sensor 73 is used as a thermographic camera in the mid-infrared or infrared radiation wavelength range, the camera may be used to capture images of capillaries in the skin of the patient or subject. As such, the camera may sense the heat generated by the blood in these capillaries to identify the subject or patient, or a particular body portion of the subject or patient. A multispectral camera that is capable of both visible light photography and infrared pattern recognition takes into account psychological functions which are not achievable with a camera having only visible light capabilities (e.g., two or three different physiological functions of the patient may be taken into account with a multispectral camera). For example, prior to capturing the infrared image of a face of the subject or patient, the subject or patient may be instructed to frown so that wrinkles are made prominent in the face of the subject or patient. When the subject or patient frowns, skin capillaries become collapsed and folded, thereby reducing the blood flow through the collapsed and folded capillaries and the heat that is detected by the multispectral camera. As such, the local computing device may be specially programmed in the manner described above to verify the identity of the subject or patient using the image pattern created by this particular facial expression (i.e., frowning). Detectable wrinkles may also be created by instructing the patient to lift up his or her brow, by instructing the patient to laugh, or by instructing the patient to execute any other facial expression that creates wrinkles. As another example, the multispectral camera may be used to capture a body portion of the subject or patient (e.g., a portion of the patient's skin) that has previously undergone a surgical procedure whereby the structure of the body portion has been altered (e.g., the capillaries in a portion of the patient's skin that has been previously operated on will have a very unique pattern that is specific to the particular patient being verified). The scars created by the surgery create a very different, unique marker on the patient (e.g., scar tissue created by surgery does not have many capillaries). Because this specific pattern of skin capillaries that were surgically altered is extremely hard to artificially replicate, this means of verifying a patient's identity is very reliable and imposters are highly unlikely.

Figure 16:
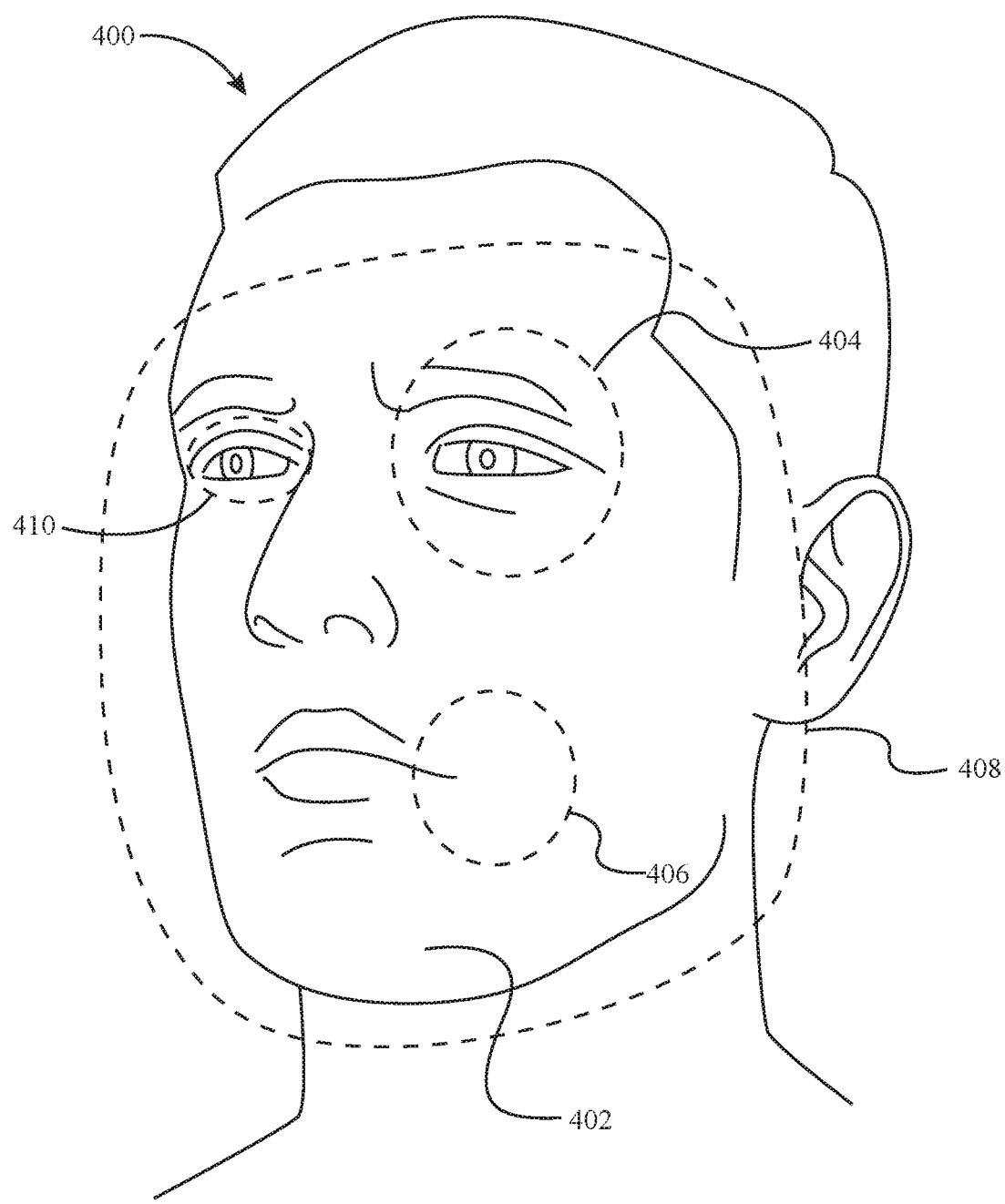
FIG. 16 is an illustration of a human face, showing exemplary areas of the human face that may be imaged so that the identity of a patient or the identity of a body portion of a patient may be verified.

Now, turning to FIG. 16, exemplary image capture areas on a face 402 of a patient 400 are shown. These are merely illustrative examples of some areas that may be imaged by the image recognition sensor 73 of the local control system. The first image capture area 404 in FIG. 16 is disposed around the left eye of the patient 400, and includes the left eye plus the area surrounding the left eye (e.g., so that facial features, such as wrinkles around the eye, may be used for patient identification and verification purposes in addition to the eye itself). The second image capture area 406 in FIG. 16 is disposed around the left corner of the mouth of the patient 400, and includes a portion of the mouth and the area proximate to the mouth (e.g., so that facial features, such as wrinkles around the mouth, may be used for patient identification and verification purposes). The third image capture area 408 in FIG. 16 is disposed around the entire face 402 of the patient 400 (e.g., so that a plurality of different facial features, such as wrinkles disposed throughout the face, may be used for patient identification and verification purposes). When the image of the face 402 of the patient 400 is captured by the image recognition sensor 73, the wrinkles in the face 402 remain dark. It is very difficult to circumvent the image recognition system by replicating wrinkles. The fourth image capture area 410 in FIG. 16 is disposed around the right eye of the patient 400 (e.g., so that the various structures of the right eye, such as the iris and retina, may be used for patient identification and verification purposes).

In addition to the face 402 of the patient 400, it is to be understood that other body surfaces may be imaged by the image recognition sensor 73 of the local control system as well. For example, any portion of the patient's body where the physician would like to apply a laser lesion under observation may be imaged by the image recognition sensor 73. Laser applications may vary from a nearly invisible laser lesion response from the tissue to an obvious burn of a given size or for tissue ablation and evaporation using any suitable laser, such as a gas laser, a solid-state laser, an ultraviolet laser, an infrared laser (i.e., a mid-infrared laser up to a $CO_2$ laser for surface tumor removal or for rejuvenation for cosmetic surgery), an excimer laser (i.e., for corneal surgery) with wavelengths of approximately 192 nm, and a $CO_2$ laser with wavelengths of approximately 10,000 nm (10 micron). Other suitable excimer lasers with various wavelengths may also be used (i.e., excimer lasers with other ultraviolet wavelengths). In addition, microwave or radiofrequency radiation may be applied to the patient from an appropriate unit to achieve the desired therapeutic result. The beam diameter may be varied or be focused to a diameter of one micron to five millimeters or more. The duration of each pulse can vary from one femtosecond to a continuous laser application depending on the need of the operator to achieve a particular result.

In a further embodiment, the laser-imaging system 50' may comprise an image recognition sensor 73 in the form of a holoscopic three-dimensional (3D) camera at the local site (i.e., to capture 3D images of the patient), and the graphical user interface of the command computer 59b at the remote site may be in the form of a multiview, three-dimensional (3D) display (i.e., so the physician can view the 3D images of the patient for identification purposes). In this further embodiment, changes in the physiological condition of the patient are induced (e.g., such as by having the patient smile, frown, etc.) while the changes are recorded by the 3D camera before, during, and after a medical procedure. Then, the results are displayed to the physician at the remote site using the multiview 3D display. Advantageously, the multiview 3D display permits a three-dimensional analysis of the physiological changes of the patient by the physician before and after a physiological change is induced. Also, the physician is able to analyze the trends of the physiological changes of the patient, such as augmentation or diminution of the physiological change. Also, the physical parameters associated with the physiological changes are able to be analyzed using a computer at the remote site (i.e., computer 59b), and compared with the initial existing data.

In this further embodiment, changes in the physiological condition may be induced in the patient after the patient responds to a question posed to him or her. In this case, the surface changes in the patent's face while answering the question may be recorded by the image recognition system and analyzed for the patient's recognition by comparing the recorded results to a previous session. Also, the patent's speech may be recorded while he or she is answering the question so that the speech patterns of the patient may be analyzed using the voice recognition sensor 75 described hereinafter.

Also, in this further embodiment, the multiview, three-dimensional (3D) display of the image recognition system may comprise a digital holographic display so as to allow the physician to perform a three-dimensional analysis of the changes in the physiological condition of the patient which are induced (e.g., such as by having the patient smile, frown, etc.). In this further embodiment, the digital holographic display may permit 3D display while maintaining the phase and amplitude data to reconstruct the wavefront through the use of a stereoscopic head mount display or console to reduce the sensory conflict of the eye during the convergence and accommodation and aid in a virtual reality display of the head, face, extremities, retina, vessels etc., for three dimensional analysis of the physiological changes before and after the physiological change is induced and the trends of the physiological changes. Also, the 3D display may be in the form of virtual reality glasses that are worn by the treating physician at the remote site.

Moreover, in this further embodiment, the digital holographic display of the image recognition system may comprise one or more thin holographic optical elements or one or more ultrathin optical elements for producing high-resolution 3D images, and may further comprise a multiview autostereoscopic 3D display to eliminate the need for the physician to wear special eye wear while performing the three-dimensional analysis of the induced changes in the physiological condition of the patient.

Furthermore, in this further embodiment, the multiview, three-dimensional (3D) display of the image recognition system may comprise a volumetric 3D display so as to present a 3D image on which each voxel is appropriately positioned, and reflects light to form a real image for the viewer (i.e., the physician) providing physiological and perceptual hints and spatial depth, and volume with high resolution of a structure while performing the three-dimensional analysis of the induced changes in the physiological condition of the patient.

Additionally, in this further embodiment, the holoscopic three-dimensional (3D) camera of the image recognition system may be configured to record tomographic images from a surface structure of the patient, such as the skin, as deep as the light can penetrate the tissue for three-dimensional analysis of the induced physiological changes and their trends. Also, the induced physiological changes of the patient may be additionally recorded during and after imaging using a near-infrared laser with Optical Coherence Tomography (OCT) or Near-Infrared optical Tomography (NIROT). When OCT is used for recording the changes, wide-angle Optical Coherence Tomography (OCT) may be utilized so that changes, such as the elevation or depression of a structure (e.g., the cheek, nose, tumor of the skin, etc.), is capable of being used during a two or three-dimensional analysis of the physiological changes and their trends. In addition, the induced physiological changes of the patient also may be recorded using a Frequency Modulated Continuous Wave (FMCW) system with ranging detection so as to obtain before, during, and after the physiological change is induced, 3D images of a surface which diffuses light with precision, i.e., under 10 micron speckle noise, while permitting the analysis of a variety of reflecting materials and tissue.

In another embodiment, the dynamic identity imaging involves analysis of a person's physical or psychological changes by presenting to a subject, a range of images and/or sounds or videos of incidences of relaxation or pleasure to extreme sadness or pain, while recording the person's body or the face with a hyperspectral camera, etc. to observe his or her response to the images/sound that can be analyzed in a dynamic format for physical or physiological, medical, psychology, psychiatric, or investigational, medical diagnosis, or security field, etc. or evaluation of a symptom of a disease before and after therapy, or to observe children in the playground, etc.

In yet a further embodiment, the image recognition sensor 73 of the laser-imaging system 50' may comprise two spaced-apart cameras that capture two standard images separated by 60 to 70 millimeters (mm) from each other (e.g., like two eyes of human, but as small as the camera on a smartphone). The two small cameras may be mounted over the photographic and imaging system of the laser-imaging system 50'. Two separate, but simultaneous images are taken with a white flash light generating a full spectrum of color (ultraviolet to infrared or infrared, etc.) using a diode laser. The patient can perform a similar action as that described above, such as smiling or frowning, which is then recorded by the two small cameras. The image is transmitted separately, but simultaneously via the Internet to the computer at the remote site (i.e., computer 59b), which may be located at the physician's or observer's office. This information is transmitted to a receiver and a small processor worn by the physician or observer, and converted to two different light pulses via a fiber optic to a small prismatic mirror located in front of each pupil of physician or observer, and projected into the eyes of the doctor's or observer's retina so that the right eye sees the images from the right camera and the left eye sees the images from the left camera. Both cameras may be working as a video system so that the doctor or observer sees a 3D video of the patient's face from the time that the patient sits in front of the cameras up to the time that the treatment laser of the laser-imaging system 50' is applied to the patient's face or to another part of the patient's body. Using the camera(s), it is also possible to create a 3D image of the retina or an object, such as face, located close to the camera(s). Also, in this further embodiment, an electronically controlled rapidly moving prism (e.g., oscillating at greater than 60 Hertz) or an electronically controlled rotatable lens (e.g., rotating back and forth by 10 to 30 degrees) in front of a single camera may be provided so as to create two different, but slightly angulated images from an outside object (e.g., face etc.) or from inside the eye of a patient. These separate images again are sent via the Internet to both eyes of the physician or an observer separately, but with the same frequency (greater than 60 Hertz). These images are capable of creating the sensation of a 3D display for the physician or observer who sees two different images with both eyes, but because of the frequency of the image presentation, the images are fused in the brain and seen as one three-dimensional image. In addition, the computer at the remote site (i.e., computer 59b) may also be configured to separately analyze each frame of the video so as to analyze changes that have occurred in the physiological condition of the patient by virtue of the induced changes (e.g., smiling, frowning, etc.) so that the patient's identity may be verified before any treatment is initiated.

In still a further embodiment, the image recognition system of the laser-imaging system 50' may comprise a three-dimensional (3D) multi-color meta-holography device for recording, analyzing and transmitting the data obtained during patient observation as a result of changes during and after a physiological action of the patent so as to distinguish newly computer-generated data from the previously stored data. This embodiment utilizes metasurface, meta-hologram imaging and 3D meta-holographic imaging that has been made possible by advancement in nanotechnology. In this embodiment, increased data capacity is achieved by the incorporation of single or different-sized plasmonic pixels into a metasurface, so as to create 3D multicolor meta-holography with reduced overlap between different colors. In this embodiment, the image recognition sensor 73 of the laser-imaging system 50' is in the form of a 3D multicolor meta-holographic imaging device and, in case of a discrepancy, the image recognition system is configured to shut down the laser treatment system automatically while the doctor or observer located in at the remote site simultaneously views the 3D multicolor meta-holographic images produced by the image recognition system.

In yet a further embodiment, the photoacoustic system 80 described above may be used for ultrasonic three-dimensional (3D) imaging of body structures beneath the skin of the patient, such as bone structures in the body of the patient. For example, the transducer array of the photoacoustic system 80 may be used for obtaining an ultrasonic 3D image of the bone structure of the nose of the patient while the head of patient is supported on a head support structure disposed in front of the photoacoustic system 80. Because the nose bone structure is unique to each patient, the imaged bone structure of the nose also may be for identification purposes in the manner described above for skin structures.

Turning again to FIG. 15, it can be seen that each local control system may further include a voice recognition sensor 75 for capturing the speech waveforms generated by the subject or patient so that the speech of the subject or patient may additionally be used to identify and/or verify the identity of the subject or patient. In one or more embodiments, the voice recognition sensor 75 may be used in conjunction with the image recognition sensor 73 described above to further verify that a surgical procedure is being performed on the correct subject or patient. In one or more embodiments, the voice recognition sensor 75 may comprise a microphone that captures the speech of the subject or patient over the entire speech frequency range of a human being (e.g., for a frequency range from 50 Hz to 5,000 Hz to encompass the typical frequency range for both males and females). As such, the syntax and sound pulses generated by the subject or patient are capable of being used by the local control system for verification and identification of the subject or patient prior to the surgical procedure being performed on him or her. In one or more embodiments, the voice recognition sensor 75 may be used as a second means of patient identity confirmation in order to confirm the identity of the patient that was previously verified by the image recognition sensor 73. In other words, the image recognition sensor 73 may comprises a first stage of patient identity confirmation, and the voice recognition sensor 75 may comprise a second stage of patient identity confirmation.

Similar to the image recognition sensor 73 described above, the voice recognition sensor 75 of each illustrative local control system may be operatively connected to the local computing device, which forms the control-processing means 59a of the local control system. The local computing device may be specially programmed with voice recognition software loaded thereon, and executed thereby for performing all of the functionality necessary to identify and verify a particular subject or patient that is to be treated. Initially, the local computing device may be specially programmed to capture and store a first reference speech waveform of the subject or patient so that the first reference speech waveform may be compared to a second speech waveform of the same patient or subject captured at a later time (i.e., just prior to the performance of the surgical procedure). That is, the patient or subject may be asked to say a particular word or plurality words that are captured by the voice recognition sensor 75 so that it can be used as the first reference speech waveform. Then, prior to the performance of the surgical procedure (e.g., a laser coagulation performed on the eye), the second speech waveform of the subject or patient is captured by the voice sensor 75 (i.e., the microphone records the same word or plurality words repeated by the subject or patient) and the local computing device compares the second speech waveform of the patient or subject to the first reference speech waveform and determines if the second speech waveform of the subject or patient matches or substantially matches the first reference speech waveform (i.e., by comparing the frequency content of the first and second speech waveforms). When the local computing device determines that the second speech waveform of the subject or patient matches or substantially matches the first reference speech waveform, the local computing device is specially programmed to generate a matched speech confirmation notification that is sent to the remote computing device at the remote site in order to inform the attending physician that the proper patient has been identified and verified. The matched speech confirmation notification may also be delivered to the technician at the local site via the local computing device. Then, after the other safety checks of the system 50' have been performed, the surgical procedure is capable of being performed on the patient. Conversely, when the local computing device determines that the second speech waveform of the subject or patient does not match or substantially match the first reference speech waveform, the local computing device is specially programmed to generate a non-matching speech notification that is sent to the remote computing device at the remote site in order to inform the attending physician that the patient has not been properly identified and verified. The non-matching speech notification may also be delivered to the technician at the local site via the local computing device. When the non-matching speech notification is sent to the attending physician, the local computing device also disables the surgical equipment at the local site in order to prevent the procedure from being performed on the incorrect patient (e.g., in a laser coagulation procedure, laser firing will be automatically locked out by the local computing device).

Similar to that described above for the system 50 of FIG. 5, the laser-imaging system 50' of FIG. 15 also includes a central control system 58 at a remote site having a command computer 59b that is operatively connected to a remote control module 64. Also disposed at the remote site 58 during a laser procedure is a system operator (e.g., retinal surgeon). In FIG. 15, it can be seen that the central control system 58 at the remote site, which includes the command computer 59b, is operatively connected to the plurality of local control systems disposed at local sites 51a', 51b', 51c' via a computer network that uses the Internet 60.

In one or more further embodiments, laser-imaging system 50' may further include a dynamic imaging system comprising an imaging device configured to capture images of a body portion of a person over a predetermined duration of time so that a displacement of the body portion of the person is capable of being tracked during the predetermined duration of time; and a data processing device (which may be the local computing device 59a) operatively coupled to the imaging device, the data processing device being specially programmed to determine the displacement of the body portion of the person over the predetermined duration of time using the captured images, and to compare the displacement of the body portion of the person over the predetermined duration of time to a reference displacement of the body portion of the person acquired prior to the displacement so that dynamic changes in the body portion of the person are capable of being assessed (e.g., by the local computing device 59a and the software algorithm executed thereby) for the purpose of identifying the person or evaluating physiological changes in the body portion. In particular, the local computing device 59a may execute a subtraction algorithm to demonstrate and project the specific areas of the body or face and ignore the rest of the data to clearly present weighted pixelated data for the future comparison of the same body or face and the trends of the area(s) of displacement. In these one or more further embodiments, at least two points of displacement may be used for the comparison of the subsequent displacement of the body portion of the person to the reference displacement and its recorded displacement trend(s).

In one or more embodiments, the subtraction algorithm or analysis performed by the local computing device 59a may subtract a second subsequent image from a first image in order to isolate the portion of the second image that changed as compared to the first image. In other words, the subtraction algorithm or analysis performed by the local computing device 59a removes or subtracts out the portion of the first and second images that is unchanged between the two images so as to isolate only the changed image portion. In one or more embodiments, the dynamic imaging procedure is a two-step process. During the first step, a first image of the patient is taken (e.g., the face of the patient) without requiring the patient to perform any particular task (e.g., smile or frown). During the second step, a second image of the patient is taken (e.g., the face of the patient) while requiring the patient to perform a particular task (e.g., smile or frown). Then, the first and second images are compared by the local computing device 59a using the subtraction algorithm or analysis. For example, if the patient is asked to smile or frown during the dynamic imaging procedure, only the mouth portion of the facial image of the patient is changed, thus the subtraction algorithm or analysis performed by the local computing device 59a eliminates the remainder of the facial image that is unchanged in order to enhance the processing speed of the image analysis process.

Because the second step of the two-step process dynamic imaging procedure described above requires the patient to perform an action when asked to do so by the clinician, the two-step dynamic imaging procedure results in the patient giving implicit consent to the dynamic imaging procedure (e.g., for identification purposes) because the person must voluntarily execute the task that is requested of him or her prior to the second image being taken. As such, consent issues that arise with conventional patient identification methods are averted by the dynamic imaging system described herein.

In one or more embodiments, the local computing device 59a is further programmed to determine a confidence level of the patient identification procedure performed by the dynamic imaging system herein. For example, the local computing device 59a may determine with 98% certainty that a subsequent image is of the same patient as that depicted in an initial reference image. The local computing device 59a may further be programmed to determine a percentage change between a first image and a second image (e.g., a percentage change in the pixels of a first tumor image and a second tumor image). The local computing device 59a may additionally be programmed to reconstruct an incomplete image of a patient based upon a previous image of the same patient (e.g., reconstruct an incomplete facial image).

In one or more further embodiments, the image recognition sensor 73 or imaging device of each local control system may be operatively connected to the local computing device, which forms the control-processing means 59a of the local control system. The local computing device may be specially programmed with image/pattern recognition software loaded thereon, and executed thereby for performing all of the functionality necessary to identify and verify a particular subject or patient, or to identify and verify a body portion of the particular subject or patient that is to be treated, the local computing device may be connected via the internet to the remote location where the operator or a doctor can use a helmet or gloves fitted with sensors or use the personal computer 59b with a mouse and software capable of creating an artificial environment where the patient or the subject is located (e.g. in a remote office as an augmented reality), so that the doctor or an observer can obtain all the data from the patient's body, face, or retina, etc. prior to or during or after dynamically induced physiological changes in the patient or subject, so that operator or the doctor can move the content of the three-dimensionally created image from one to another direction or zoom in or out or using presently available technology, such as Google® Glass or a heads-up display with a small screen in front of the eyes, etc. or as a wrap-around display screen as virtual reality to simulate the dynamic observation of the changes, the trend and subtraction of the before and after images by the computer algorithm to look objectively at the final product for the first time or compare it in the future session to another dynamic image similarly obtained from the patient or the subject to observe the differences or trends of the final subtracted data in the patient's or subject's image in the same environment where the patient is located, and thus creating an augmented reality or an artificial environment as virtual reality away from the patient or the subject and storing the information and data obtained after treatment of the patient in the cloud or another computer after encrypting the data for future reference.

In these one or more further embodiments, the image recognition sensor 73 or imaging device of each local control system may be operatively connected to the local computing device, which forms the control-processing means 59a of the local control system. The local computing device may be specially programmed with image/pattern recognition software loaded thereon, and executed thereby for performing all of the functionality necessary to identify and verify a particular subject or patient, or to identify and verify a body portion of the particular subject or patient that is to be treated. Initially, the local computing device may be specially programmed to capture and store reference dynamic information regarding a body portion of the subject or patient so that the reference dynamic information may be compared to dynamic information pertaining to the same body portion captured at a later time (i.e., just prior to the performance of the surgical procedure). Then, prior to the performance of the surgical procedure (e.g., a laser coagulation performed on the eye, or body surface, etc.), dynamic information pertaining to the same body portion of the subject or patient is captured by the image sensor 73 (i.e., the light field camera) and the local computing device compares the subsequent dynamic information pertaining to the body portion to the reference dynamic information and determines if the subsequent dynamic information of the body portion matches or substantially matches the reference dynamic information. In one or more embodiments, this information may relate to the position or size of any part of the body, extremities, or organ (e.g., as seen on an X-ray film, MRI, CT-scan, or gait changes by walking or particular habit of head position, hand, facial changes during speech, or observation of changes due to emotional changes, etc.). When the local computing device determines that the subsequent dynamic information pertaining to the body portion of the subject or patient matches or substantially matches the reference dynamic information, the local computing device is specially programmed to generate a matched identity confirmation notification or the trends of changes, etc. in a two-dimensional and/or three-dimensional manner that is sent to the remote computing device at the remote site in order to inform the attending physician or the receiving authority that the proper patient or body portion of the patient has been identified and verified or his or her response to stimuli. The matched identity confirmation notification may also be delivered to the technician at the local site via the local computing device. Then, after the other safety checks of the system 50' have been performed, the surgical procedure is capable of being performed on the patient. Conversely, when the local computing device determines that the subsequent dynamic information regarding the body portion of the subject or patient does not match or substantially match the reference dynamic information, the local computing device is specially programmed to generate a non-matching identity notification that is sent to the remote computing device at the remote site in order to inform the attending physician that the patient or body portion of the patient has not been properly identified and verified. The non-matching identity notification may also be delivered to the technician at the local site via the local computing device. When the non-matching identity notification is sent to the attending physician, the local computing device also disables the surgical equipment at the local site in order to prevent the procedure from being performed on the incorrect patient or the incorrect body portion of the patient (e.g., in a laser coagulation procedure, laser firing will be automatically locked out by the local computing device).

In these one or more further embodiments, turning again to FIG. 15, it can be seen that each local control system may further include a voice recognition sensor 75 for capturing the speech sound waves generated by the subject or patient so that the speech of the subject or patient may additionally be used to identify and/or verify the identity of the subject or patient, and his or her gender according to the frequencies of the sound waves and using, similar to the imaging system, a subtraction analysis of the sound initially and in the subsequent sessions. In one or more embodiments, the voice recognition sensor 75 may be used in conjunction with the image recognition sensor 73 or imaging device described above to further verify that a surgical procedure is being performed on the correct subject or patient. The voice recognition sensor may be simultaneously overlaid on the dynamic image recognition changes for facial or body recognition. Particularly, in one or more embodiments, the sound waves generated from the data acquired by the voice recognition sensor 75 may be superimposed on the displacement curve generated from the data acquired by the imaging device (e.g., the light field camera) so that both audial and visual attributes of the person may be taken into account for identification purposes, thereby making the identification of the person far more accurate. For example, as a person recites a series of vowels (i.e., AEIOU), the displacement of the lips of the person is recorded by the imaging device (e.g., the light field camera), while the voice recognition sensor 75 simultaneously records the voice of the person (e.g., the amplitude and/or frequency of the sound wave generated by the person). In one or more embodiments, the dynamic imaging system is used alone or simultaneously with voice overlay, thereby creating 2D or 3D images using multispectral light, which includes IR and mid IR, to measure time dependent changes for creation of a dynamic event made of voice and images or changes thereof. In one or more embodiments, a subtraction algorithm of the system is used to produce a clear subtracted wave complex from a person examined a first and second time, and to project the subtracted wave complex on the subtracted value of the person's image so as to evaluate a match or change, and present the changed values or their difference as compared to the sound waves received the first time by the voice recognition sensor 75. In one or more embodiments, the voice recognition sensor 75 may comprise a microphone that captures the speech of the subject or patient over the entire speech frequency range of a human being (e.g., for a frequency range from 50 Hz to 5,000 Hz to encompass the typical frequency range for both males and females). As such, the syntax and sound frequencies generated by the subject or patient are capable of being used by the local control system for verification and identification of the subject or patient prior to the surgical procedure being performed on him or her. In one or more embodiments, the voice recognition sensor 75 may be used as a second means of patient identity confirmation in order to confirm the identity of the patient that was previously verified by the image recognition sensor 73 or imaging device. In other words, the image recognition sensor 73 or imaging device may comprise a first stage of patient identity confirmation, and the voice recognition sensor 75 may comprise a second stage of patient identity confirmation.

Similar to the image recognition sensor 73 or imaging device described above, the voice recognition sensor 75 of each illustrative local control system may be operatively connected to the local computing device, which forms the control-processing means 59a of the local control system. The local computing device may be specially programmed with voice recognition software loaded thereon, and executed thereby for performing all of the functionality necessary to identify and verify a particular subject or patient that is to be treated. Initially, the local computing device may be specially programmed to capture and store a first reference speech waveform of the subject or patient so that the first reference speech waveform may be compared to a second speech waveform of the same patient or subject captured at a later time (i.e., just prior to the performance of the surgical procedure). That is, the patient or subject may be asked to say a particular word, a plurality of words, or a series of vowels (i.e., AEIOU) that are captured by the voice recognition sensor 75 so that it can be used as the first reference speech waveform. Then, prior to the performance of the surgical procedure (e.g., a laser coagulation performed on the eye or the body), the second speech waveform of the subject or patient is captured by the voice sensor 75 (i.e., the microphone records the same word, plurality of words, or series of vowels repeated by the subject or patient) and the local computing device compares the second speech waveform of the patient or subject to the first reference speech waveform and determines if the second speech waveform of the subject or patient matches or substantially matches the first reference speech waveform (i.e., by comparing the frequency content of the first and second speech sound waves). When the local computing device determines that the second speech waveform of the subject or patient matches or substantially matches the first reference speech waveform, the local computing device is specially programmed to generate a matched speech confirmation notification that is sent to the remote computing device at the remote site in order to inform the attending physician that the proper patient has been identified and verified. The matched speech confirmation notification or its discrepancies may also be delivered to the technician at the local site via the local computing device. Then, after the other safety checks of the system 50' have been performed, the surgical procedure is capable of being performed on the patient. Conversely, when the local computing device determines that the second speech waveform of the subject or patient does not match or substantially match the first reference speech waveform, the local computing device is specially programmed to generate a non-matching speech notification that is sent to the remote computing device at the remote site in order to inform the attending physician that the patient has not been properly identified and verified. The non-matching speech notification may also be delivered to the technician at the local site via the local computing device. When the non-matching speech notification is sent to the attending physician, the local computing device also disables the surgical equipment at the local site in order to prevent the procedure from being performed on the incorrect patient (e.g., in a laser coagulation procedure, laser firing will be automatically locked out by the local computing device). In one or more embodiments, the voice changes representing various emotional stages of the patients may be recorded for diagnosis or excessive stimuli, such as emotion or pain causing those changes, so that the power of a laser is accordingly adjusted, etc.

In one embodiment, the local computing device is further programmed to ask the patient a question so that the patient is able to respond to the question posed to him or her using natural language. That way, the system is not only able to analyze the physical surface attributes of the patient, but also analyze the sound of the patient's voice (i.e., by voice recognition recording), and communicate simultaneously with accessible existing data in a computer database to verify the identity of the patient.

In one embodiment, the time and the information obtained from the patient is recorded and stored for the future recall. In one embodiment, for a patient whose history does not yet exist in the computer database, the information will be recorded so as to be recognized by the system the next time the patient comes for reexamination.

In one embodiment, the system can access other computers searching for the existence of similar cases and photos of a surface lesion (e.g., X-ray, CT-scan, MRI, PET-scan, etc. of a lesion). The system may also be used as a telesystem accessing existing data in the published literature to assist the doctor with the diagnosis and further therapy recommendation for the patient.

In one embodiment, the computer system functions as an informational unit augmenting the knowledge of the doctor and assists in presenting him or her with similar recorded cases to assist in a better telemedicine diagnosis and management.

In one embodiment, the system may augment recognition of the patient by using additional information from a fingerprint, etc. For example, information regarding the tip of the patient's finger may be recorded (e.g., the blood circulation in the finger as well as images of the ridges and minutiae, etc. of the fingerprint) in a two-dimensional and/or three-dimensional manner so as to be used for identifying the patient in conjunction with the dynamic facial recognition of the person in a two-dimensional and/or three-dimensional manner. As such, the system advantageously provides augmented dynamic identification of the patient.

In one embodiment, the system works as an augmented intelligence assistant so as to assist a person in to making a proper decision (e.g., proper treatment of a cancer patient).

In one embodiment, the information obtained by the system is encrypted and transmitted so as to make it virtually impossible to be hacked by a third party.

In one embodiment, the system can differentiate between a human person and robot by its multispectral camera analysis recording the body's temperature versus the relatively cold body of a robot and the reflective properties of its body surface, etc.

In one embodiment, the system can differentiate between a person having a dark skin pigmentation and another person with lighter skin pigmentation by its multispectral camera analysis using the infrared (IR) spectrum of the camera to obtain images during the dynamic facial recognition that can see the skin capillaries under the skin because of selective penetration of IR wavelength of the light through the skin pigment and observe changes (e.g., collapse of capillaries at specific sites around the lips and in the eyebrows or forehead that fold and the collapse the capillaries inside the folds) during the dynamic facial recognition (e.g., with smiling or frowning), creating distinct landmarks that can be recognized by the subtraction of images using the software algorithm or observing additional landmarks, such as the teeth during smiling.

As mentioned above, in the illustrative embodiment, the image recognition sensor 73 or imaging device at the remote laser delivery site may be in the form of a digital light field photography (DLFP) camera with microlenses that capture the information about the direction of the incoming light rays and a photosensor array that is disposed behind the microlenses. A specially programmed data processing device (e.g., the local computing device 59a) is used to process the information obtained from the light field camera by converting it into two or three dimensional images, or the data is transmitted to a virtual reality system to be observed and recorded by the examiner or a doctor.

In one or more embodiments, the light field digital camera or digital light field photography (DIFLFP) camera comprises one or more fixed optical element(s) as the objective lens providing a fixed field of view for the camera. A series of microlenses are located at the focal point of the objective lens in a flat plane perpendicular to the axial rays of the objective lens. These microlenses separate the incoming rays of light entering the camera into individual small bundles. The individual small bundles of light are refracted on a series of light sensitive sensors that measure in hundreds of megapixels, which are located behind the plane of the microlenses, thereby converting the light energy into electrical signals. The electronically generated signals convey information regarding the direction of each light ray, view, and the intensity of each light ray to a processor or a computer. Each microlens has some overlapping view and perspective from the next one which can be retraced by an algorithm. Appropriate software and algorithms reconstruct computer-generated 2-3 D images from the objects not only in focus, but also those located in front or in the back of the object from 0.1 mm from the lens surface to infinity, which is being photographed by retracing the rays via the software and algorithm that modifies, or magnifies the image, as desired, while eliminating electronically the image aberrations, reflections, etc. As such, by using a digital camera, one can manipulate the image data by using an appropriate algorithm so as to create new in focus image(s) mathematically.

In one or more embodiments, the light sensitive sensors behind the lenslets of the camera record the incoming light and forward it as electrical signals to the camera's processor and act as an on/off switch for the camera's processor measuring the intensity of the light through its neuronal network and its algorithm to record changes in light intensity, while recording any motion or dynamic displacement of an object or part of an object in front of the camera in a nanosecond to a microsecond of time. The processor of the camera with its neuronal network algorithm processes the images as the retina and brain in a human being functions by finding the pattern in the data and its dynamic changes of the image and its trend over a very short period of time (e.g., nanosecond). The information is stored in the memory system of the camera's processor, as known in the art, as memory resistor (memristor) relating to electric charge and magnetic flux linkage, which can be retrieved immediately or later, and further analyzed by the known mathematical algorithms of the camera and can be used for many different applications, in addition to applications for 2-3 D dynamic image recognition as near or remote subjects recognition, incorporated in the remote laser delivery system described above.

In one or more embodiments, the light field camera may have either a tunable lens or a fluidic lens. If a tunable lens is utilized, the tunable lens may be in the form of a shape-changing polymer lens (e.g., an Optotune® lens), a liquid crystal lens, an electrically tunable lens (e.g., using electrowetting, such as a Varioptic® lens). Alternatively, a fluidic lens may be used in the light field camera.

In one or more embodiments, the light field camera may have a simple flexible transparent membrane that acts like a lens where its surface convexity or concavity can be controlled by a mechanically or electronically by compressing or decompressing a deformable lens by a non-deformable object, such as a magnetic plate or a piezoelectric system.

In one or more embodiments, the fluidic lens of the light field camera is a soft flexible lens which can be deformed electronically by applying pressure on the lens to increase or decrease the refractive power of the lens.

In one or more embodiments, the fluidic or tunable lens of the light field camera is combined with a solid lens, thereby creating a hybrid lens providing a minus or plus addition to the tunable lens.

In one or more embodiments, the fluidic light field camera shutter acts like a lid that covers the lens surface and is moved only up and down, or in horizontal direction to open or close the shutter, while in an open phase, the lens is exposed or is bulged outward permitting a wider field of view than the standard shutters provide.

In one or more embodiments, the tunable light field camera can be monocular or binocular camera and the images can be used in augmented reality (AR) or virtual reality (VR). The combination of two or more tunable field cameras can create 360 degrees in a 3-D format in non-dynamic and dynamic identity recognition.

In one or more embodiments, tunable light field camera with its software and algorithm can be used for dynamic recognition of an object, animate or inanimate, animal or human, where the dynamic changes can be observed in a 3-4 dimensional manner depending on which direction one likes to observe the subject or a person which now can be presented with AR/VR glasses or subtracted to provide information about the changes that has occurred during the dynamic observation.

In one or more embodiments, the tunable light field camera can be used for producing videos in augmented reality (AR) or virtual reality (VR) and can be used with appropriate AR/VR glasses while simplifying the observation of the image since the camera provides a focal point for any area which is being observed, thereby eliminating potentially the need for convergence while seeing the object monocularly or binocularly.

In one or more embodiments, the combination of a tunable light field camera and augmented reality (AR) or virtual reality (VR) can be used in the medical field to virtually recognize the growth of a lesion (e.g., a tumor) or the area of damage caused by a disease or trauma, etc. In this application, one will be able to see the structure in three and four dimensions during an invasive procedure, such as surgery, or a minimally invasive procedure through an endoscope, or a completely non-invasive procedure such as thermotherapy, using laser, focused ultrasound, or an alternating magnetic field along with antibody coated magnetic nanoparticles administered intravenously to seek the tumor cells and make them subsequently visible by CT-scan, ultrasound, or MRI tomography, or using the tunable light field camera and VR during the radiation therapy, laser therapy, or focused ultrasound, etc.

In one or more embodiments, the tunable light field camera and VR can be used by architects to see a building in 3D-4D format before it is built and its structural stability is examined with augmented reality (AR) glasses or virtual reality (VR) glasses.

In one or more embodiments, using the tunable light field camera along with augmented reality (AR) or virtual reality (VR), architects are able to see a building in 3-4D format before it is built and its structural stability is examined with AR/VR glasses (e.g., in AR/VR during an earthquake, hurricane, tornado, etc.) produced in vitro to evaluate stability of a high-rise building, bridge, airplane, or any other structure, etc. or any area that requires 3-D, 4-D, or 5-D observation and planning (e.g., airline pilots to see their surrounding area to avoid an aerial crash by another plane or collision with birds, etc.).

In one or more embodiments, the light field camera is used as a part of a dynamic facial recognition system for patient identification and verification, as described above. Advantageously, the tunable lens, when combined with the other components of the light field camera, offers precise focusing using the microlenses, nanosensors, and computer to analyze numerous focal points that can be reconstructed mathematically using specific algorithms implemented by the data processing device (i.e., the computer of the dynamic imaging system). Also, the dynamic imaging system may use the computer to verify or identify various changes that happen during the change in physiological function of a person's facial expression (e.g., smiling or frowning) as a computer-generated digital 2D or 3D image or video frame records the dynamic changes of a structure, such as a face, mouth, eyes etc., and the computer analyzes and compares the biometrics as a dynamic physiological fingerprint with existing data of the same image. The computer algorithm analyzes the changes in the relative position of a patient's face, matching points and directions, and compressing the data obtained during the process using dynamic recognition algorithms. One exemplary technique employed is the statistical comparison of the first obtained values with the second values in order to examine the variances using a number of means including multi-spectral light that looks at the various physiological changes of the face. Mathematical patterns of the digital images and statistical algorithms are capable of demonstrating that the images obtained initially and subsequently belong to the same person, etc. For example, the computer may compare the images using known techniques, such as elastic bunch graph matching, face recognition using a Fisherface algorithm, face recognition using dynamic link matching, etc. Also, these techniques may be employed by the dynamic imaging system for exploratory data analysis to predict the changes of the image (e.g., aging of a face or tumor growth, etc.). For example, a dynamic analysis of the growth of a tumor may be performed using the dynamic imaging system described herein (e.g., by analyzing the increase in the surface area or the volume of the tumor). That is, using the system described herein, the volumetric changes of a tumor or lesion is capable of being measured over a time period by software subtraction algorithms of the system as explained below, and then transmitted to the treating physician. In addition, the dynamic changes in a portion of a patient's body may be compared with existing data for diagnosis or differential diagnosis so as to track and analyze trends in disease progression or disease improvement against baseline data for management of diseases. The dynamic imaging system described herein may be configured to track changes in the disease process (e.g., diabetic retinopathy, another retinal disease, brain, spinal cord vertebrae, prostate, uterus, ovarian, intestine, stomach, extremities, lung, heart, skin disease, eczema, breast cancer, a tumor in the body, etc.) over a period of time so that the disease process is capable of being monitored by a physician. Also, follow-up images may be acquired using X-ray, CT-scan, positron, MRI, ultrasound, or photoacoustic imaging, etc.

In one or more embodiments, the body portion of the person being tracked by the imaging device comprises a tumor, lesion, retina, lung, or heart, and the dynamic imaging system is configured to dynamically analyze the growth of the tumor or lesion over a period of time by tracking the displacement of the tumor or lesion in a two-dimensional or three-dimensional manner over the period of time.

Figure 18A:
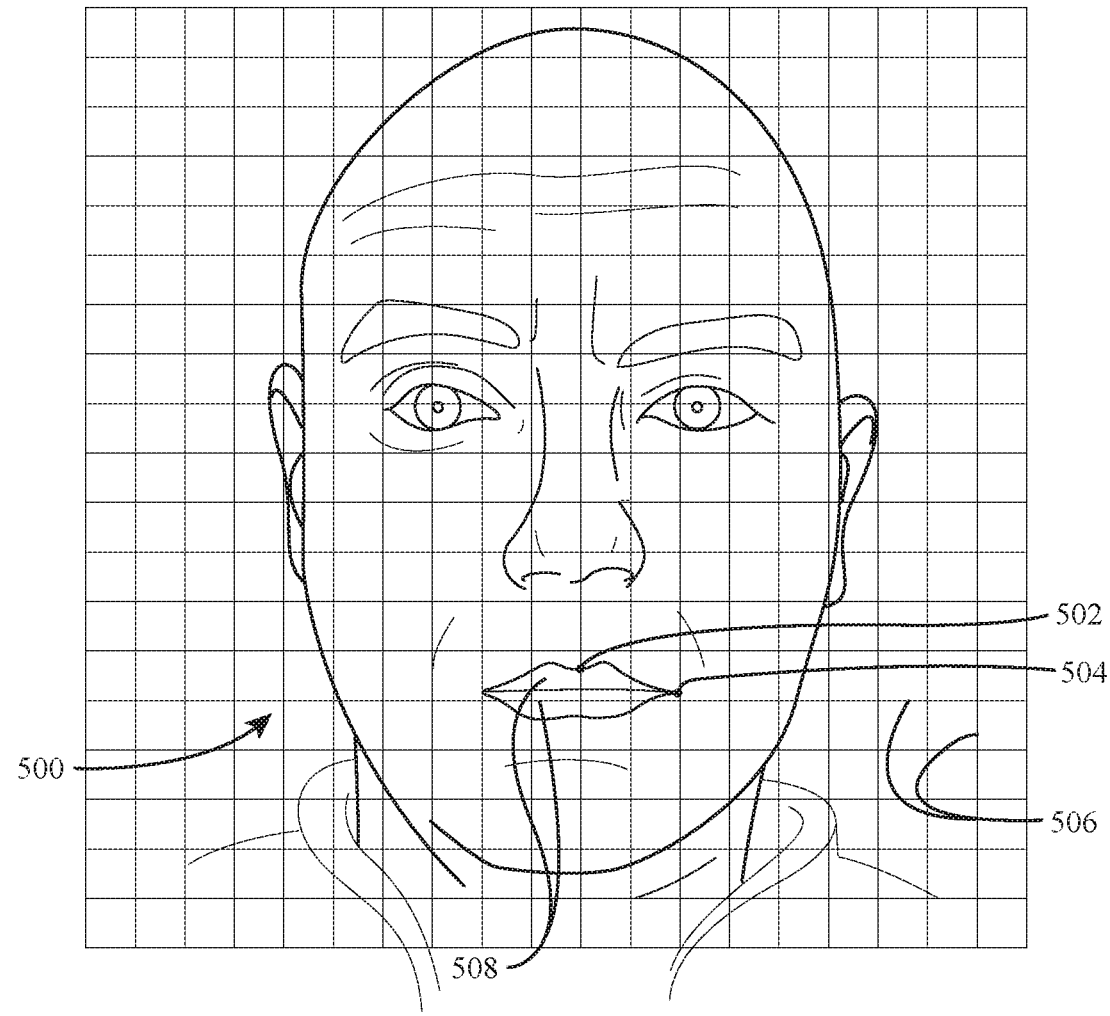
FIG. 18a is an illustration of a human face, depicting a grid that is projected over the facial area being analyzed using the dynamic imaging system of the remote laser treatment system described herein, and further depicting the positions of two exemplary points being used to track dynamic changes in the lips of the person.
Figure 18B:
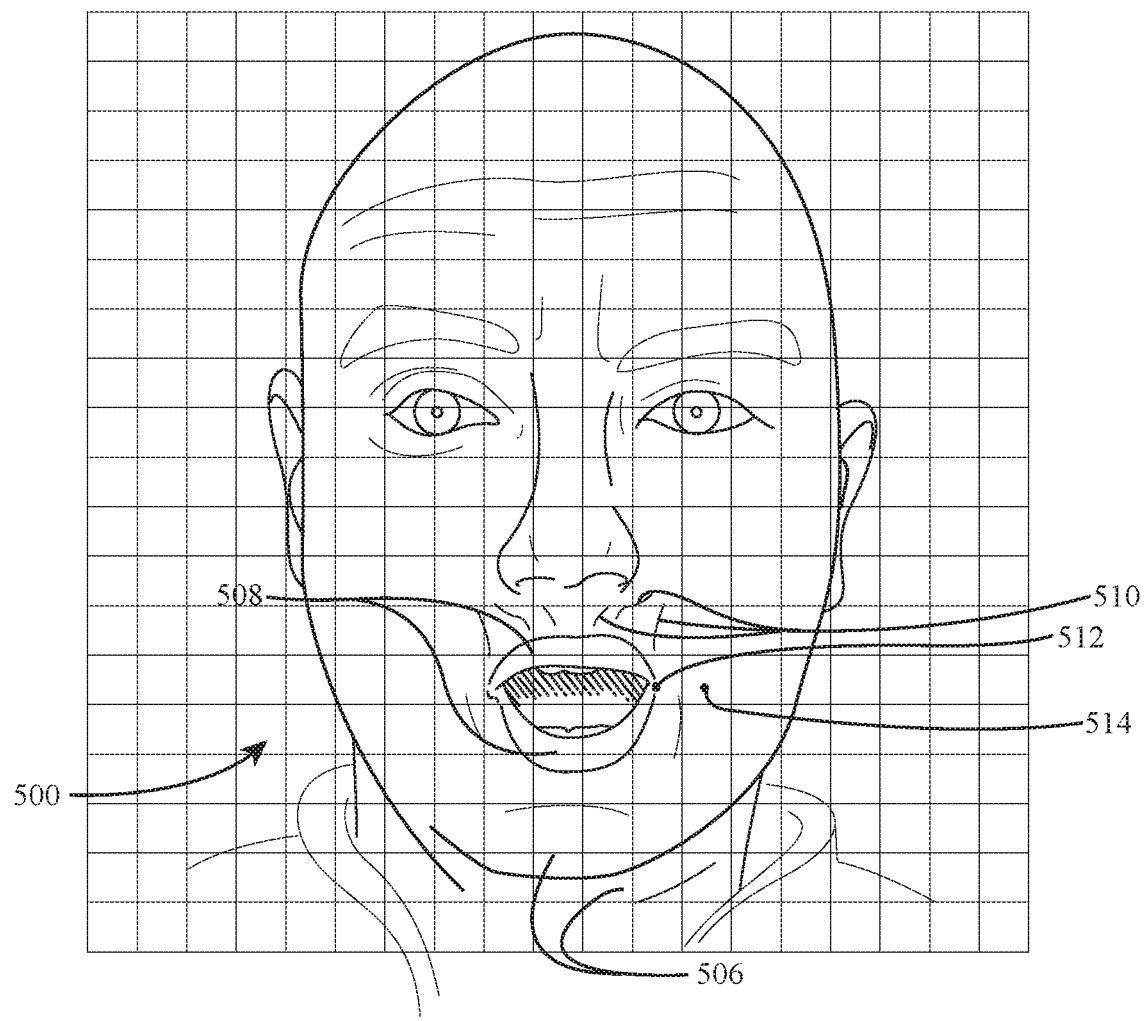
FIG. 18b is another illustration of a human face, depicting a grid that is projected over the facial area being analyzed using the dynamic imaging system of the remote laser treatment system described herein, and further depicting the positions of two exemplary points being used to track dynamic changes in the lips of the person while the person is speaking the letter "O"

In one or more embodiments, a grid is projected over the area of interest in the dynamic facial recognition system to clearly define the position of each pixelated area of the face to compare it with the image or displacement that has occurred in the process, and to superimpose images on each other by the computer executing a dynamic subtraction software algorithm to demonstrate the degree of the change and its trend during the displacement or change, thereby presenting it as a subtracted image when using a multispectral camera capable of analyzing the wide spectrum of the wavelength (images) including the infrared or near infrared wavelengths and analyze them by the software of the camera rapidly presenting it as 2-D or 3D images (refer to FIGS. 18a and 18b).

FIGS. 18a and 18b depict a grid 506 that has been projected over the facial area of a person 500 in order to track dynamic changes in the lips 508 of the person 500. In FIG. 18a, the positions of two exemplary points 502, 504 are being used to track the dynamic changes in the lips 508 of the person 500. In FIG. 18b, the positions of two exemplary points 512, 514 are being used to track dynamic changes in the lips 508 of the person 500 while the person 500 is speaking the letter "O". As shown in FIG. 18b, as the letter "O" is spoken by the person 500, grooves 510 are formed in the skin of the facial area surrounding the lips 508.

When the system is equipped with a multispectral camera, the multispectral camera may be used to obtain photos either in the visible spectrum or infrared to low infrared light spectrum working as a thermographic camera, seeing deep inside the skin to recognize the status of the circulation under the skin. The infrared pattern recognition capabilities of the system record psychological functional changes occurring under the skin (such as an increase or decrease in the circulation due to sympathetic activation-deactivation) together with dynamic changes, which are not achievable with a camera having only visible light capabilities.

In one or more embodiments, the visible spectrum provides information from the surface structure during the dynamic facial changes caused by deliberate activation of the facial muscles producing skin grooves around the mouth and the eye demonstrating the physical aspects of changes in a person being photographed in a two-dimensional and/or three-dimensional manner.

The computer software of the system analyzes both of the aforedescribed facial changes and presents them as independent values that can be superimposed mathematically by the computer's software creating subtraction data indicating the changes that have occurred serving as the initial face interrogation data. This subtraction algorithm may be used subsequently for recognition of a face, body, a tumor located on the surface of the skin or inside the body imaged to recognize the extent of changed values in two or three dimensional format. The dynamic imaging system described herein may also be used also along with standard imaging systems such as X-ray, CT-scan, MRI, positron, OCT imaging, photoacoustic imaging, thermoacoustic imaging, or optoacoustic imaging to record changes occurring in the images and its temperature after treatment over a time period. Because the images are pixilated bits of information that can be recorded live (e.g., for comparing an image before surgery and after the surgery), the images can be subsequently subjected to analysis with the subtraction algorithm of the computer software to decide, for example, if a tumor is completely removed or not.

In one embodiment, the algorithm and the software of dynamic image recognition system can be used to analyze the changes that can occur using artificial intelligence (AI) with a standard image technique such as X-ray, CT-scan, MRI, ultrasound, photoacoustic tomography, microscopy, optical coherence tomography (OCT), or confocal microscopy, etc. to diagnose early minute changes that occur in the body or tissue as a result of a disease process, such as macular degeneration, diabetes, heart or vascular disease, urogenital diseases, liver, kidney, or gastrointestinal diseases, extremities and joint diseases, skin diseases, Alzheimer's disease, Parkinson's disease, or other cerebrovascular diseases.

As another example, when the subject frowns, skin capillaries become collapsed and folded, thereby reducing the blood flow through the collapsed and folded capillaries and the heat that is detected by the multispectral camera. The subtraction algorithm provides the exact changes in facial structure during the frowning of the subject.

In one or more other embodiments, the subtraction algorithm executed by the computer presents only the subtracted image and its mathematical weight or value, and compares it with the previously obtained subtracted image of the same structure or face to verify the identity the person and compare the initial values and the extent of the changes between the first and second captured images, and the trend of the changes that have occurred after displacement of the surface or a structure of interest, such as a tumor dimension over time and its growth trend.

In one or more embodiments, the before or after image subtraction may be performed during the imaging of a tumor (e.g., a brain tumor) using contrast agents or antibody coated nanoparticles to demonstrate the degree of involvement of the brain and the effect of surgery or therapy on the 3-D dimension of the tumor indicating whether the tumor is able to be removed or treated completely or not. In one or more embodiments, the same computer algorithm is used in machine vision, robotic vision, or drone vision to examine the before and/or after effect of an action over time and predict the trend.

Figure 26:
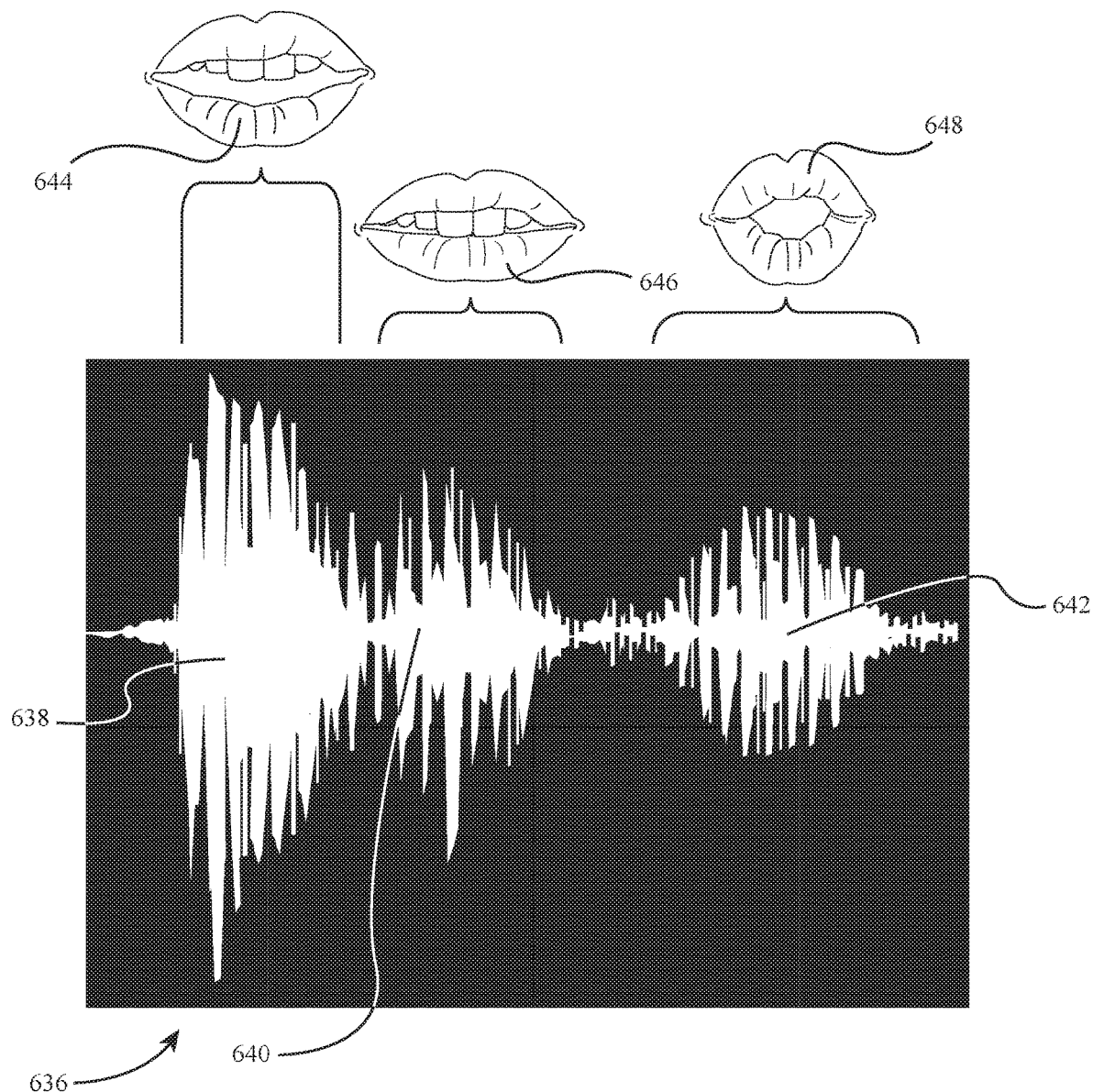
FIG. 26 depicts a graphical representation of a correlation between mouth configuration and a sound wave generated by a person while speaking a series of words.

In one embodiment, in dynamic facial recognition, a conventional existing mathematical algorithm is not used to compare two static images and conclude the possibility or probability of them being the same, but rather the computer of the present system is specially programmed to compare two sets of dynamic images, which are composed of one static and one dynamic, that add significantly more information by dynamic changes in a two-dimensional and/or three-dimensional manner that have occurred as a result of displacements of various points (e.g., in the face of the person) and the trend of the changes obtained by the computer subtraction of the dynamic changes, where to this, two significant values that augment the weight of the computer-generated image by superimposition of the obtained data or pre and post dynamic images for subtraction analysis by adding the voice or sound waves recorded simultaneously or superimposed over the dynamic facial values, and finally confirming the data with dynamic fingerprinting that has two additional components of finger print analysis, and multispectral photography before and after pressing the finger over the transparent glass, and collapsing the capillaries of the hand or the finger that provides practically a complementary algorithm for nearly infallible identity recognition data of a person within a timeframe of 2½ seconds or less. For example, FIG. 26 depicts a graphical representation 636 of the correlation between the mouth configuration and the sound wave generated by a person while speaking the words "I love you". The first section 638 of the sound wave corresponding to the speaking of the word "I" produces an open mouth configuration 644 with wrinkles on the lips of the mouth. The second section 640 of the sound wave corresponding to the speaking of the word "love" produces a semi-closed configuration 646 of the mouth where the lips touch the teeth. The third section 642 of the sound wave corresponding to the speaking of the word "you" produces a semi-closed, generally round configuration 648 of the mouth.

In one embodiment, the dynamic facial recognition technology described herein uses a software program that not only subtracts the data obtained in the first session from the data obtained in the second session, but similarly through its subtraction algorithm, compares the sound wave of a person at each examination setting to show the difference or the trend, along with final confirmation of the data with dynamic fingerprinting technology of pressing a finger or palm of the hand over a transparent glass which is photographed before and after pressing the finger/palm with multispectral light waves to demonstrate the finger's or palm's circulation pattern, or its collapse after pressing it over the transparent glass, in addition to the ridges of the skin, folds, minutiae, etc. in a two-dimensional and/or three-dimensional manner for dynamic identity recognition.

The technology described herein demonstrates a way to subtract the information of a dynamic change mathematically from a dynamic recognition data of not only the face, but also extremities or a moving person or variation of the facial folds measured by a multispecteral or hyperspectral camera or color changes of the collapsed capillaries observed after pressing the finger or palm, or changes of the facial capillaries during an interrogation, or observation of a joyful or sad movie, etc., which all add value to the correct identification of a person.

In one embodiment, the subtraction algorithm may also be used to predict a trend using one of the existing mathematical algorithms described below, and recognize changes or the trend for evaluation of dynamic imaging, and another dynamic imaging related to the first set, such as adding a value or one dynamic facial recognition with another one created by pressing of the face to bleach the facial capillaries or inducing an artificially induced element that changes the facial folds (e.g., created by frowning to that of the voice and dynamic changes of the mouth by speaking a vowel or smiling, etc.) in a two-dimensional and/or three-dimensional manner.

In one embodiment, the accuracy of the dynamic facial recognition system may be augmented with the use of another existing mathematical algorithm, such as an artificial neuronal network, interval finite element analysis, fuzzy logic variations, machine learning, rough set, Sorties Paradox, vector logic, etc.

In one embodiment, the camera of the dynamic facial recognition system is equipped with software for machine learning, with a neuronal network and medical imaging or perception, natural language, speech recognition, big data decision-making of the changes that occurs in a dynamic format or anthropology software, or artificial intelligence capable of reconstructing a complete image from a part of the image or information that is obtained from a person.

In one embodiment, the person being imaged or photographed is an active participant in the process that implies the person in giving his consent by participating in the process and his photograph is not taken without his permission randomly by a camera located in a location.

In one embodiment, standard facial recognition may be used with a telemedicine system despite its shortcoming of the person's recognition and the fact it does not provide or imply a person's consent, by using a recording to record the person's consent for telemedicine communication by asking the person to indicate his or her consent by responding to the question if she or he would give permission to discuss his or her health or other issues by indicating "yes" or "no", or any other means voluntarily while being recorded by a camera or voice recognition system, etc.

In one embodiment, the person writes "yes" or "no" while the computer recognizes the handwriting with the handwriting recognition, or the person presses over an area of the monitor of a computer where the computer has selected indicating "yes" or "no" where the computer can recognize the person from the minutiae of the tip of her or his finger along with dynamic recognition of the capillaries, or simultaneously observing the dynamic changes of the person's face, etc. (i.e., recording two or more independent tasks for recognition).

In one embodiment, the dynamic recognition is used in telemedicine, and one of its function is to secure a person's consent in telemedicine that involves asking a person for his consent to take a photo or dynamic imaging from him or any of his or her body part and obtaining his or her consent verbally or by head or hand or eye finger motion, etc., or adding his fingerprint to a surface of the computer or a smartphone that can record it in a 2D or 3D form or in a dynamic format with imaging the changes in the fingertip or the organs or capillaries or using a sensor to simultaneously measure the pulse rate, etc. of the person, while the voice recognition software records the sound waves of a patient in his native language or another language for future verification, and the sound waves are recorded, stored and encrypted.

In one embodiment, the dynamic image recognition is used in combination with computer artificial intelligence (AI) software and a camera that mimics human recognition by learning and solving problems including identity of a person or a structure or a lesion, its dynamic changes and data searching, calculating, sensing the environment in depth or sensing, the social intelligence using linguistic, psychology, mathematic and neuroscience to create new images and recognize the emotional changes of a person or animal.

In one embodiment, the dynamic image recognition system is capable of learning algorithms that can recall, learn, and infer changes in recognizing a person, lesion, etc. in any image presented with standard photography or hyperspectral imaging, X-ray, MRI, or CT-scan, microscopy or confocal microscopy or OCT, etc. using hierarchal temporal memory software.

In one embodiment, the dynamic image recognition system uses the mathematical means of fuzzy logic or vagueness in a complex situation for recognition of difficult images to differentiate certain persons (e.g., twins, etc.), along with dynamic identity recognition and machine learning, speech recognition, to differentiate the effect of the environment on the person or animal or any other living structure.

In one embodiment, the dynamic identity recognition system uses the artificial intelligence (AI) with various existing software instructions, algorithms, such as dimensional reduction, structural prediction, anomaly detection, artificial neuronal network, parallel constraint satisfaction, or parallel distributed processing, etc.

In one embodiment, the dynamic identity recognition is used with robotic machine vision for macroscopic or microscopic differentiation of at least two similar or dissimilar objects, the position, and 3-D format in order to perform a task precisely as instructed by the software.

In one embodiment, the tunable field camera can have a tunable lens or the one fluidic lens.

In one embodiment, the tunable lenses are tunable lens with shape-changing polymer lenses (i.e., Optotune®), liquid crystal lenses, electrically tunable lenses, electrowetting lenses (Varioptic®), or the fluidic lenses described by Peyman in U.S. Pat. Nos. 7,993,399 and 8,409,278, etc.

In one embodiment, the tunable light field camera can be an integral part of the laser coagulation system or be provided separately as a camera.

In one embodiment, a tunable light field camera or other field cameras can be used with the tele-laser system or separately, or they can also be used as a part of the facial recognition system as a dynamic facial recognition system. Tunable light field cameras offer a precise focusing concept using the microlenses, nanosensors, and a computer to analyze various focal points that can be created mathematically using specific algorithms.

In one embodiment, the tunable light field camera uses the computer to verify or identify various changes that can happen during the change in physiological function of a person, such as smiling or frowning, as a digital 2 D or 3-D image or video frame recording the changes and analyzing and comparing the biometrics as a dynamic physiological fingerprints with the existing date of the same image (e.g., a face, etc.) using mathematical dynamic pattern recognition. The computer algorithm analyzes the changes in the relative position of a patient's face by matching points and directions and compressing the data obtained during the process using dynamic recognition algorithms.

In one embodiment, the dynamic identity recognition uses a geometric algorithm to distinguish the features of a person or a lesion, etc., and photometric analysis provides precise statistical data from the images to compare the data template e-variances.

In one embodiment, a retinal scan provides not only the identity of a person evaluating a unique pattern of a person, but can be used to analyze the changes in the thickness of the retinal structures, along with OCT and analyze the changes of the retinal capillaries and retinal pigment epithelium, etc. using the known principal component analysis or linear discriminant analysis (LDA), generalization of Fisher's linear discriminant, pattern recognition, and machine learning to provide prognostic information (e.g., in age related macular degeneration of diabetic retinopathy, glaucoma, and other diseases causing retinal degeneration or abnormal blood vessels).

In one embodiment, in dynamic identity recognition (DIR), one uses 3-D images that are created for skin texture analysis by projecting structured light on the skin, mucosa or retina, etc. (e.g., for a security system at an ATM).

Figure 22:
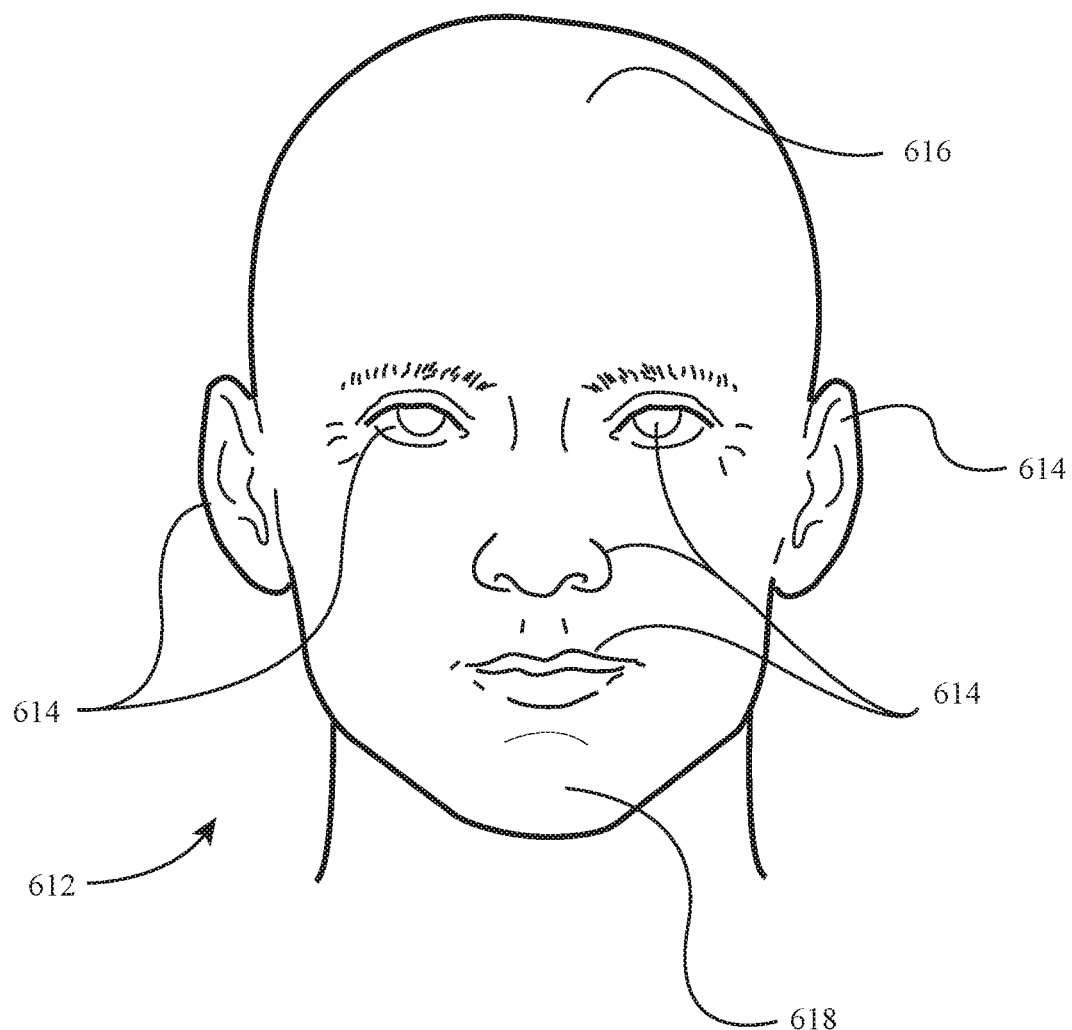
FIG. 22 depicts a computer-modified image of the face of the person in FIG. 20 where the hair and facial hair of the person have been removed, and the stable features of the person are depicted.
Figure 23:
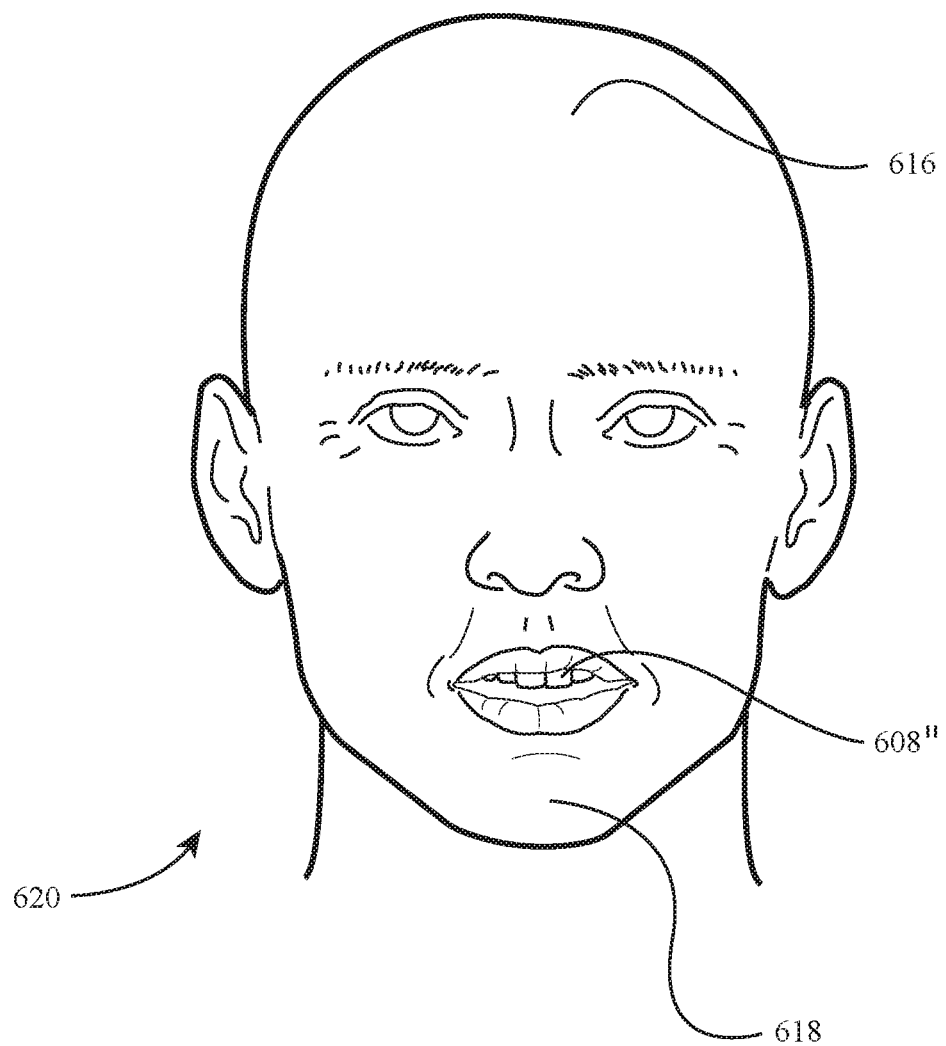
FIG. 23 depicts another image of the face of the person in FIG. 20 captured by the dynamic identity recognition system where the appearance of the midsection of the face has remained generally stable, but dynamic changes have occurred in the lower section of the face.

In one embodiment, the computer modifies the 3-D image of a person taken instantaneously or an existing image and modifies it with its artificial intelligence (AI) system for a search of similar images in its file or the computer can modify the person or animal image by adding or subtracting certain variable components to the person, such as adding different types of hair including color, etc., or remove the hair, changing the facial hair, adding or subtracting earrings, changing the skin color or the color of the iris, adding or subtracting glasses, etc. By confirming the stable points in an image (e.g. distances between the eye, nose, mouth, ear, etc.—see e.g., stable features 614 in FIG. 22) to confirm the identity of the person being examined, these tasks can be performed rapidly by a processor.

Figure 20:
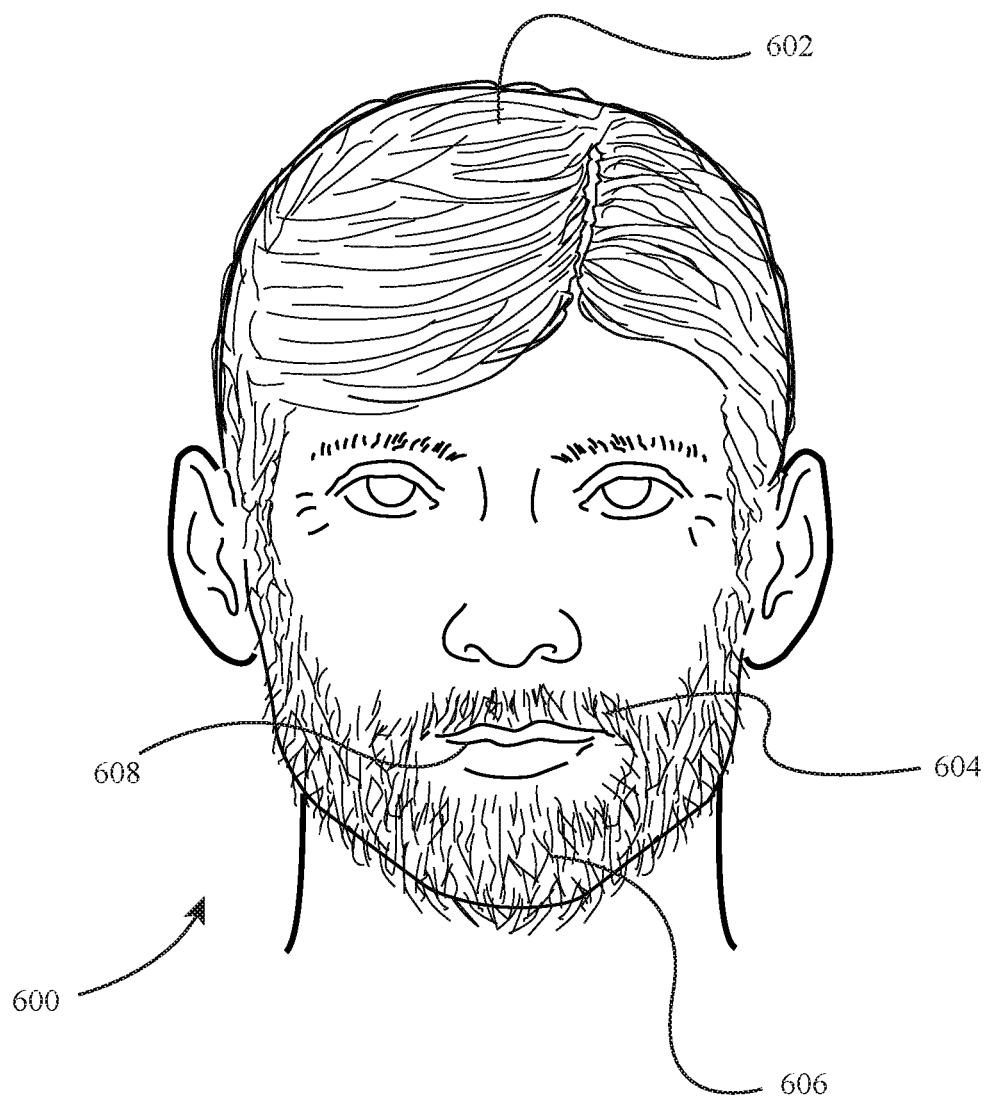
FIG. 20 depicts an initial image of a face of a person captured by a dynamic identity recognition system where the person has hair and facial hair.
Figure 21:
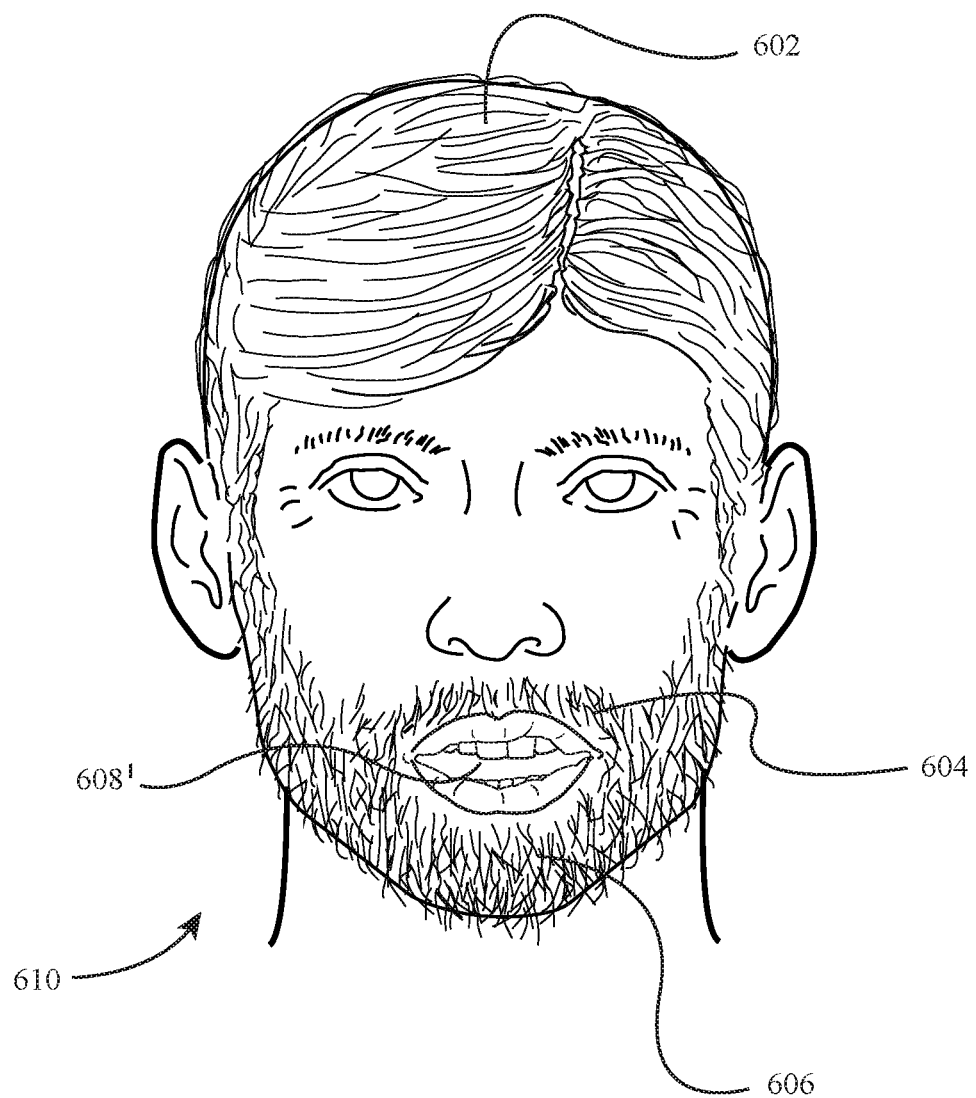
FIG. 21 depicts another image of the face of the person in FIG. 20 captured by the dynamic identity recognition system where the appearance of the midsection of the face has remained generally stable, but dynamic changes have occurred in the lower section of the face.

In one embodiment, the dynamic identity recognition system can add or subtract, using software and artificial intelligence (AI), a 3-D distinct feature after it has checked a person with the dynamic recognition system (i.e., before and after dynamic images and computer generated modifications). This computer software has the ability to artificially create an instant match with the person that is being examined by creating hundreds or thousands of similar images (e.g., by adding hat or glasses or changing the hair color of the subject and look for comparison in its previously stored memory). As shown in FIGS. 20-25, the specially programmed computer of the dynamic identity recognition system is able to eliminate the beard or hair of a person while evaluating other stable features or dynamically changed features of the same person, including the voice of the person, etc. For example, in FIG. 20, an initial image of a person 600 depicts the person with hair 602, a moustache 604, and a beard 606. In FIG. 20, the mouth 608 of the person is in a closed configuration. Turning to the image 610 depicted in FIG. 21, it can be seen that a dynamic change in the appearance of the person has taken place. More specifically, a dynamic change in the lower section of the person's face has occurred (i.e., the mouth configuration 608' is different from that of FIG. 20, resulting in enhanced folds on the face and visible teeth), while the midsection of the person's face has remained generally stable without any significant changes.

Figure 24:
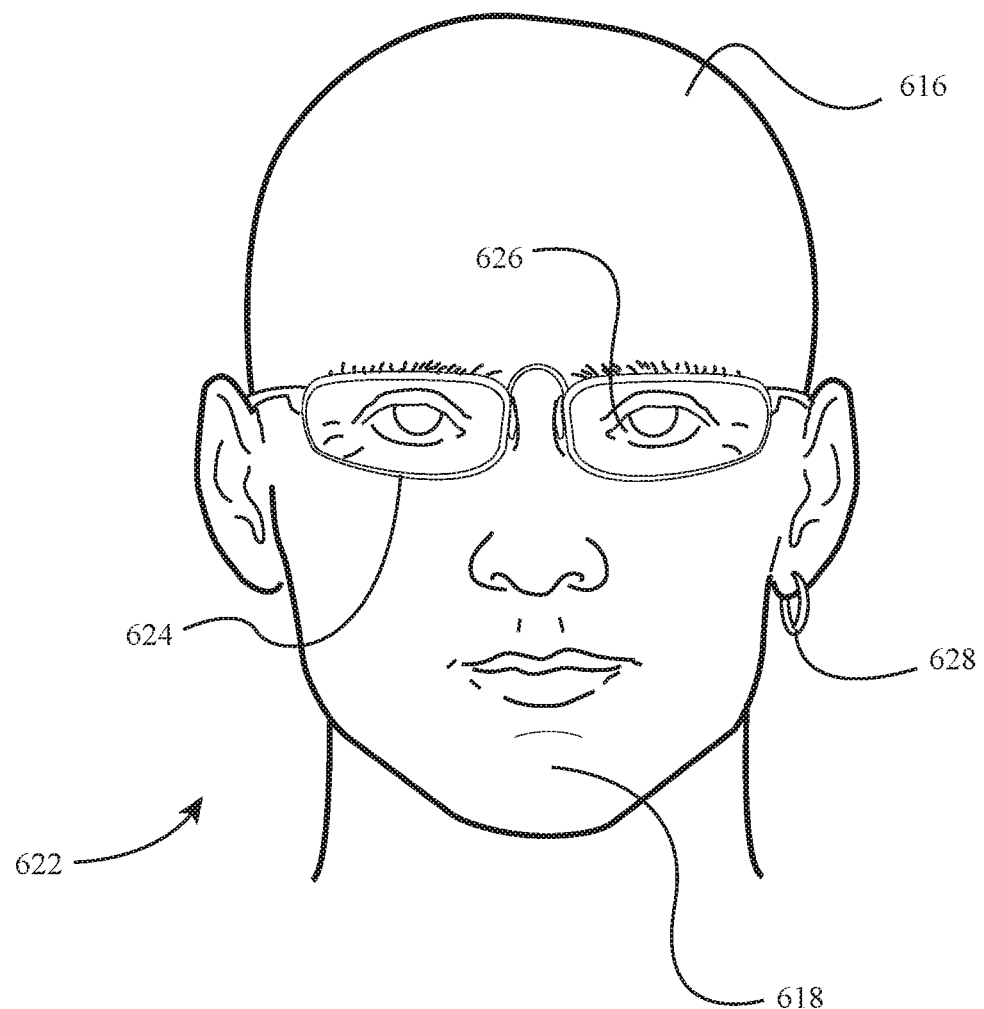
FIG. 24 depicts a computer-modified image of the face of the person in FIG. 20 where the hair and facial hair of the person have been removed, and glasses and an earring have been added to the person.

In one embodiment, the software of the dynamic identity recognition system can change the color of the skin, hair, or beard of the subject using all possible colors of the light spectrum, or adding hats or hair, toupee hair pieces or mustaches, or earring(s), etc. and/or converting the face of the person or patient to an emotional face showing, being sad, being happy, or being in pain, etc. using the appropriate existing folds and skin capillary color, fold compression enhancing or decreasing the capillary circulation creating specific color intensity specific to the emotional and physiological state of the subject's feelings, such as well-being, using an infrared (IR) and visible light system in 3-D along with AI, AR, and VR software, using the voice recognition software for the subject's voice and variation of sound frequency and amplitude to recognize the physiological state of the subject. For example, in FIG. 22, a computer-modified image 612 of the person is depicted where the hair 602 of the person has been removed, thus resulting in a bald head 616. Also, the facial hair of the person has been removed, thereby resulting in a hairless chin 618. The computer-modified image 612 in FIG. 22 enables the dynamic identity recognition system to be spoof-proof by enabling the system to still accurately identify the person even if the person shaves his head, and removes his facial hair. In the case of such changes in the appearance of the person, the dynamic identity recognition system is still able to accurately identify the person by focusing on the stable features 614 of the person. Turning to the image 620 depicted in FIG. 23, it can be seen that a dynamic change in the appearance of the person has taken place. More specifically, a dynamic change in the lower section of the person's face has occurred (i.e., the mouth configuration 608" is different from that of FIG. 22, resulting in enhanced folds on the face and visible teeth), while the upper section and midsection of the person's face has remained generally stable without any significant changes. In FIG. 24, another computer-modified image 622 of the person is depicted where glasses 624 have been provided on the person, the iris color 626 of the eyes of the person has been changed, and an earring 628 has been added to one of the ears of the person. In order to make the dynamic identity recognition system spoof-proof, other computer-generated anatomical and cosmetic variations can also be made to the person, such as changing the skin color of the person, adding a hat on the head of the person, adding lipstick to the person, changing hair color, changing facial hair color. These computer-generated changes to the image of the person enhance the likelihood of an identity match by the system even when the person alters his or her appearance (e.g., by shaving his head, shaving his facial hair, etc.).

Figure 25:
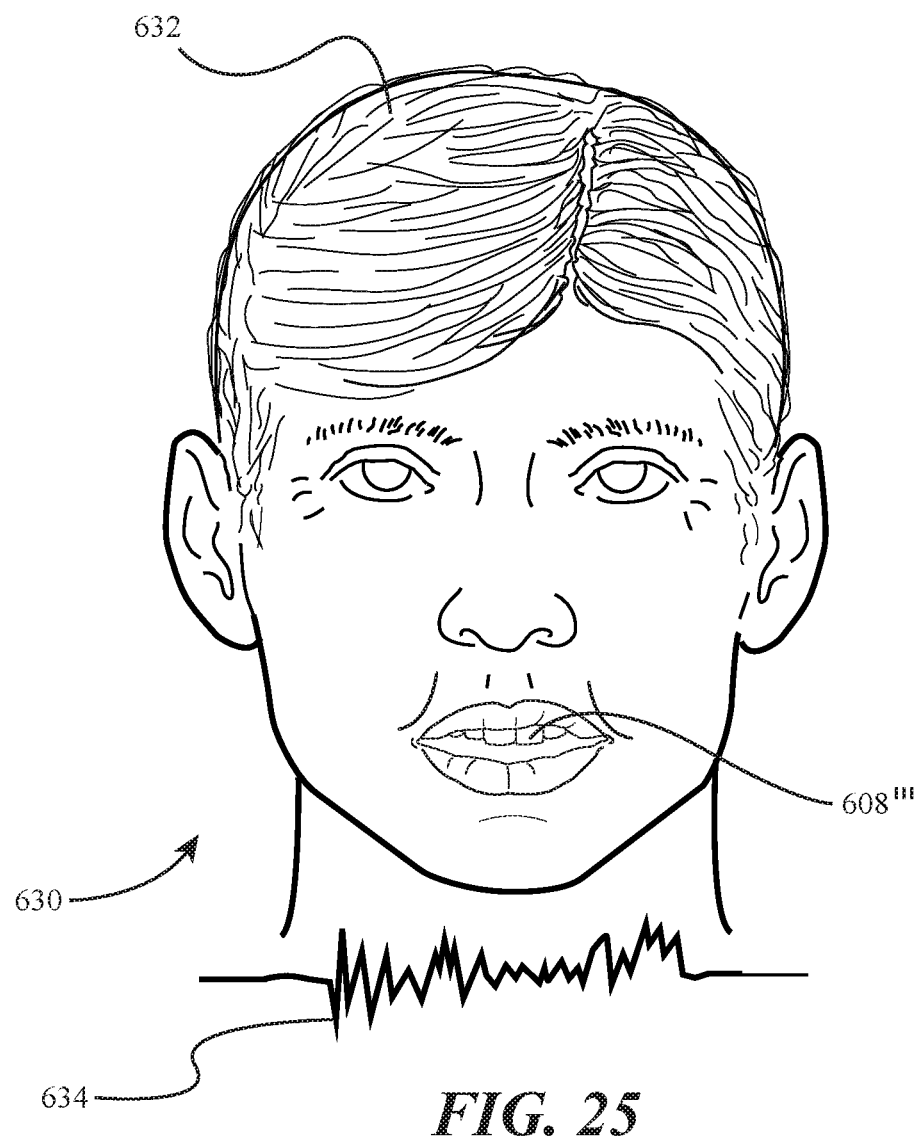
FIG. 25 depicts a computer-modified image of the face of the person in FIG. 20 where an artificial change in the appearance of the person has occurred while the person is speaking one or more words.

In one embodiment, the dynamic identity recognition system can also simultaneously recognize via the software executed thereby the emotional changes that are associated with the existing folds and capillaries of the skin of a person's face that are enhanced by the emotional changes and can be subtracted from the existing prior images of the person or the patient, etc. In FIG. 25, another computer-modified image 630 of the person is depicted where an artificial change in the appearance of the person has occurred while the person is speaking one or more words (i.e., represented by the sound wave 634 in FIG. 25). As shown in FIG. 25, the computer-modified image 630 simulates a dynamic change in the lower section of the person's face while the person is speaking the one or more words (i.e., the mouth configuration 608''' is different from that of FIG. 24, resulting in enhanced folds on the face and visible teeth). Also, in FIG. 25, simulated hair 632 has been added to the person to increase the probability of an identity match if the person grows hair after being bald.

In one embodiment, the dynamic identity recognition system can diagnose the emotional changes by the use of its camera's imaging in the visible spectrum or in the infrared (IR) spectrum.

In one embodiment, the computer of the dynamic identity recognition system can record and subtract the emotional changes instantaneously induced by conditions, such as anger or smiling, sickness, pain, or asking a question or remembering a past experience or trauma, etc.

In one embodiment, the computer of the dynamic identity recognition system presents the before and after images and the subtracted one (e.g., from the original person's file to diagnose the physiological or emotional state changes of the subject).

In one embodiment, the dynamic identity recognition system eliminates or creates spoofs for potentially creating a semi-virtual representation of the person with arbitrarily changing certain characteristics (e.g., the hair for matching the images of the subject for comparison purposes, or recognizing the dynamic emotional changes of the subject both useful in the medical field for diagnosis of an existing psychological condition or use in a security system recognizing the person's response to, for example, a question or a joke recognizing the physical and emotional changes in the images in 2-3-D format—see e.g., FIG. 25).

In one embodiment, all photos can be observed with specific glasses or goggles as AR or VR. Since, the images are taken in 3-D, they can be observed in 3-D and from any direction and volumetric analysis of the object (e.g., head, nose, ear, chin, or a tumor, etc. can be compared or analyzed).

In one embodiment, the computer of the dynamic identity recognition system can access any library of images for obtaining existing prior images or information, or similar images including clinical ones such as X-ray, MRI, CT-Scans, or photographs, etc. for analysis etc.

In one embodiment, a computer with dynamic identity recognition capabilities and artificial intelligence (AI) can generate from a person or animal a present image and a new computer-generated older or younger person's secondary image as long as certain elements or similarities are discovered in the initial image to identify in the 2 to 3 dimensional image of the present image using AI and artificial neural networks (ANN) to create a new secondary image to build on the bases of unchanged parts of the present image (e.g., stable features 614 in the image 612 of FIG. 22), and alternative images with the same basic characteristics for identification using a software similar to those utilized in anthropology, to discover a whole structure from only a part of the image or generating identifying characteristics from the examples (present image) that it processes.

In one embodiment, the software and algorithm of dynamic identity recognition (DIR) and artificial intelligence (AI) can be used in the recognition of a person or an animal, or a person lost because of a mental disease, such as Alzheimer's disease, or in a forensic situation.

In one embodiment, the software algorithms of dynamic identity recognition (DIR), artificial intelligence (AI), and artificial neural networks (ANN) with distributed computing and deep learning or the bi-directional and multi-dimensional long short-term memory (LSTM) or convolutional neural networks (CNN), etc. can be used in system identification or control in trajectory prediction in microscopic or macroscopic fashion, general game playing, 2-3 D pattern recognition of inanimate objects or live humans, animals and other living things, signal classification, voice recognition, winking, gesture, or other facial expressions, etc., word or sounds expression of good or bad, handwriting recognition, medical, recognition of a disease process such as cancer, before and after surgical procedure for tumor or in orthopedic surgery etc., visualization, microscopy, recognition, such as cells, tissue samples, bacteria, fungi, viruses, in swab, biopsy or in tissue culture with simultaneous quantification.

In one embodiment, the dynamic identity recognition system utilizes components of artificial intelligence (AI) including training, validation with image and data, combined with a technical network, such as a convolutional neuronal network (CNN). The training includes recognition of obvious characteristics (e.g., such as face, eyes, nose, mouth, etc.) requiring focused images in 2D to 3D format or dynamically changed images that provide additional data along with voice recognition with deep learning algorithms such as CNN, VGGNet, AlexNet, Inception V4, DenseNe, and ResNet.

In another embodiment, in a clinical setting, the dynamic identity recognition system utilizes components of artificial intelligence (AI) in evaluation of a disease process in addition to what is described above for identity recognition of an individual. Artificial intelligence (AI) requires a standard or normal reference and means of comparison by human experts along with data collected from a large number of subjects. The machine learning or deep learning in artificial intelligence (AI) includes data obtained from clinical presentation, images and additional multimodal data, such as laboratory information used with deep learning algorithms, such as neuronal computational layers available as CNN, VGGNet, AlexNet, Inception V4, DenseNe, and ResNet.

In another embodiment, the multispectral or hyperspectral camera is used to obtain both spectral and spatial data from the images before and after the dynamic changes have occurred on an external area of the subject. In one embodiment, the characteristics and changes of a moving object is recorded and analyzed providing simultaneous imaging, processing, and evaluation by the software of the processor of the camera, thus sensing the simultaneous changes that are happening and the trend of the changes (e.g., on the surface or below the surface of the skin or a subject being photographed). In one embodiment, the dynamic images obtained from the surface can be combined with the information obtained by the ultrasonic unit of the laser system to provide additional information from a deeply located, internal body structure, such as bone, joints, or a moving object, etc. In one embodiment of the remote laser system, the electronically obtained images are combined with CMOS image sensors (e.g., analyzing a subject's fingerprint can give information on the blood flow of the fingertip before or after applying pressure with the finger that collapse the fingers skin capillaries and the changes may be analyzed in real-time).

Figure 19A:
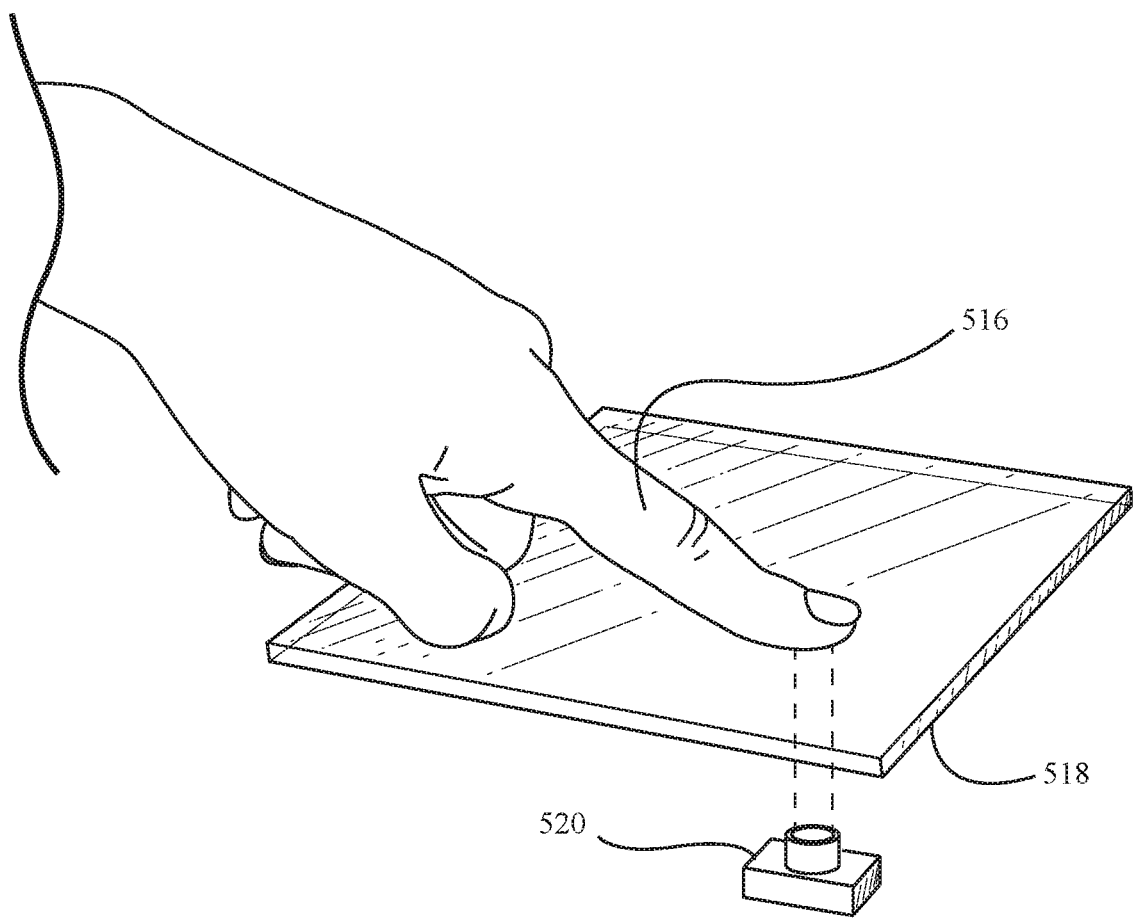
FIG. 19a is an illustration of a finger being pressed against a transparent glass surface so that the tip of the finger is capable of being imaged.

For example, a dynamic fingerprinting and/or dynamic hand recognition system will be described with reference to FIGS. 19a-19c. Initially, as shown in FIG. 19a, a finger 516 containing numerous ridges and folds is placed on a surface of transparent glass 518 so that the finger is able to be imaged (i.e., photographed or videoed) with an infrared spectrum and/or visible spectrum of a field camera, multispectral camera, or hyperspectral camera 520 of the remote laser system. Rather than simply imaging the fingertip in FIG. 19a, the entire hand of the person also may be imaged using the camera 520. The system of FIG. 19a may also record the color of the fingertip or hand of the person prior to its placement on the surface of transparent glass 518 together with the folds and ridges of the fingertip and hand.

Figure 19B:
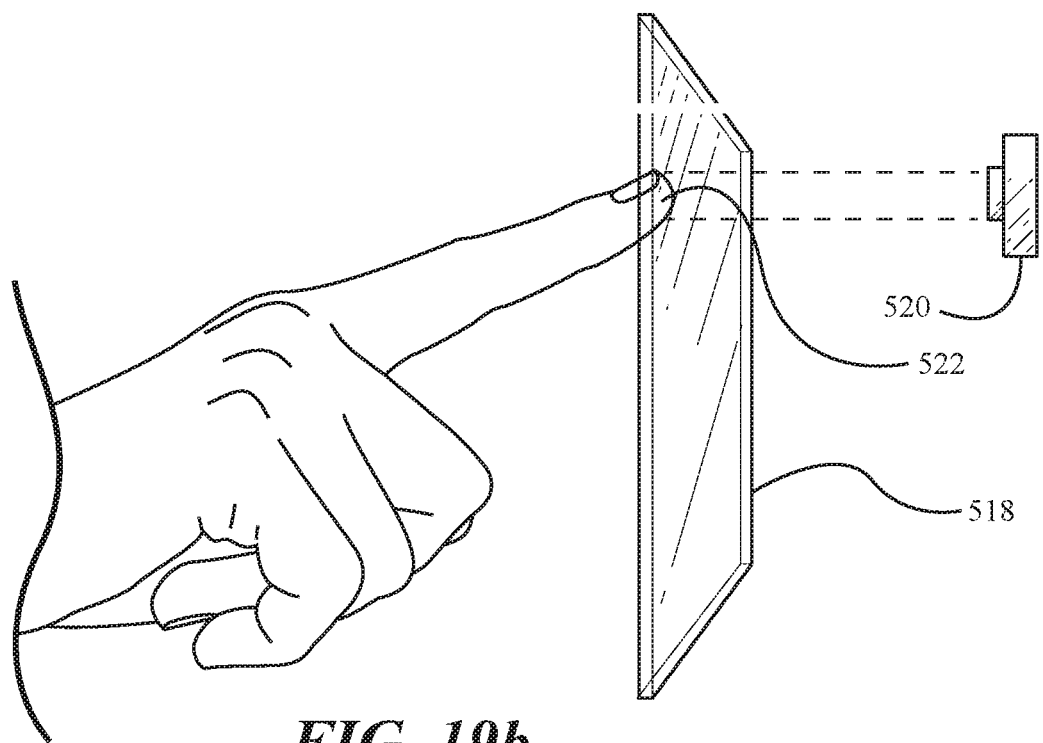
FIG. 19b depicts a finger before touching a transparent glass surface used for the imaging of the finger.
Figure 19C:
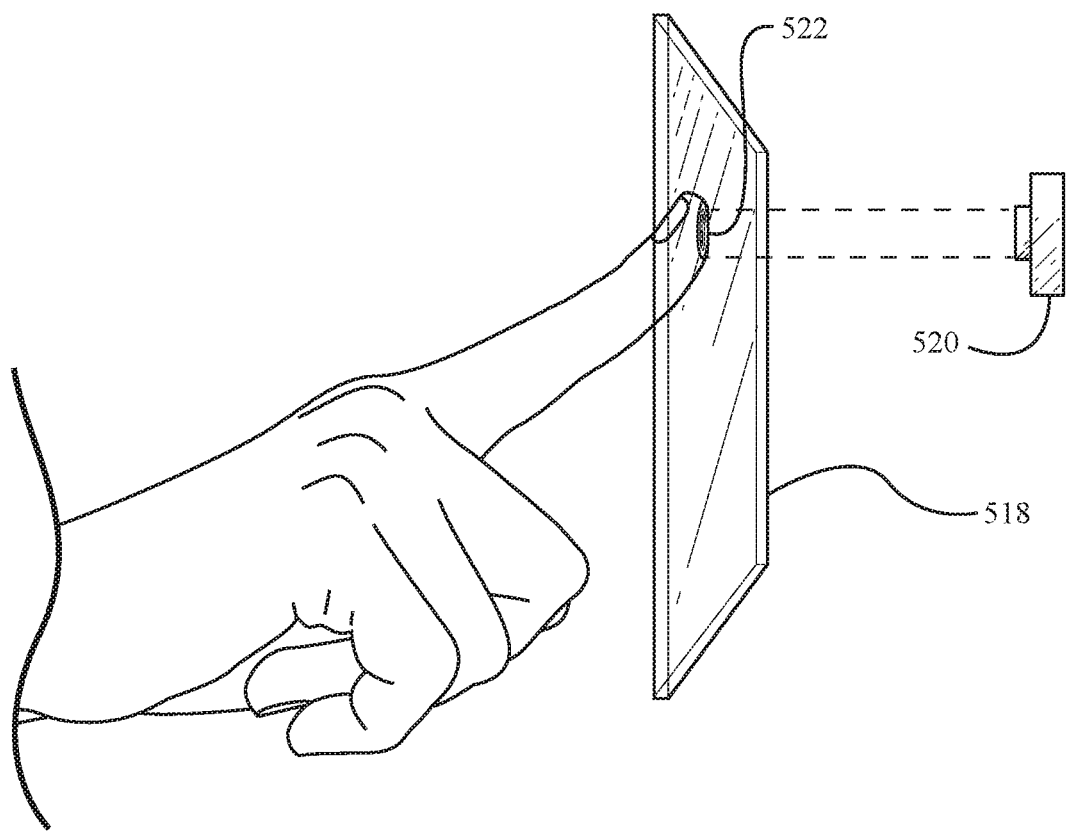
FIG. 19c depicts the finger touching the transparent glass surface, the finger undergoing imaging that takes into account both surface and subsurface properties of the finger in a two-dimensional and/or three-dimensional manner.

Then, turning to FIG. 19b, a finger 522 is illustrated prior to touching the surface of transparent glass 518 and being imaged by the field camera, multispectral camera, or hyperspectral camera 520 of the remote laser system. FIG. 19b depicts the fingertip or ball of the finger 522 with its circulations, ridges, and minutiae, which are able to be imaged using the camera 520 for highly reliable identification of the person. The infrared spectrum of the camera 520 is able to record the warm circulation of blood through the fingertip or ball of the finger 522. FIG. 19c shows the ridges of the fingertip of the finger 522, but centrally, the capillaries of the finger 522 are collapsed at the area where the fingertip or finger ball is touching the surface of transparent glass 518, which indicates that a live person is being recorded. In FIG. 19c, where the capillaries collapse at the ball of the finger 522, the finger 522 becomes devoid of circulation (thus turning red in color) at the site of compressed area compared with the previous image; these changes are present in infrared photography. Advantageously, the system of FIGS. 19a-19c preserves the folds in the finger 522 or, if the whole hand is placed on the glass 518, the folds in the whole hand. In the illustrative embodiment, all of this information is recorded before and after placement of the finger 522 or hand on the glass 518, and the changes are subtracted to obtain the verification of the person's identity, and the physical and physiological changes that have occurred are analyzed to recognize and verify the person's identity.

In one embodiment, the person's finger, hand, or other extremities are videoed to create more complete information regarding the identity of the person or the area of the body recorded for future dynamic comparison, etc. In addition, a voice instruction may be included in the system of FIGS. 19a-19c in order to ask the person to press harder, or loosen up his or her finger, so that the degree of the capillary bleaching is confirmed, etc.

Also, in one or more embodiments, three-dimensional dynamic data is obtained either from multiple cameras or from the mathematical analysis of the obtained digital data from the light field camera system. Advantageously, the rapid variation of the light field camera eliminates the problem seen with moving objects that interferes with a good static facial recognition. Additional data can be obtained on the skin and its changes during the physiological dynamic imaging with an infrared camera or multispectral camera.

In addition to use in the remote laser treatment system 50' described above, the dynamic imaging system described herein may also be used for other applications, such as for security system applications, use in HoloLens applications, use in telemedicine applications (e.g., tele-imaging or tele-diagnostic systems), and use in other patient applications, such as looking at the growth of various lesions over time and aiding with diagnosis and differential diagnosis. Other applications for the dynamic imaging system described herein may include specific applications involving hospitals for patient security and operating room applications, customs department, airports, the state department, police (e.g., for investigative analysis of the crowd or identification a person), the military, FBI, CIA, various other governmental agencies, and banking institutions (i.e., for account and ATM identification). The dynamic imaging algorithm may also be used in robots, drones, in agriculture applications, or in military applications. The dynamic imaging system may also be useful at stadiums of competitive sporting events, such as football, soccer, basketball, and hockey stadiums, and at other venues involving large gatherings of people for political or non-political causes, which often require some permission to guarantee the privacy and safety of the people present at the event. In addition, the dynamic imaging system may be used in smartphones for remote recognition, and in home security systems, etc.

In one or more embodiments, the dynamic facial recognition system described herein may replace previous verification/identification systems used in personal life, such as passwords IDs, PINs, smart cards, etc. The dynamic facial recognition system also has unlimited applications in personal security, identification, passports, driver licenses, home security systems, automated identity verification at the airports, border patrol, law enforcement, video surveillance, investigation, operating systems, online banking, railway systems, dams control, medical records, all medical imaging systems, and video systems used during surgery or surgical photography to prevent mistakes in the operating room (e.g., mistaking one patient for another one, or one extremity for the other). The dynamic imaging system described herein may also be used for comparative image analysis and recognizing the trends in patients during follow up analyses and outcome prediction. The dynamic imaging system described herein may also be used with other imaging modalities, such as X-ray, CT-scan, MRI, positron, photoacoustic technology and imaging, ultrasound imaging, etc. Further, the dynamic imaging system may be used for image and data comparison of close or remotely located objects, mass surveillance to document time related changes in the image, and/or recognizing a potential event and its trend.

Laser-Imaging System with Global Positioning System (GPS) Capabilities

Figure 17:
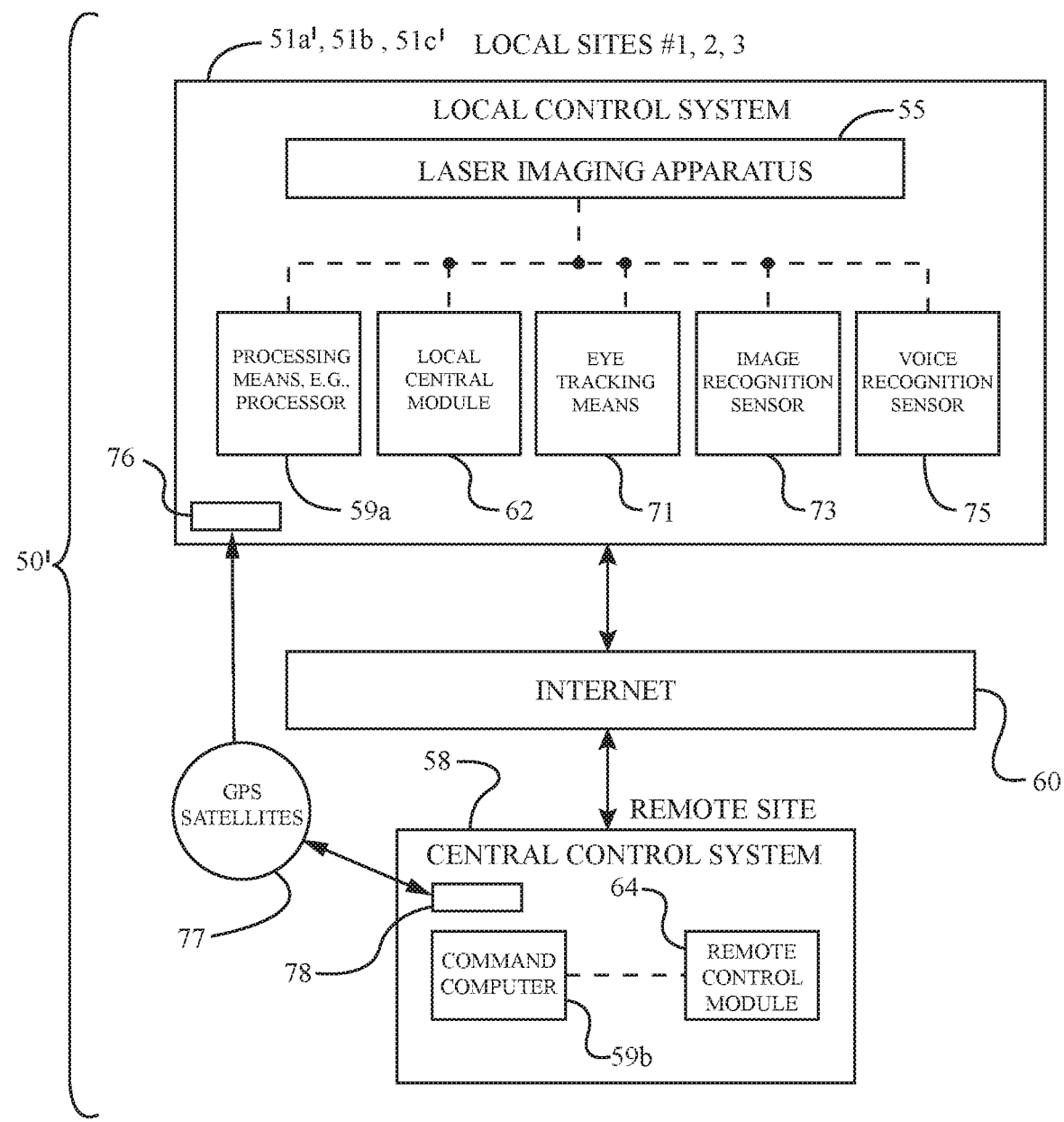
FIG. 17 is a schematic illustration of another embodiment of a laser-imaging system, in accordance with the invention, wherein the remote laser treatment system is provided with GPS-based identification of the laser treatment application site.

In another further embodiment, the laser-imaging system 50' may be provided with GPS-based identification of the laser treatment application site. With reference to FIG. 17, it can be seen that the local control systems disposed at local sites 51a', 51b', 51c' may each include a Global Positioning System (GPS) receiver unit 76 that communicates with a cluster of GPS satellites 77. In particular, the GPS receiver unit 76 may receive radio signals from a cluster of satellites in orbit around the earth so as to be capable of automatically indicating the locations of the local control systems disposed at each of the local sites 51a', 51b', 51c'. As such, the specific location of each local control system is able to be communicated to the command computer 59b of the central control system 58 via the Internet-based connection 60. In addition, as shown in FIG. 17, the central control system 58 may also include a GPS module 78 that communicates with the cluster of GPS satellites 77 and the GPS receiver units 76 at the local sites 51a', 51b', 51c'.

In the illustrative embodiment, as shown in FIG. 17, the Global Positioning System (GPS) is included in the laser delivery system (i.e., at local sites 51a', 51b', 51c') located away from the control site or doctor's office (i.e. at the remote site), providing information logged in its memory on where the laser system is located at any time or where the system might have been transported from the time of the construction to where it is moved in real time or is recorded in the system and can be retrieved.

In one or more embodiments, smartphones, computers, or the remote controlled laser systems at local sites 51a', 51b', 51c' are equipped with GPS so that the system starts sending the information on the position of the device as soon as the laser delivery system, a phone, or a computer is turned on.

In one or more embodiments, the GPS capabilities of the system are automatically switched on so that when the system sends a signal, it is received by the laser control system along with photographs or video if the 3-D camera is activated at the doctor's office located away from the laser system. When the system is turned on, the system automatically transmits a signal about its position at all times, which can be received by the control system while a data pusher tracks the device.

In one embodiment, the high definition system permits you to zoom into the video and maintain the clarity of the image at any point.

In one or more embodiments, the laser delivery system or a smartphone or a computer may contain covert GPS trackers and the camera of the laser delivery system identifies the patient, person, or people that are present along with the patient's medical history, or any other personal record, etc.

In one or more embodiments, the unit is programmed so that if the GPS is touched, or in any way manipulated, it will self-destruct (e.g., after either being exposed to the light, or mechanically handled). For example, piezoelectric nanoparticles may be used to create an electrical signal that is deadly to the function of the GPS and render it incapable of sending a signal that is able to be recognized.

In one embodiment, the receiver's computer at the doctor's office first indicates the position of the sender, then it evaluates and matches parameters that indicate the identity of the location, by automatically turning on the cameras of the laser delivery system recording and sending out live stream of video as is the case, for example, with the Skype™ system. The system captures images and/or sound related to the environment, person(s), etc. and analyzes them using familiar faces and/or voices, such as the nurse's face and/or voice, and the necessary physiological functions and their changes (e.g., changes in the face, etc.) indicating the familiar person and the prior history.

The system may also send a distress signal, which initiates a remote signal to the desired original place and automatically activates a signal to damage the laser delivery system and its software to prevent its operation.

In one embodiment, the person or patient who is being examined or treated is checked and his or her identity is verified before any communication between the remote system and the doctor's office is established by the data obtained and the software available at the doctor's location prior to the system acknowledging that the connection line is open to further interaction.

In one embodiment, the software at the doctor's location decides about whether to permit the patient's site to communicate with the doctor, etc. by comparing or matching the present data with the previous data that is available to the system.

In one embodiment, the doctor initiates communication by checking any variations and the trends in the changes of the physiological function of the patient located at the remote area while the system evaluates and correlates it with available data.

In one embodiment, the remote laser delivery system always comprises a component that is in a permanently "on" position so as to connect the system to the GPS, which indicates the exact and detailed present location of the remotely located system via a live GPS map, while recording automatically the time and the map if the unit has been moved. The GPS module 78 indicates any changes in the position of the unit on the background map and/or generates images or other information for the doctor.

In one embodiment, the camera system is turned on permanently and records the surroundings using its pattern recognition and/or 3-D display. As such, the system identifies the location and a person using the static and non-static or physiological changes that have occurred to identify the person or persons or patient(s), etc., and transmits the data to the doctor's site automatically using a 3D (stereo) camera with a head-up display.

In one embodiment, the camera at the remote laser delivery site, is a digital light field photography (DLFP) camera requiring microlenses that captures the information about the direction of the incoming light rays or a plenoptic unit where the arrays of photosensors pixels are placed behind the microlenses, and algorithms of the software are used to process the information obtained, as known in the art.

In one embodiment, the camera of the remote laser delivery system is equipped with a light field camera, such as Illum, CAFADIS, or robotic eye, that can provide information at different distances from the camera located in front or behind the focal point of the camera using software of the computer creating 3-D images, or stereo images using the software or graphics processing units (GPUs) or field programmable gate arrays (FPGAs).

In one embodiment, the doctor permits the system to analyze the data for identification using the system software analyzing in the memory bank the different normal versus abnormal variables, positive or negative variables, and other associations so as to create a pattern of significant association and create a coated color intelligent association of the past and present images.

In one embodiment, after verification of the person, the system permits examination of a lesion, surface, or internal structure with ultraviolet (UV) to infrared light, optical coherence tomography (OCT), ultrasound, or photoacoustic images to compare with the existing information from the patient and from other patients so as to provide potential diagnosis and options for therapy, while the system verifies the location, person(s) or patient(s) involved, etc. before proceeding with the therapy or an action and before the doctor runs the simulation of a laser treatment, if needed.

In one embodiment, the system provides for remote imaging or pattern recognition for a patient, persons, a surface, mucosal marking, or lesion along with verification using multi-spectral imaging, OCT, ultrasound or photoacoustic imaging and physical and physiological analysis to compare the surface lesions for shape pattern circulation thickness in 2 to 3 dimensions with the lesions or faces seen previously and existing in its file to diagnose a lesion, face, etc. and analyze the status of the progression of a disease, aging, and provide a list of options to be used in each case that can be complemented with the existing worldwide experiences stored in the memory of the computer of the unit.

In one embodiment, the connection to another requested computer is routed through the central location to verify the signal as a "friend" with all the patient's information or person's recognition live prior to giving the permission to be connected to another system elsewhere.

In one embodiment, all the process and personal recognition is automatically stored at the central location and may be retrieved again by a doctor or a person already known by the system. The desired 2-D, 3-D, or video images may be retrieved along with recordings of the conversations between the parties.

In one embodiment, the control system performs only one way recognition of the person at the remote location. In another embodiment, for an extreme security sensitive and urgent communication, the control system verifies the people or each person on both sides live from its existing files, and then opens the communication to establish a secure bilateral system, mostly for short and concise communications while the two-way system can initiate only from the doctor's office side, thereby adding another layer of confidence or veracity to the information.

In one embodiment, the existence of the system is known to only the people with top security clearance that carry a specific computer and cell phone.

In one embodiment, the computer of the laser delivery system at both the central and the remote location, or the laptop, and cell phones are replaced with new ones after the entire information is retrieved and the data is cleaned.

Laser-Imaging System with Photodynamic Therapy (PDT) Capabilities

In another further embodiment, the laser-imaging system 50, 50' may be configured to provide remote photodynamic therapy (PDT) for the patient. More particularly, in this further embodiment, the treatment laser of the laser generation system may be configured and arranged to perform the photodynamic therapy (PDT). In this embodiment, the PDT treatment method utilizes the combined effects of a photosensitizer in presence of oxygen and a light of a specific wavelength emitted by the treatment laser that is absorbed by the photosensitizer so as to create a chemical reaction, thereby producing singlet oxygen and reactive species. These are in oxidative processes and are toxic to the tissue damaging the cellular mitochondria if the photosensitizer is located inside the cell. If the photosensitizer is located outside the cell in contact with the cell membrane, it damages the cell membrane (e.g., endothelial cell membrane of the vessels). The damage to the endothelial cell wall of the vessels causes platelet aggregation, cloth formation, and closure of the vessel. Addition of an anti-vascular growth factor to the PDT enhances damage to the abnormal blood vessels produced by the tumor.

In this further embodiment, after inducing the physiological changes described above and verifying the patient's identification for the procedure, the site and location of the intravenous injection of a PDT photosensitizer and/or a surface lesion is captured by the image recognition sensor 73 of the laser-imaging system 50' and displayed to the remote physician on the 3D display so that it can be verified by the physician. Then, a combination of the photosensitizer and anti-VEGF, such as Avastin or other agents (e.g., anti-platelet derived growth factors) is applied to enhance damage to a cancerous lesion, such as skin or mucosa. Also, in addition to the photosensitizer, an anti-cancer medication, an anti-cancer immunotherapy medication, such as Braf and Mek targeted therapy, and/or a programmed cell death PD-1 immunotherapy to enhance damage to the cancerous lesion may be applied. After the PDT procedure, the patient is advised by the physician to avoid sun exposure for one week to prevent a sun radiation effect on other parts of the body.

Also, in this further embodiment, after inducing the physiological changes and verifying the patient's identification for the PDT procedure using the 3D display, nanoparticles coated with a biocompatible polymer and a photosensitizer conjugated with a thermosensitive polymer, such as chitosan, etc., are applied to the cancerous lesion of the patient. The nanoparticles may be metallic, non-metallic, synthetic, organic, non-organic, a hybrid, magnetic, paramagnetic, diamagnetic, supramagnetic, non-magnetic, and combinations thereof. The nanoparticles may be in the form of graphene-oxide quantum dots, graphene-zinc oxide quantum dots, graphene nanotubes, and/or carbon nanotubes. The nanoparticles may contain a combination of two to three elements, such as gold, gold-iron oxide, iron oxide, iron-zinc oxide, metallic nanoparticles, polylacticglycolic acid nanoparticles, ceramic nanoparticles, silica nanoparticles, silica crosslinked block polymer micelles, albumin-based nanoparticles, albumin-PEG nanoparticles, dendrimer attached magnetic or non-magnetic nanoparticles, etc. The nanoparticles also may be in the form of dendrimers, micelles, fullerenes, quantum dots, nanoshells, nanocages, nanorods, nanotubes, nanowires, and combinations thereof. The nanoparticles may be formed from gold and silica, ferric oxide, ferric, cadmium sulfate, platinum, etc., and may be coated with polyethylene glycol (PEG), fatty acid, chitosan, or another biocompatible molecule and conjugated with a tumor antibody and a photosensitizer. The nanoparticles may be conjugated with a tumor antibody and a cell penetrating peptide (CPP) so as to enhance the penetration of the photosensitizer in the tumor cells. The photosensitizer and/or nanoparticles, may be given intravenously, applied topically, or taken orally. Preferably, the anti-VEGF is applied locally to avoid the side effects of systemic administration, unless it is delivered as coated nanoparticles which are functionalized with an antibody to seek specifically a tumor cell. In general, the functionalized nanoparticles are taken up preferentially by the tumor cells and the growing proliferating endothelial cells of the abnormal tumor cells. When administered intravenously, the photosensitizer and/or nanoparticles may be configured to reach the desired area and attach to the desired tumor cells by utilizing a monoclonal antibody, a polyclonal antibody, or aptamer-coated nanoparticles to seek out the tumor cells. Also, in this embodiment, functionalized pluralities of nanoparticles, which are coated with a photosensitizer, may be given topically or systemically to a tumor located on or close to the skin or mucosa of the body.

In this further embodiment, the nanoparticles may be in the form of three dimensional semiconductor devices using light or ultrasound energy to generate electrical energy to provide a photovoltaic effect. In embodiments, the nanoparticle material may be ceramic, plastic, silicon; particles of crystalline silicon may be monocrystalline cells, poly or multicrystalline cells, ribbon silicon having a multicrystalline structure, nanocrystals of synthetic silicon, gallium/arsenide, cadmium/selenium, copper/indium/gallium/selenide, zinc sulfide, iron sulfide, iron-platinum, indium/gallium/phosphide, gallium arsenide, indium/gallium nitride, a nanocrystal, such as cadmium/selenium (Cd/Se) and a metal, e.g., a CdSe/Au nanometer-sized composite particle as previously described, particles of a variety of semiconductor/metal and semiconductor/semiconductor hetero-junctions, e.g., particles based upon semiconductor/metal hetero-junctions between group II-VI, IV, III-V, IV-VI, referring to groups of the periodic table, metal-oxide, or organic semiconductors and a metal, and in particular those based upon Si/Au, GaAs/Au, InAs/Au, and PbS/Au hetero-junctions. The quantum dots and/or semiconductor nanowires may also be biocompatible short peptides of naturally occurring amino acids that have the optical and electronic properties of semiconductor nano-crystals, e.g., short peptides of phenylalanine. The particles can consist of both inorganic and organic materials, as previously described. In addition to being stimulated by light and ultrasound energy, the nanoparticles may also be stimulated by microwave radiation, magnetic fields, alternating magnetic fields, and radiofrequency (RF) electromagnetic radiation.

Moreover, in this further embodiment, the application of the treatment laser for PDT is substantially applied in a continuous wave (CW) fashion at wavelengths that are absorbed by the nanoparticles and/or the photosensitizer. The laser spot generated by the treatment laser may be applied as a single spot covering the entire cancerous lesion and slightly beyond it. Alternatively, the treatment laser may be applied as a small spot, but using a painting or oscillatory technique by displacing an electrically controlled prism or a mirror, which is located in front of the treatment laser beam, in an oscillatory manner. In this embodiment, the treatment laser of the laser generation system may produce a wavelength appropriate for the photosensitizer (e.g., a wavelength of 405 nanometers (nm) to 420 nm, or 500 nm to 600 nm, or 635 nm, a near-infrared laser from 600 to 1060 nm-1550 nm and more, up to an infrared wavelength) which is absorbed by the photosensitizer and penetrates the skin and mucosa up to a distance of 1 centimeter (cm) in the tissue. In one or more embodiments, the treatment laser may comprise a powerful non-coherent light source from any light, such as a xenon or mercury lamp, rather a coherent light source.

Furthermore, in this further embodiment, the patient's cancerous lesion may be pre-treated by the topical application of the photosensitizer and/or nanoparticles through the skin or mucosa, for a period of 1-30 minutes depending on the thickness of the lesion to be treated. The photosensitizer may comprise one of aminolevulinic acid, methyl aminolevulinate, Verteporfin, and riboflavin, etc. Advantageously, riboflavin is a non-toxic photosensitizer which still normally kills the tumor cells, and cross-links the collagen around the tumors so as to strangulate and close their vascular supply as a result of its photodynamic effect. In one exemplary embodiment, a Verteporfin photosensitizer preparation is conjugated with cell penetrating peptides (CPP) or activated cell penetrating peptides (ACPP) and polyethylene glycol (PEG), etc. coated nanoparticles, and after the identity of the patient is verified in the manner described above, the preparation is administered intravenously to reach internally and externally-located tumor cells. In this embodiment, the size of the nanoparticles is maintained below 10 nanometers (nm) to enhance their secretion through the kidney and urine. In other embodiments, the sizes of the nanoparticles are from 1 nm to 1000 nm. When the photosensitizer is an aminolevulinic acid or methyl aminolevulinate, it is preferentially absorbed by the lesion specific antibody-coated nanoparticles so as to provide a lesion specific response in the lesion because the area of the skin or mucosa that does not contain photosensitizer will not respond to the light and will not be affected.

In this further embodiment, riboflavin may be applied topically in a biocompatible solution, the treatment laser may be configured to emit ultraviolet (UV) laser light therefrom. For example, topical applications of 1% to 2% riboflavin in a biocompatible solution may be applied as drops for 1 to 20 minutes depending on the concentration of the riboflavin and the power of ultraviolet laser light (e.g., 2 mW to 20 mW) to activate the riboflavin (the higher the concentration of riboflavin or the laser power, the less time is needed to conclude radiation). In this further embodiment, the antibody nanoparticles may be conjugated with riboflavin and polymers, such as polyethylene glycol, chitosan, etc. for systemic, intravenous, or local application.

Also, in this further embodiment, the photosensitizer (e.g., riboflavin) may be used topically in physiological solution to the infected skin or mucosal wound by bacteria, fungi, or other organisms, such as amoebas, that are therapy resistant to medication, alone or with antibiotics or antifungals or the medication, while the infected wound is exposed to UV radiation of 380 mm in wavelength or higher for the appropriate time depending on the riboflavin concentration and/or the laser energy to cross-link the collagen of the tissue and simultaneously kill the offending organism. Riboflavin is vitamin B2, and is important for maintenance of the health of the human body. In this further embodiment, the laser wavelength may be chosen depending on the absorption of the photosensitizer (e.g., the absorption of the riboflavin).

In addition, in this further embodiment, after inducing the physiological changes and verifying the patient's identification for the PDT procedure using the 3D display, the presence of any lesion on the skin or mucosa, and the size, elevation and the physiological parameters of the lesion are compared before, during, and/or after the procedure with the results of the previous initial examination. In this embodiment, the surface of the skin or mucosa is treated with a solution containing pluralities of coated, thermosensitive nanoparticles conjugated with a polyethylene glycol (PEG) and a thermosensitive polymer, such as chitosan, a cell penetrating peptide (CPP), a photosensitizer, and at least one more medication that is released from the chitosan, when the temperature of the nanoparticles reaches 41 to 43 deg. C. In this embodiment, the temperature of the lesion may be maintained at 41 to 43 deg. C. to release the medication from the thermosensitive polymer and to prevent a pain sensation. The temperature may be raised to 45 to 47 degrees C. for a very short time, while applying prophylactically, a topical anesthetic medication in order to kill the cells without creating tissue burn. In another embodiment, the photosensitizer may be released from the thermosensitive polymer coating of the nanoparticles when the temperature reaches 38 to 43 deg. C. Also, in another embodiment, the temperature may be raised up to 43 to 45 degrees C., 45 to 47 degrees C., or up to 50 deg. C. to kill the cancerous cells of a lesion on the skin mucosa and other accessible areas. The treatment laser of the laser-imaging system 50, 50' not only activates the thermosensitive photosensitizers, but also heats up the nanoparticles, etc. Any follow-up treatments are done with the same remotely-controlled laser and camera system which is equipped with 3D display described above for accurate recognition and examination of the lesion.

In this further embodiment, when the patient has a skin or mucosal lesion or cancer, the combination of the photoacoustic components of the system (i.e., the laser and ultrasonic transducer described above) creates not only a 2D image of the surface structure, but using the system as photoacoustic tomography provides a 3D image of the lesion providing gross or microscopic information about the depth that the lesion has penetrated inside the skin or mucosa, while also providing volumetric information to be measured in the follow-up examination of the patient. The 3D image of the lesion may also provide information about the effect of the treatment on the lesion in the subsequent follow-up period, while the data is simultaneously transmitted to a doctor or observer located at the remote site. Also, the photoacoustic system may be used to provide information about a small region of a larger structure, such as the breast, exhibiting early signs of potential cancer in the tissue in an early stage of the disease when the lesion is very small (e.g., 1 to 2 mm dimension) that is difficult to image by using electromagnetic radiation (i.e., x-ray) or computerized tomography (CT) scan, etc.

Also, in this further embodiment, the photosensitizer and/or nanoparticles are treated with a laser, for a period of 1 to 30 minutes or more, under observation by processor control, while the laser delivery system is under the control of the photoacoustic system to control the amount of energy delivered to the lesion for a predetermined time. A thermoacoustic response is recorded simultaneously and a thermal map is created continuously, to prevent heating the tissue beyond the predetermined temperature of between 39 and 44-47 deg. C. as needed, etc. without creating a thermal burn.

In this further embodiment, the treatment system provides a combination effect of PDT if the temperature is maintained below 42 degrees C., and simultaneously a thermal effect if the temperature is gradually raised using a photoacoustic imaging system to keep the temperature below the temperature in which protein denatures, which is about 50 degrees C. depending on the duration of the application and power of the treatment laser.

In this further embodiment, the treatment laser of the remotely-controlled laser system is used for the PDT of a Basal cell carcinoma, squamatous cell cancer of the skin, angioma, senile keratosis, precancerous melanosis, melanoma, cancer of the mouth mucosa, throat, nose, vaginal mucosa, cervix, or the uterus. The PDT may also be used to treat photoaging, acne vulgaris, dry eye to enhance meibomian gland secretion, Bowen's disease of the eye or lids, and the PDT may also be used to deliver strong light therapy to damage and kill bacteria, such as *Propionibacterium acnes*, bacteria in blepharitis, or to treat infected corneas that are infected by bacteria, fungi, viruses, and amoebas, etc.

System Software Platform

The software system that is employed to control the laser procedure(s) with the laser-imaging systems of the invention includes client/server architecture and a TCP/IP communication protocol. The client/server architecture comprises a computer science paradigm, where clients and servers are deemed separate software processes that can run on the same or different computers.

In some embodiments, the software recognizes the computer at the surgeon's site as a client, while the local control module at the remote patient's site is recognized as a server.

According to the invention, communication by and between the remote control module 64 and the local control module 62 is facilitated via web services implemented in .NET remoting technology.

When a physician at a remote site sends a control or data acquisition command, the command is first transmitted to the local control module 62 (or server) through the .NET remoting interface. In response to the command, the local control module 62 controls hardware compartments through a hardware specific interface (e.g., RS-232C interface, parallel communication protocol).

The communication speed between the client and the server will depend on several factors such as 1) the distances between the client and the server, 2) network traffic conditions, and 3) the size of data (e.g., images) being transmitted.

As will readily be appreciated by one having ordinary skill in the art, the present invention provides numerous advantages compared to prior art methods and systems for laser coagulation procedures. Among the advantages are the following:

The provision of laser-imaging systems, which will significantly reduce laser transmission and, hence, procedure time. For example, the length of time for the laser photo-coagulation treatment for diabetic retinopathy will be reduced from 30-60 minutes per procedure to only two minutes. In general, the duration of a single laser pulse, plus the time it takes to perform the subsequent laser application multiplied by the total number of pulses required is equal to the overall procedure time. The manner in which the pulses are applied in a conventional contact system (e.g., using a contact lens positioned on the cornea in order to see the fundus) requires the physician (i.e., ophthalmologist) to perform the procedure laser shot by laser shot (i.e., to place a single laser spot at a desired location and then move on to the next location). When performing the procedure on a patient that requires 1000-2000 laser spots, the laser coagulation procedure can easily take 30 minutes or more. The laser coagulation system disclosed herein uses millisecond laser pulses (and in some cases, less than millisecond pulses), and each subsequent laser shot is performed automatically, in some embodiments, by utilizing an oscillating mirror (e.g., oscillating mirror 220 described above) placed in the path of the laser beam such that the laser beam is displaced without requiring any manual means. In addition, the wide angle camera employed in one or more embodiments described herein enables the entire retina to be viewed, rather than just a small portion thereof, thereby further reducing procedure time. As a result of these enhanced features, the laser coagulation system described herein substantially reduces the overall procedure time. In one embodiment, the remote operation module of the laser coagulation system is configured to perform a fully automated and continuous laser coagulation procedure over the entire area of the retina in a period of time no greater than approximately 2 minutes (or no greater than 2 minutes) in an actual control mode.

The provision of laser-imaging systems, which will also reduce the probability of error associated with manual surgery (tremors and misjudgments) via a more precise computerized control mechanism, with additional fail-safe features, and a wider angle imaging camera for retina diseases. This offers more choices for various lasers with different wavelengths, intensities, and action than was previously possible.

The provision of laser-imaging systems, which will also allow a physician or surgeon to perform a procedure at a remote site, via a high-speed reliable Internet® connection, thus eliminating the need for the patient to travel a long distance to be treated at a specialist's office or, in the case of military field care or space exploration units, allowing patients to be treated immediately on-site.

The laser coagulation system described herein is in the form of a non-contact system that does not require the use of a contact lens or any other device in contact with the eye of the patient. The laser coagulation system embodied herein also does not require the physician to indent any portion of the patient's eye (i.e., no indenter or scleral depressor is required to indent the peripheral portion of the patient's eye). As a result, the patient is far more comfortable during the laser coagulation procedure.

The cameras employed in the systems can also be equipped with appropriate diode lasers and filters for auto-fluorescence photography and angiography of the retina.

One can also develop a miniature version of the system by using printing technology, such as inkjet, to generate and integrate the micro-optical parts not only on hard substrates, but also on those that are flexible. Having a miniature or micro-system will allow further use of such technology in hard to reach places.

Any of the features or attributes of the above described embodiments and variations can be used in combination with any of the other features and attributes of the above described embodiments and variations as desired.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A telemedicine system with dynamic imaging, comprising:
   a local control system disposed at a first location and a central control system disposed at a remote site, said remote site being at a second location, said local control system being operatively coupled to said central control system by means of a computer network;
   said local control system including a first computing device with a first processor, a local control module, and a dynamic imaging system;
   said central control system including a second computing device with a second processor and a remote control module;
   said dynamic imaging system including an imaging device operatively coupled to said first computing device, said imaging device configured to capture images of a body portion of a patient over a predetermined duration of time so that a displacement of said body portion of said patient is capable of being tracked during said predetermined duration of time, said captured images including an initial captured image containing first image data that is produced without requesting said patient to perform any task, and said captured images further including a subsequent captured image containing second image data that is produced as a result of said patient being instructed to perform a task that induces one or more detectable physical and physiological changes in said body portion of said patient, said first computing device being programmed to determine said displacement of said body portion of said patient over said predetermined duration of time using said captured images, and to compare said displacement of said body portion of said patient over said predetermined duration of time to a reference displacement of said body portion of said patient acquired prior to said displacement so that a plurality of induced physical and physiological dynamic changes in said body portion of said patient are capable of being assessed for the purpose of identifying said patient or evaluating physiological changes in said body portion, and said first computing device being further programmed to compare using a subtraction algorithm said plurality of induced physical and physiological dynamic changes to said body portion of said patient captured by said imaging device at a first time to said plurality of induced physical and physiological dynamic changes to said body portion of said patient captured by said imaging device at a second subsequent time, and to determine if said plurality of induced physical and physiological dynamic changes captured by said imaging device at said first time substantially matches said plurality of induced physical and physiological dynamic changes to said body portion of said patient captured by said imaging device at said second subsequent time so as to verify the identity of said patient;
   wherein the body portion is a face and the subtraction algorithm eliminates unchanged parts of the face, while maintaining changed parts of the face to enhance the processing speed.

2. The telemedicine system according to claim 1, wherein said imaging device of said dynamic imaging system is in the form of a light field camera.

3. The telemedicine system according to claim 1, wherein said dynamic imaging system is in the form of a dynamic facial recognition system, and wherein the face or a portion of the face of said patient is imaged in a two-dimensional or three-dimensional manner.

4. The telemedicine system according to claim 3, wherein said first computing device is further programmed to reconstruct a complete face from the portion of the face captured by the dynamic facial recognition system using artificial intelligence and/or a machine learning algorithm.

5. The telemedicine system according to claim 3, wherein said dynamic imaging system further comprises a fingerprint sensor configured to capture multispectral images of a finger of said patient, said first computing device being specially programmed to determine surface features and subsurface features of said finger of said patient using said multispectral images.

6. The telemedicine system according to claim 3, wherein said dynamic imaging system further comprises a handwriting recognition sensor configured to capture handwriting of said patient, said first computing device being specially programmed to determine an identity of said patient based upon said handwriting of said patient captured by said handwriting recognition sensor.

7. The telemedicine system according to claim 3, wherein said first computing device is further programmed to utilize a fuzzy logic mathematical algorithm in order to differentiate an identity of two similar images captured by said dynamic facial recognition system.

8. The telemedicine system according to claim 3, wherein said first computing device is further programmed to add or subtract features from the face of said patient captured by said dynamic facial recognition system in order to facilitate the identity recognition of said patient when an appearance of said patient changes over time, said added or subtracted features selected from the group consisting of addition of hair, removal of hair, addition of facial hair, removal of facial hair, addition of jewelry, removal of jewelry, addition of eyewear, and removal of eyewear.

9. The telemedicine system according to claim 3, wherein said first computing device is further programmed to change features of the face of said patient captured by said dynamic facial recognition system in order to facilitate the identity recognition of said patient when an appearance of said patient changes over time, said changed features selected from the group consisting of skin color, hair color, eye color, presence or absence of hair, presence or absence of facial hair, presence or absence of jewelry, and presence or absence of eyewear.

10. The telemedicine system according to claim 3, wherein said first computing device is programmed to compare one or more first reference digital images of said patient captured by said imaging device of said dynamic facial recognition system at a first time to one or more second digital images of said patient captured by said imaging device of said dynamic facial recognition system at a second subsequent time using stable features of the face of said patient, and to determine if said one or more second digital images of said patient substantially matches said one or more first reference digital images of said patient, said stable features selected from the group consisting of a nose position, an eye position, a mouth position, spacing between eyes, spacing between the nose and one or more of the eyes, spacing between the nose and the mouth, eye features, nose features, mouth features, ear features, and geometric facial features.

11. The telemedicine system according to claim 3, wherein said first computing device is further programmed to change emotionally affected features on an image of the face of said patient captured by said dynamic facial recognition system in order to facilitate the identity recognition of said patient when an emotional state of said patient is different.

12. The telemedicine system according to claim 1, wherein said changed parts of said face of said patient for which said displacement is determined comprises a mouth of said patient; and
wherein said telemedicine system further comprises a voice recognition sensor configured to capture speech waveforms generated by said patient so that said speech waveforms are capable of being correlated with a mouth configuration of said patient generated from said captured images acquired using said imaging device, thereby enabling both audial and visual attributes of said patient to be taken into account for identification purposes.

13. The telemedicine system according to claim 1, wherein said imaging device of said dynamic imaging system is in the form of a multispectral camera or hyperspectral camera configured to capture multispectral or hyperspectral images of said body portion of said patient so that surface features and subsurface features of said body portion of said patient are capable of being analyzed.

14. The telemedicine system according to claim 13, wherein said first computing device is operatively coupled to a visual display device and one or more speakers, said first computing device being programmed to display a range of images and/or videos on said visual display device and/or play a variety of different sounds on said one or more speakers to evoke different emotional states of said patient, and said first computing device being further programmed to record dynamic changes in said body portion of said patient with said multispectral camera or hyperspectral camera while evoking the different emotional states of said patient so that a response of said patient to said different emotional states is able to be analyzed.

15. A telemedicine system with dynamic imaging, comprising:
a local control system disposed at a first location and a central control system disposed at a remote site, said remote site being at a second location, said local control system being operatively coupled to said central control system by means of a computer network;
said local control system including a first computing device with a first processor, a local control module, and a facial recognition system;
said central control system including a second computing device with a second processor and a remote control module;
said facial recognition system including an imaging device operatively coupled to said first computing device, said imaging device configured to capture one or more images of a face of a patient, said captured images including an initial captured image containing first image data that is produced without requesting said patient to perform any task, and said captured images further including a subsequent captured image containing second image data that is produced as a result of said patient being instructed to perform a task that induces one or more detectable physical and physiological changes in said face of said patient, said first computing device being programmed to compare using a subtraction algorithm said plurality of induced physical and physiological dynamic changes to said face of said patient captured by said imaging device of said facial recognition system at a first time to said plurality of induced physical and physiological dynamic changes to said face of said patient captured by said imaging device of said facial recognition system at a second subsequent time, and to determine if said plurality of induced physical and physiological dynamic changes captured by said imaging device at said first time substantially matches said plurality of induced physical and physiological dynamic changes to said face of said patient captured by said imaging device at said second subsequent time so as to verify the identity of said patient;
wherein the subtraction algorithm eliminates unchanged parts of the face, while maintaining changed parts of the face to enhance the processing speed.

16. The telemedicine system according to claim 15, wherein said first computing device is further programmed to receive consent from said patient for telemedicine communication by receipt of verbal confirmation, a confirmatory head motion, a confirmatory hand motion, a confirmatory eye motion, and/or by receipt of a fingerprint from said patient.

* * * * *